US010060912B2

(12) United States Patent
Lim et al.

(10) Patent No.: US 10,060,912 B2
(45) Date of Patent: Aug. 28, 2018

(54) GLOBAL PROTEOMIC SCREENING OF RANDOM BEAD ARRAYS USING MASS SPECTROMETRY IMAGING

(71) Applicant: AmberGen, Inc., Watertown, MA (US)

(72) Inventors: Mark J Lim, Reading, MA (US); Vladislav B Bergo, Boston, MA (US); Kenneth J Rothschild, Newton, MA (US)

(73) Assignee: AmberGen, Inc., Watertown, MA (US)

( * ) Notice: Subject to any disclaimer, the term of this patent is extended or adjusted under 35 U.S.C. 154(b) by 0 days.

(21) Appl. No.: 15/283,694

(22) Filed: Oct. 3, 2016

(65) Prior Publication Data

US 2017/0089891 A1   Mar. 30, 2017

Related U.S. Application Data

(63) Continuation of application No. 13/172,164, filed on Jun. 29, 2011, now Pat. No. 9,523,680.

(60) Provisional application No. 61/359,964, filed on Jun. 30, 2010.

(51) Int. Cl.
  *G01N 33/53*   (2006.01)
  *G01N 33/543*   (2006.01)
  *G01N 33/68*   (2006.01)

(52) U.S. Cl.
  CPC ...  *G01N 33/54306* (2013.01); *G01N 33/5308* (2013.01); *G01N 33/6845* (2013.01); *G01N 33/6848* (2013.01)

(58) Field of Classification Search
  None
  See application file for complete search history.

(56) References Cited

U.S. PATENT DOCUMENTS

| | | | |
|---|---|---|---|
| 5,643,722 A | 7/1997 | Rothschild et al. | 435/6.13 |
| 5,922,858 A | 7/1999 | Rothschild et al. | 536/24.1 |
| 5,948,624 A | 9/1999 | Rothschild et al. | 435/6.13 |
| 5,981,180 A | 11/1999 | Chandler et al. | 435/6.12 |
| 5,986,076 A | 11/1999 | Rothschild et al. | 536/22.1 |
| 6,057,096 A | 5/2000 | Rothschild et al. | 435/6.13 |
| 6,210,941 B1 | 4/2001 | Rothschild et al. | 435/183 |
| 6,218,530 B1 | 4/2001 | Rothschild et al. | 536/25.32 |
| 6,303,337 B1 | 10/2001 | Rothschild et al. | 435/69.1 |
| 6,306,628 B1 | 10/2001 | Rothschild et al. | 435/91.3 |
| 6,344,320 B1 | 2/2002 | Rothschild et al. | 435/6.13 |
| 6,358,689 B1 | 3/2002 | Rothschild et al. | 435/6.13 |
| 6,566,070 B2 | 5/2003 | Rothschild et al. | 435/6.13 |
| 6,589,736 B1 | 7/2003 | Rothschild et al. | 435/6.13 |
| 6,596,481 B1 | 7/2003 | Rothschild et al. | 435/6.13 |
| 6,875,592 B2 | 4/2005 | Rothschild et al. | 435/91.1 |
| 6,949,341 B2 | 9/2005 | Rothschild et al. | 435/6.13 |
| 7,057,031 B2 | 6/2006 | Olejnik et al. | 536/25.3 |
| 7,169,558 B2 | 1/2007 | Rothschild et al. | 435/6.13 |
| 7,195,874 B2 | 3/2007 | Rothschild et al. | 435/6.13 |
| 7,211,394 B2 | 5/2007 | Rothschild et al. | 435/6.13 |
| 7,252,932 B1 | 8/2007 | Rothschild et al. | 435/6.13 |
| 7,288,372 B2 | 10/2007 | Olejnik et al. | 435/6.13 |
| 7,312,038 B2 | 12/2007 | Rothschild et al. | 435/6.13 |
| 7,339,045 B2 | 3/2008 | Rothschild et al. | 536/23.1 |
| 7,422,855 B2 | 9/2008 | DiCesare | 435/6.11 |
| 7,423,122 B2 | 9/2008 | Rothschild et al. | 530/350 |
| 7,485,427 B1 | 2/2009 | Rothschild et al. | 435/6.13 |
| 7,524,941 B2 | 4/2009 | Olejnik et al. | 534/554 |
| 7,547,530 B2 | 6/2009 | Olejnik et al. | 435/6.13 |
| 7,569,392 B2 | 8/2009 | Levy et al. | 435/6 |
| 7,892,854 B2 | 2/2011 | Banerjee et al. | 436/525 |
| 8,071,393 B2 | 12/2011 | Seul | 436/518 |
| 2005/0266407 A1 | 12/2005 | Chee | 435/6.11 |
| 2009/0088332 A1 | 4/2009 | Ju et al. | 506/9 |
| 2009/0264298 A1 | 10/2009 | Lim et al. | 506/1 |
| 2009/0270278 A1 | 10/2009 | Lim et al. | 506/27 |
| 2009/0286286 A1 | 11/2009 | Lim et al. | 435/91.2 |
| 2010/0062451 A1 | 3/2010 | Lim et al. | 435/7.1 |
| 2010/0075374 A1 | 3/2010 | Lim et al. | 435/68.1 |

FOREIGN PATENT DOCUMENTS

WO   WO 2007/000669   4/2007

OTHER PUBLICATIONS

Abramoff, et al., "Image Processing With ImageJ". *Biophotonics International*, 11(7):36-422 (2004).
Aguiar, et. al., "High-Throughput Generation of *P. falciparum* Functional Molecules by Recombinational Cloning." *Genome Res.*, 14:2076-82, (2004).
Aguiar, et. al., "High-Throughput Generation of *P. falciparum* Functional Molecules by Recombinational Cloning." *Genome Res.*, 14:2076-82, Supplemental Table 1 (2004).
Aguiar, et. al., "High-Throughput Generation of *P. falciparum* Functional Molecules by Recombinational Cloning." *Genome Res.*, 14:2076-82, Supplemental Table 2 (2004).
Al-Hashimi, "Sjögren's Syndrome: Diagnosis and Management." Womens Health (Lond Engl) 3:107-22 (2007).
Alamanos, et. al., "Epidemiology of Primary Sjögren's Syndrome in North-West Greece, 1982-2003." *Rheumatology* (Oxford) 45:187-91 (2006).
American College of Rheumatology, "Position Statement." (http://www.rheumatology.org/publications/position/ana_position_stmt. pdf)_(2009).
Anderson, et. al., "Application of Protein Microarrays for Multiplexed Detection of Antibodies to Tumor Antigens in Breast Cancer." *J Proteome Res* 7:1490-9 (2008).
Auburn, et. al., "Robotic Spotting of cDNA and Oligonucleotide Microarrays." *Trends Biotechnol* 23:374-9 (2005).
Babel, et. al., "Identification of Tumor-Associated Autoantigens for the Diagnosis of Colorectal Cancer in Serum Using High Density Protein Microarrays." *Mol Cell Proteomics* 8:2382-95 (2009).

(Continued)

*Primary Examiner* — Changhwa J Cheu
(74) *Attorney, Agent, or Firm* — Medien & Carroll, LLP

(57) ABSTRACT

Methods for proteomic screening on random protein-bead arrays by mass spec is described. Photocleavable mass tags are utilized to code a protein library (bait molecules) displayed on beads randomly arrayed in an array substrate. A library of probes (prey) can be mixed with the protein-bead array to query the array. Because mass spec can detect multiple mass tags, it is possible to rapidly identify all of the interactions resulting from this mixing.

26 Claims, 44 Drawing Sheets

(56) References Cited

OTHER PUBLICATIONS

Figure 1:
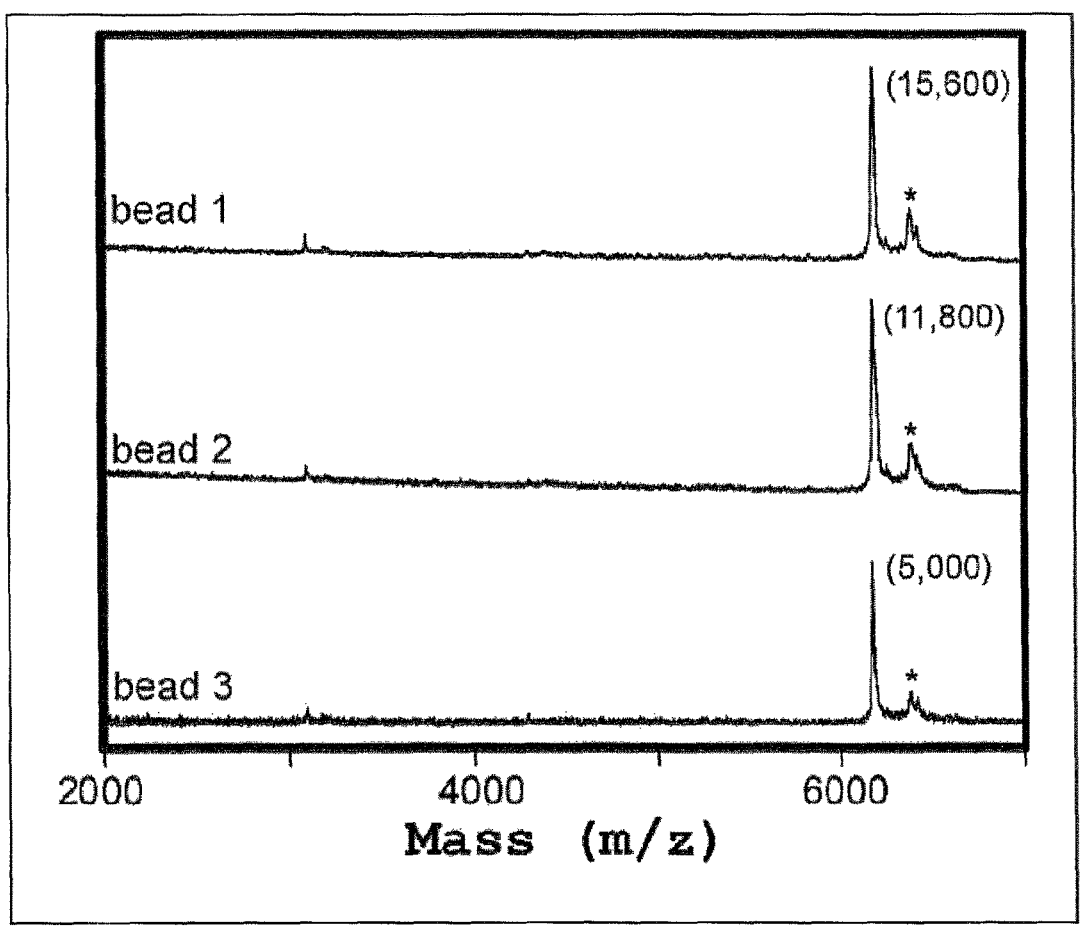

Bier, et. al., "DNA Microarrays." *Adv Biochem Eng Biotechnol* 109:433-53 (2008).
Bloch, et. al., "The Cytoplasmic Dot Staining Pattern is Detected in a Subgroup of Patients With Primary Biliary Cirrhosis." *J Rheumatol* 32:477-83 (2005).
Boozer, et. al., "Looking Towards Label-Free Biomolecular Interaction Analysis in a High-Throughput Format: A Review of New Surface Plasmon Resonance Technologies." *Curr Opin Biotechnol* 17:400-5 (2006).
Borrebaeck and Wingren, "Design of High-Density Antibody Microarrays for Disease Proteomics: Key Technological Issues." *J Proteomics* 72:928-35 (2009).
Cappuccio, et. al., "Cell-free Co-expression of Functional Membrane Proteins and Apolipoprotein, Forming Soluble Nanolipoprotein Particles." *Mol Cell Proteomics* 7:2246-53 (2008).
Cappuccio, et. al., "Cell-free Co-expression of Functional Membrane Proteins and Apolipoprotein, Forming Soluble Nanolipoprotein Particles." *Mol Cell Proteomics* 7:2246-53 Supplemental Data (2008).
Cappuccio, et. al., "Cell-free expression for Nanolipoprotein Particles: Building a High-Throughput Membrane Protein Solubility Platform." *Methods Mol Biol* 498:273-96 (2009).
Celis, "Human and Mouse Proteomic Databases: Novel Resources in the Protein Universe." *FEBS Lett* 430:64-72 (1998).
Centers for Disease Control and Prevention (CDC), "Trends in Deaths From Systemic Lupus Erythematosus—United States, 1979-1998." *MMWR Morb Mortal Wkly Rep.*, 51:371-4 (2002).
Chakravarty, et. al., "Prevalence of Adult Systemic Lupus." *Arthritis Rheum.*, 56:2092-4 (2007).
Chapman, et. al., "Autoantibodies in Lung Cancer: Possibilities for Early Detection and Subsequent Cure." *Thorax* 63:228-33 (2008).
Chapman, et. al., "Autoantibodies in Lung Cancer: Possibilities for Early Detection and Subsequent Cure." *Thorax* 63:228-33 Supplementary data (2008).
Collins and Choudhary "Mapping multiprotein complexes by affinity purification and mass spectrometry." *Curr Opin Biotechnol* 19:324-30(2008).
Davies, et. al., "Colorectal Cancer Screening: Prospects for Molecular Stool Analysis." *Nat Rev Cancer* 5:199-209 (2005).
Dressman, et. al., "Transforming Single DNA Molecules Into Fluorescent Magnetic Particles for Detection and Enumeration of Genetic Variations." *Proc Natl Acad Sci* USA 100:8817-22 (2003).
Endo and Sawasaki, "High-Throughput, Genome-Scale Protein Production Method Based on the Wheat Germ Cell-Free Expression System." *Biotechnol Adv* 21:695-713 (2003).
Enjalbal , et. al., "Mass Spectrometry and Combinatorial Chemistry: New Approaches for Direct Support-Bound Compound Identification." *J L Comb Chem High Throughput Screen.* 4(4):363-73 (2001).
Franz, et. al., "High-Throughput One-Bead-One-Compound Approach to Peptide-Encoded Combinatorial Libraries: MALDI-MS Analysis of Single TentaGel Beads." *J. Comb. Chem.*, 5:125-137 (2003).
Fulton, et. al., "Advanced Multiplexed Analysis With the FlowMetrix™ System." *Clin Chem.*, 43:1749-56 (1997).
Gabriel, et. al., "SNP Genotyping Using the Sequenom MassARRAY iPLEX Platform." *Curr Protoc Hum Genet.*, Chapter 2: Unit 2.12, Wiley Interscience, (2009).
Gibbs, "Differential Post-Translational Modification of Human Type I Keratins Synthesized in a Rabbit Reticulocyte Cell-Free System." *Acta* 824:247-55 (1985).
Gite, et al., "Ultrasensitive Fluorescence-Based Detection of Nascent Proteins in Gels." *Anal Biochem* 279:218-225 (2000).
Gite, et al., "A High-Throughput Nonisotopic Protein Truncation Test." *Nat Biotechnol* 21:194-197 (2003).
Gite, et al., "Cell-Free Protein Synthesis Systems: Biotechnological Applications." *Biotechnology & Genetic Engineering Reviews*, 22:151-169 (2006).

Goff and Goldberg, "An Increased Content of Protease La, The Lon Gene Product, Increases Protein Degradation and Blocks Growth in *Escherichia coli*." *J Biol Chem.*, 262:4508-15 (1987).
Goshima, et al., "Human Protein Factory for Converting the Transcriptome Into an In Vitro-Expressed Proteome." *Nat Methods*, 5:1011-7 (2008).
Graham, et al., "High-throughput Methods for Measuring Autoantibodies in Systemic Lupus Erythematosus and other Autoimmune Diseases." *Autoimmunity* 37:269-72 (2004).
Guadagni, et al., "Differential Expression of a New Tumor-Associated Antigen, TLP, During Human Colorectal Cancer Tumorigenesis." *Am J Pathol.*, 154:993-9 (1999).
Han, et al., "Quantum-Dot-Tagged Microbeads for Multiplexed Optical Coding of Biomolecules." *Nat Biotechnol.*, 19:631-635 (2001).
Hatcher, et al., "Monitoring Activity-Dependent Peptide Release from the CNS Using Single-Bead Solid-Phase Extraction and MALDI TOF MS." *Detection Anal. Chem.*, 77:1580-1587 (2005).
He and Taussig, "Method for Screening and MALDI-TOF MS Sequencing of Encoded Combinatorial Libraries." *Nucleic Acids Res.*, 29:E73-3 (2001).
Henrich, et al., "Lysis of *Escherichia coli* by Induction of Cloned Phi X174 Genes." *Mol Gen Genet.*, 185:493-7 (1982).
Hirose, et al., "In Vitro Biosynthesis of Human Renin and Identification of Plasma Inactive Renin as an Activation Intermediate." *J Biol Chem.*, 260:16400-5(1985).
Hirsch, et. al., "Easily Reversible Desthiobiotin Binding to Streptavidin, Avidin, and Other Biotin-Binding Proteins: Uses for Protein Labeling, Detection, and Isolation." *Anal Biochem.*, 308:343-57 (2002).
Hu, et. al., "Method for Screening and MALDI-TOF MS Sequencing Oof Encoded Combinatorial Libraries." *Anal. Chem.*, 79:7275-7285 (2007).
Hudson, et al., "Identification of Differentially Expressed Proteins in Ovarian Cancer Using High-Density Protein Microarrays." *Proc Natl Acad Sci USA* 104:17494-9 (2007).
International Human Genome Sequencing Consortium, "Finishing the Euchromatic Sequence of the Human Genome." *Nature*, 431:931-45 (2004).
Jacobson, et al., "Epidemiology and Estimated Population Burden of Selected Autoimmune Diseases in the United States." *Clin Immunol Immunopathol.*, 84:223-43 (1997).
Jaskowski, et al., "Screening for Antinuclear Antibodies by Enzyme Immunoassay." *Am J Clin Pathol.*, 105:468-73 (1996).
Kaplan, "Primary Biliary Cirrhosis." *N Engl J Med.*, 335:1570-80 (1996).
Kaplan, "Primary Biliary Cirrhosis: Past, Present, and Future." *Gastroenterology*, 123:1392-4 (2002).
Katzen, et al., "Insertion of Membrane Proteins Into Discoidal Membranes Using a Cell-Free Protein Expression Approach." *J Proteome Res.*, 7:3535-42 (2008).
Kawahashi, et al., "In Vitro Protein Microarrays for Detecting Protein-Protein Interactions: Application of a New Method for Fluorescence Labeling of Proteins." *Proteomics*, 3:1236-43 (2003).
Koesters, et al., "WT1 is a Tumor-Associated Antigen in Colon Cancer That can be Recognized by In Vitro Stimulated Cytotoxic T Cells." *Int J Cancer*, 109:385-92 (2004).
Koster, et al., "A Strategy for Rapid and Efficient DNA Sequencing by Mass Spectrometry." *Nat Biotechnol.*, 14:1123-1128 (1996).
Kroshinsky et. al., "Case 37/2009—A 46-Year-Old Woman with Chronic Renal Failure, Leg Swelling, and Skin Changes." *N Engl J Med.*, 361:2166-76 (2009).
Leung, et al., "Antimitochondrial Antibodies in Primary Biliary Cirrhosis." *Semin Liver Dis.*, 17:61-9 (1997).
Li, et al., "Identification of Hepatocellular-Carcinoma-Associated Antigens and Autoantibodies by Serological Proteome Analysis Combined With Protein Microarray." *J Proteome Res.*, 7:611-20 (2008).
Lim and Rothschild, "Photocleavage-Based Affinity Purification and Printing of Cell-Free Expressed Proteins: Application to Proteome Microarrays." *Anal Biochem.*, 383:103-115 (2008).
Lin, et al., "Medium- to High-Throughput SNP Genotyping Using Veracode Microbeads." *Methods Mol Biol.*, 496:129-42 (2009).

(56) References Cited

OTHER PUBLICATIONS

Line, et al., "Characterisation of Tumour-Associated Antigens in Colon Cancer." *Cancer Immunol Immunother.*, 51:574-82 (2002).

Lyford and Rosenberg, "Cell-Free Expression and Functional Reconstitution of Homo-Oligomeric Alpha7 Nicotinic Acetylcholine Receptors Into Planar Lipid Bilayers." *J Biol Chem.*, 274:25675-81 (1999).

MacBeath, et al., "Printing Proteins as Microarrays for High-Throughput Function Determination." *Science* 289:1760-1763 (2000).

Maccalli, et al., "Identification of a Colorectal Tumor-Associated Antigen (COA-1) Recognized by CD4 + T Lymphocytes." *Cancer Res.*, 63:6735-43 (2003).

Mahler, et al., "Improved Serological Differentiation between Systemic Lupus Erythematosus and Mixed Connective Tissue Disease by Use of an SmD3 Peptide-Based Immunoassay." *Clin Diagn Lab Immunol.*, 12:107-13 (2005).

Mahler, "Challenges and Controversies in Autoantibodies Associated with Systemic Rheumatic Diseases." *Current Rheumatology Reviews*, 3:67-78 (2007).

Mamaev, et al., "Cell-Free N-Terminal Protein Labeling Using Initiator Suppressor tRNA." *Anal Biochem* 326:25-32 (2004).

Manoussakis, "Sjögren's Syndrome." *Orphanet Encyclopedia*, (2004).

Mathur and Kelso, "Multispectral Image Analysis of Binary Encoded Microspheres for Highly Multiplexed Suspension Arrays." *Cytometry A*, 77(4):356-65 (2010).

Melton, "Protein Arrays: Proteomics in Multiplex." *Nature* 429:101-7 (2004).

Michaud, et al., "Analyzing Antibody Specificity With Whole Proteome Microarrays." *Nat Biotechnol.*, 21:1509-1512 (2003).

Michael, et al., "Randomly Ordered Addressable High-Density Optical Sensor Arrays." *Anal Chem.*, 70:1242-1248 (1998).

Middleton and Bulleid, "Reconstitution of the Folding Pathway of Collagen in a Cell-Free System: Formation of Correctly Aligned and Hydroxylated Triple Helices." *Biochem J.*, 296 (Pt 2):511-7 (1993).

Muro, et al., "Use of SNP-Arrays for ChIP Assays: Computational Aspects." *Methods Mol Biol.*, 567:145-54 (2009).

Nakano and Yamane, "Cell-free protein synthesis systems." *Biotechnol Adv.*, 16:367-84 (1998).

Nord, et al., "Microbead Display of Proteins by Cell-Free Expression of Anchored DNA." *J Biotechnol.*, 106:1-13 (2003).

Olejnik, et al., "Photocleavable Biotin Derivatives: A Versatile Approach for the Isolation of Biomolecules." *Proceedings of the National Academy of Science (USA)* 92:7590-7594 (1995).

Olejnik, et al., "Photocleavable Biotin Phosphoramidite for 5'-End-Labeling, Affinity Purification and Phosphorylation of Synthetic Oligonucleotides." *Nucleic Acids Research*, 24:361-366 (1996).

Olejnik, et al., "Photocleavable Aminotag Phosphoramidites for 5'-Termini DNA/RNA Labeling." *Nucleic Acids Research*, 26:3572-6 (1998).

Olejnik, et al., "Photocleavable Peptide—DNA Conjugates: Synthesis and Applications to DNA Analysis Using MALDI-MS." *Nucleic Acids Research*, 27:4626-4631 (1999).

Olejnik, et al., "N-Terminal Labeling of Proteins Using Initiator tRNA." *Methods*, 36:252-60 (2005).

PD MidiTrap G-25 Desalting Column (GE Healthcare Life Sciences, Piscataway, N.J.) Sep. 2009.

Pandori, et. al., "Photochemical Control of the Infectivity of Adenoviral Vectors Using a Novel Photocleavable Biotinylation Reagent." *Chem Biol* 9:567-73 (2002).

Patton, et. al., Two-Dimensional Gel Electrophoresis; Better Than a Poke in the ICAT? *Curr Opin Biotechnol.*, 13:321-8 (2002).

Pensiero, et. al., "Binding of the Coronavirus Mouse Hepatitis Virus A59 to Its Receptor Expressed From a Recombinant Vaccinia Virus Depends on Posttranslational Processing of the Receptor Glycoprotein." *J Virol.*, 66:4028-39 (1992).

Philip, et. al., "Shared Immunoproteome for Ovarian Cancer Diagnostics and Immunotherapy: Potential Theranostic Approach to Cancer." *J Proteome Res.*, 6:2509-17 (2007).

Pillemer, et. al., "Incidence of Physician-Diagnosed Primary Sjögren Syndrome in Residents of Olmsted County, Minnesota." *Mayo Clin Proc.*, 76:593-9 (2001).

Popov, et al., "Mapping the Ends of Transmembrane Segments in a Polytopic Membrane Protein Scanning N-Glycosylation Mutagenesis of Extracytosolic Loops in the Anion Exchanger, Band 3." *J Biol Chem* 272:18325-32 (1997).

Pregibon, et. al., "Multifunctional Encoded Particles for High-Throughput Biomolecule Analysis." *Science*, 315(5817):1393-6 (2007).

Ramachandran, et al., "Self-Assembling Protein Microarrays." *Science*, 305:86-90 (2004).

Rathore, et al., "Extending Matrix-Assisted Laser Desorption/Ionization Triple Quadrupole Mass Spectrometry Enzyme Screening Assays to Targets With Small Molecule Substrates." *Rapid Commun Mass Spectrom.* 23(20):3293-300 (2009).

Robinson, et. al., "Millennium Award. Proteomics for the Development of DNA Tolerizing Vaccines to Treat Autoimmune Disease." *Clin Immunol.*, 103:7-12 (2002a).

Robinson, et al., "Proteomics Technologies for the Study of Autoimmune Disease." *Arthritis Rheum.*, 46:885-93 (2002b).

Robinson, et al., "Autoantigen Microarrays for Multiplex Characterization of Autoantibody Responses." *Nat Med.*, 8:295-301 (2002c).

Robinson, et al., "Protein Microarrays Guide Tolerizing DNA Vaccine Treatment of Auto Immune Encephalomyelitis." *Nat Biotechnol.*, 21:1033-1039 (2003).

Ross, et al., "High Level Multiplex Genotyping by MALDI-TOF Mass Spectrometry." *Nat Biotechnol.*, 16:1347-1351 (1998).

Rothschild, et al., "tRNA-mediated protein engineering." *Curr Opin Biotechno.,l* 10:64-70 (1999).

Rual, et al., "Human ORFeome Version 1.1: A Platform for Reverse Proteomics." *Genome Res* 14:2128-35 (2004).

Rual, et al., "Human ORFeome Version 1.1: A Platform for Reverse Proteomics." *Genome Res* 14:2128-35 SDFig2 (2004).

Rual, et al., "Human ORFeome Version 1.1: A Platform for Reverse Proteomics." *Genome Res* 14:2128-35 SDFig1 (2004).

Rual, et al., "Human ORFeome Version 1.1: A Platform for Reverse Proteomics." *Genome Res* 14:2128-35 SDTable1 (2004).

Sawasaki, et. al., "A Bilayer Cell-Free Protein Synthesis System for High-Throughput Screening of Gene Products." *FEBS Lett.*, 514:102-5 (2002).

Schena, et. al., "Quantitative Monitoring of Gene Expression Patterns with a Complementary DNA Microarray." *Science* 270:467-70 (1995).

Schulze and Downward, "Navigating Gene Expression Using Microarrays—A Technology Review." *Nat Cell Biol.*, 3:E190-5 (2001).

Shaffer, "Next-Generation Sequencing Outpaces Expectations." *Nat Biotechnol.*, 25:149 (2007).

Sherer, et. al., "Autoantibody Explosion in Systemic Lupus Erythematosus: More Than 100 Different Antibodies Found in SLE Patients." *Semin Arthritis Rheum.*, 34:501-37 (2004).

Sheridan, "Protein Biochip Companies Turn to Biomarkers." *Nat Biotechnol* 23: 3-4 (2005).

Stein, "Human Genome: End of the Beginning." *Nature*, 431:915-6 (2004).

Suresh, "Systemic Lupus Erythematosus: Diagnosis for the Non-Specialist." *Br J Hosp Med (Lond)* 68:538-41 (2007).

Suter, et. al., "Two-Hybrid Technologies in Proteomics Research." *Curr Opin Biotechnol.*, 19:316-23 (2008).

Talwalkar and Lindor, "Primary Biliary Cirrhosis." *Lancet* 362: 53-61 (2003).

Takano, et. al., "Use of a Phosphosensor Dye in Proteomic Analysis of Human Mutant tau Transgenic Mice." *Neuroreport*, 20:1648-53 (2009).

Ulmer, et. al., "Tumor-Associated Antigen 90K/Mac-2-Binding Protein: Possible Role in Colon Cancer." *J Cell Biochem.*, 98:1351-66 (2006).

(56) References Cited

OTHER PUBLICATIONS

Ulvestad, et. al., "Evaluation of Diagnostic Tests for Antinuclear Antibodies in Rheumatological Practice." *Scand J Immunol.*, 52:309-15 (2000).
Von Muhlen and Tan, "Autoantibodies in the Diagnosis of Systemic Rheumatic Diseases." *Semin Arthritis Rheum.*, 24:323-58 (1995).
Vitali, et. al., "Classification Criteria for Sjögren's Syndrome: A Revised Version of the European Criteria Proposed by the American-European Consensus Group." *Ann Rheum Dis.*, 61:554-8 (2002).
Vorburger, et. al., "Modification of Nuclear Lamin Proteins by a Mevalonic Acid Derivative Occurs in Reticulocyte Lysates and Requires the Cysteine Residue of the C-terminal CXXM Motif." *EMBO J.*, 18:4007-13 (1989).
Ward, "Prevalence of Physician-Diagnosed Systemic Lupus Erythematosus in the United States: Results From the Third National Health and Nutrition Examination Survey." *J Womens Health (Larchmt)*, 13:713-8 (2004).
Warren, et. al., "Development of a Protein Chip: A MS-Based Method for Quantitation of Protein Expression and Modification Levels Using an Immunoaffinity Approach." *Anal Chem.*, 76(14):4082-92 (2004).
Washburn, et. al., "Large-Scale Analysis of the Yeast Proteome by Multidimensional Protein Identification Technology." *Nat Biotechnol* 19:242-7 (2001).
Wasinger, et. al., "Progress With Gene-Product Mapping of the Mollicutes: *Mycoplasma genitalium*." *Electrophoresis*, 16:1090-4 (1995).
Yang, et. al., "Do Antinuclear Antibodies in Primary Biliary Cirrhosis Patients Identify Increased Risk for Liver Failure?" *Clin Gastroenterol Hepatol.*, 2:1116-22 (2004).
Yau and Holmes, "CNV Discovery Using SNP Genotyping Arrays." *Cytogenet Genome Res.*, 123:307-12 (2008).
Zhang et. al., "Quantifying DNA-Protein Binding Specificities by Using Oligonucleotide Mass Tags and Mass Spectroscopy." *Proc Natl Acad Sci USA*, 104:3061-6 (2007).
Zhu, et. al., "Analysis of Yeast Protein Kinases Using Protein Chips." *Nat Genet.*, 26:283-9 (2000).
Zhu, et. al., "Global Analysis of Protein Activities Using Proteome Chips." Science 293:2101-5 (2001).
Gallus Immunotech product brochure_20130731a, "About IgY: Table 1: Comparison of IgG, IgE, IgY and IgY (ΔFc)" 2013.
Song, et al., "A novel and rapid encoding method based on mass spectrometry for "one-bead-one-compound" small molecule combinatorial libraries." J Am Chem Soc. 125(20):6180-6188, 2003.

GLOBAL PROTEOMIC SCREENING OF RANDOM BEAD ARRAYS USING MASS SPECTROMETRY IMAGING

CROSS-REFERENCE TO RELATED APPLICATIONS

This application claims priority to U.S. Provisional Application Ser. No. 61/359,964 filed Jun. 30, 2010, herein incorporated by reference in its entirety for all purposes.

FIELD OF THE INVENTION

This invention relates to biology, molecular biology, biochemistry, cell biology, biomedicine, biomarkers and clinical diagnostics; proteomics, reverse proteomics and mass spectrometry; bio-molecular arrays, microarrays, bead-arrays, and bead-displays; multiplexed assays and bio-assays; and label-free bio-molecular detection. More specifically, the invention relates to detecting or imaging molecules or compounds on individual beads or particles using mass spectrometry as applied to the aforementioned fields.

BACKGROUND OF THE INVENTION

A. Multiplexing in Bio-Molecular Detection

There is a continuing realization that the complexities of biological systems can neither be fully understood nor harnessed by taking single measurements or determinations in a single assay or experimental process. As a result, the biological, biotechnological and biomedical fields continue to move towards multiplexing, that is, the capability to perform simultaneous, multiple determinations in a single assay or experimental process [U.S. Pat. No. 5,981,180].

A.1 Multiplexing with Planar Bio-Molecular Arrays and Microarrays

One important advancement in multiplexed biological experimentation or bio-assays has been through the introduction of microarrays, or so-called "chips", which consist normally of an ordered and addressable array of tens of thousands of microscopic spots or "features", usually robotically printed [MacBeath and Schreiber (2000) Science 289: 1760-3.; Auburn, Kreil, Meadows, Fischer, Matilla and Russell (2005) Trends Biotechnol 23: 374-9] to a single planar substrate typically the dimensions of a standard microscope slide; each feature containing a unique "bait" molecule, most commonly oligonucleotides or proteins, including antibodies. The entire chip is typically treated with a simple or complex biological sample or complex mixture of molecules and the bait molecules on the chip bind or interact with the analyte(s) in the sample. These analytes are sometimes termed prey molecules. It is also to be understood that prey molecules may constitute biomarkers in a complex mixture or molecules in a solution whose interaction with the bait molecules is to be determined. In some cases, the bound analyte(s) are measured, in others, the effects of analyte (prey molecule) interaction with the bait molecules is measured, for example, whereby an analyte, such as a protein kinase, enzymatically modifies a bait molecule on the chip (in this case, phosphorylation of the bait by the protein kinase). The chip is then scanned or imaged in order to detect these interactions, usually through a variety of fluorescence "reporter" methods. Alternatively, other reporters such as radioisotopes have been used [MacBeath and Schreiber (2000) Science 289: 1760-3.]. Furthermore, label-free methods such as surface plasmon resonance [Boozer, Kim, Cong, Guan and Londergan. (2006) Curr Opin Biotechnol 17: 400-5] or mass spectrometry [Gabriel, Ziaugra and Tabbaa (2009) Curr Protoc Hum Genet Chapter 2: Unit 2 12] are also possible. In some cases, a "probe" is used to assist in detection, for example, a substance that binds a bait-bound analyte, such as antibody, and is capable if being detected (e.g. labeled).

DNA microarrays [Schena, Shalon, Davis and Brown (1995) Science 270: 467-70] are now widely used and accepted by the scientific community, most commonly used for multiplexed, "genome-wide" analysis of the entire expressed mRNA complement of a cell, tissue or other biological sample. In this case, the microarray features are oligonucleotide bait molecules that bind complementary mRNA or cDNA from a complex biological sample. Other examples of DNA microarray applications include single nucleotide polymorphism (SNP) genotyping and mutation analysis [Bier, von Nickisch-Rosenegk, Ehrentreich-Forster, Reiss, Henkel, Strehlow and Andresen (2008) Adv Biochem Eng Biotechnol 109: 433-53], copy number variation (CNV) [Yau and Holmes (2008) Cytogenet GenomeRes 123: 307-12] and chromatin immunoprecipitation (ChIP) analyses (so called ChIP-on-Chip) [Muro, McCann, Rudnicki and Andrade-Navarro (2009) Methods Mol Biol 567: 145-54].

Likewise, protein microarrays [MacBeath and Schreiber (2000) Science 289: 1760-3.; Zhu, Klemic et al. (2000) Nat Genet 26: 283-9] are rapidly gaining popularity. The most widely used forms can be classified as: i) "capture chips", whereby the features/probes on the microarray correspond to affinity capture elements, usually antibodies, used to quantify the level of various analytes in a complex biological sample or ii) "interaction chips", whereby protein features/probes on the microarray, usually recombinant proteins, are used to measure biologically relevant interactions, such as protein-protein or protein-drug interactions or enzymatic/chemical modification of the protein probes on the microarray.

A.2 Multiplexing with Suspension Arrays and Bead-Arrays

While fixed addressable/ordered microarrays are one mode of bio-assay multiplexing, bead or particle based multiplexing, sometimes referred to as "suspension arrays" or "bead arrays" affords many advantages [Mathur and Kelso (2009) Cytometry A]. Advantages include for example: i) "solution-phase" or homogeneous reaction and binding kinetics; i) elimination of the need for mechanical printing and drying of the microarray probes, a procedure which is subject to failure such as misprinting and is also known to damage delicate biomolecules such as proteins; iii) increased density (diversity) of the bead-based probe libraries due to the facile production of very small, e.g. submicron diameter, beads or particles thereby allowing several orders of magnitude higher multiplexing levels compared to 2-dimensional planar microarrays. For example, bead-arrays in etched microscopic hexagonally packed wells can reach densities of $10^9/cm^2$ [Michael, Taylor, Schultz and Walt (1998) Anal Chem 70: 1242-8] versus $10^4/cm^2$ for mechanically printed spots on 2-dimensional planar microarrays [Mathur and Kelso (2009) Cytometry A]; iv) the ability to physically isolate sub-populations of beads or particles based on specific properties; and v) more facile use of 3-dimensional hydrated solid-matrices for probe attachment, such as commonly available porous agarose beads, that offer a more bio-compatible surface as well as higher probe binding capacities than planar microarrays.

A.3 Mainstream Light Based Bead Coding Methods

Methods of encoding and decoding beads or particles are required in order to facilitate the aforementioned bead-based multiplex bio-assays and exploit their many advantages. Prominent commercial examples of multiplex bead/particle platforms include the xMAP® technology of Luminex Corporation (Austin, Tex.), which uses beads encoded with fluorescent dyes and readout on a flow cytometry based platform [Fulton McDade, Smith, Kienker and Kettman (1997) Clin Chem 43: 1749-56], and VeraCode technology of Illumina Incorporated (San Diego, Calif.), which uses microscopic cylindrical glass microbeads encoded with digital holographic "bar codes" [Lin, Yeakley, McDaniel and Shen (2009) Methods Mol Biol 496: 129-42]. Other examples of light based or spectral coding of beads or particles have been reported. For example, in 2001 Han et al. predicted that more than 40,000 distinct codes should be possible, for example when fluorescent quantum dot nanocrystals are permanently embedded in beads at different ratios of color and intensity [Han, Gao, Su and Nie (2001) Nat Biotechnol 19: 631-5]. However, in practice, such methods to date have not exceed a few hundred codes [Mathur and Kelso (2009) Cytometry A]. Other optical encoding techniques, for example employing lithography (Multifunctional encoded particles for high-throughput biomolecule analysis. (Pregibon D C, Toner M, Doyle P S. *Science.* 2007 Mar. 9; 315(5817):1393-6) or fluorescence of rare earth elements (Parallel Synthesis Technologies Inc; www.parallume.com) can potentially generate hundreds of thousands of unique codes but have not yet demonstrated their commercial viability.

A.4 Mass Coding of Beads or Particles and Mass Spectrometry

Mass spectrometry (MS) has been used extensively as an analytical technique in biotechnology for a variety of applications including proteomics, biomarker discovery, genomic analysis and clinical assays [Koster, H., Tang, K., Fu, D. J., Braun, A., van den Boom, D., Smith, C. L., Cotter, R. J., and Cantor, C. R. (1996) Nat Biotechnol 14, 1123-1128]. Very high throughputs are obtained because separation times are measured in microseconds rather than minutes or hours compared to conventional methods such as gel electrophoresis [Ross, P., Hall, L., Smirnov, I., and Haff, L, (1998) Nat Biotechnol 16, 1347-1351]. Additional information, such as protein sequence and modifications occurring at specific residues is also possible using tandem mass spectrometry (MS/MS) [Washburn, Wolters and Yates (2001) Nat Biotechnol 19: 242-7].

The extremely high resolution and mass accuracy of mass spectrometry offers the potential to greatly increase the number of possible unique identification "codes" for beads or particles. Indeed, in the field of proteomics, those skilled in the art will recognize that mass spectrometry is a critical tool used in the identification of proteins. In atypical proteomics scenario, proteins are digested, such as by protease, and identification of the protein achieved by one of two ways using mass spectrometry a) mass fingerprinting—for a single species of digested protein (such as that isolated by two-dimensional gel electrophoresis prior to digestion), the pattern of masses of the daughter peptide fragments ("fingerprint") can be sufficient for identification or b) tandem mass spectrometry based sequencing of even a single daughter peptide fragment can be sufficient for identification (e.g. see [Washburn, Wolters et al. (2001) Nat Biotechnol 19: 242-7]).

Not surprisingly, for multiplexed bio-assays, mass spectrometry has been used in conjunction with so called "mass tags" as coding agents, for example peptide mass tags [Olejnik, Ludemann, Krzymanska-Olejnik, Berkenkamp, Hillenkamp and Rothschild (1999) Nucleic Acids Res 27: 4626-311] and oligonucleotide mass tags [Zhang, Kasif and Cantor (2007) Proc Natl Acad Sci USA 104: 3061-6] have been reported. U.S. Pat. No. 6,218,530, "Compounds and Methods for Detecting Biomolecules" hereby specifically incorporated into this application (has peptide mass tags in specifications). Previously, mass tags have been used to code bead libraries and detected by mass spectrometry, particularly in the fields of combinatorial chemistry and solid-phase organic synthesis. However, in these studies the detection was performed after elution of the mass tags and not directly from individual beads or from arrays of particles using mass spectrometric imaging techniques. The elution was achieved by either prolonged exposure to acid or UV irradiation [*J Comb. Chem.* 2003, 5, 125-137 "High-Throughput One-Bead-One-Compound Approach to Peptide-Encoded Combinatorial Libraries: MALDI-MS Analysis of Single Tenta-Gel Beads" Andreas H. Franz, Ruiwu Liu, Aimin Song, Kit S. Lam, and Carlito B. Lebrilla; *Anal. Chem.* 2007, 79, 7275-7285 "Method for Screening and MALDI-TOF MS Sequencing of Encoded Combinatorial Libraries" Bi-Huang Hu, Marsha Ritter Jones, and Phillip B. Messersmith] or alternatively, in the case of peptides attached to beads through hydrophobic or antibody-mediated interactions, simply by the addition of MALDI matrix [*Anal Chem.* 2004 Jul. 15; 76(14):4082-92. "Development of a protein chip: a MS-based method for quantitation of protein expression and modification levels using an immunoaffinity approach". Warren E N, Elms P J, Parker C E, Borchers C H.; *Anal. Chem.* 2005, 77, 1580-1587 "Monitoring Activity-Dependent Peptide Release from the CNS Using Single-Bead Solid-Phase Extraction and MALDI TOF MS" Detection Nathan G. Hatcher, Timothy A. Richmond, Stanislav S. Rubakhin, and Jonathan V. Sweedler]. Several studies have also reported direct detection of mass tags on beads and even examined their distribution within individual beads using secondary ion mass-spectrometry (SIMS) [Comb Chem High Throughput Screen. 2001 June; 4(4):363-73. "Mass spectrometry and combinatorial chemistry: new approaches for direct support-bound compound identification". Enjalbal C, Maux D, Martinez J, Combarieu R, Aubagnac J L]. The SIMS technique provides high lateral resolution down to sub-micron range, but unlike MALDI MS generates only small ions (MW below 400 Da) and is therefore not suitable for proteomic or nucleotide analysis. Importantly, all of the above studies do not describe MALDI-MS on individual beads or arrays of individual beads.

Mass spectrometry scanning or imaging can facilitate in situ detection of mass tags directly from individually resolved beads and be used to decode the bead for rapid identification of other molecules (e.g. bait and prey) directly or indirectly bound to the bead. In one embodiment, this is done by mass-imaging with a Matrix Assisted Laser Desorption Ionization Time of Flight (MALDI-TOF) mass spectrometer. For example, beads or particles are deposited onto a surface which is then scanned with the laser beam of the MALDI-TOF mass spectrometer, and a mass-image is created of the bead "array" using the peak intensity at the mass/charge ratio corresponding to that of the target compound (e.g. mass tag). Since the Nd-Yag laser beam used for MALDI-TOF mass spectrometry is diffraction limited, it can be focused to less than 1 micron, much smaller than the diameter of micro-beads (5-100 microns) commonly used for bio-assays. Typical beads used in bio-assays range from porous cross-linked agarose beads, to solid paramagnetic beads (often with polymeric shell), silica beads and plastic polymer beads such as polystyrene polymers or co-polymers. Pre-cursor beads often have surface chemistries (e.g. binding agents) to allow attachment of "bait" molecules or compounds needed for various bio-assays. Common bead surface chemistries include chemically reactive groups, such as aldehyde, epoxy or succinimidyl esters, or molecular handles such as amine, sulfhydryl or carboxyl moieties typically used in conjunction with chemical cross-linkers. Passive adsorption of protein or nucleic acid based molecules for example, is also possible, typically via hydrophobic and/or ionic interactions with surface modifications on the beads. All of these chemical groups are can potentially serve as binding agents for bait molecules or for other molecules such as mass tags. In addition, bioreative molecules bound to the surface of beads such as antibodies can also serve as binding agents for bait molecules or for other molecules such as mass tags.

The ability to perform mass spectrometry based scanning and mass-imaging of beads or particles, as described in this patent, opens the door for dramatic improvements in bio-assay multiplexing capabilities, with the potential for millions of codes and facilitating multiplexing both at the level of encoding beads or particles for identification as well as at the level of encoding the bio-molecular probes (sometimes termed prey molecules) present in samples or complex mixtures used to query the beads (e.g. beads which may contain various "bait" molecules such as recombinant proteins or antibodies for example). It is to be understood that in this invention biomarkers also in complex mixtures also constitute prey molecules.

B. Proteomics: Applications of Large-Scale Multiplexing in Bio-Molecular Detection

B.1 Proteomics

The "central dogma", first proposed by Francis Crick in the 1950's, describes the process by which the genetic material in cells, DNA, is converted to the cell's machinery, proteins. Now, after over 50 years, science has succeeded in decoding the DNA contained in the approximately 25,000 genes in the human genome [Consortium (2004) Nature 431: 931-45; Stein (2004) Nature 431: 915-6]. While this accomplishment represents a major success for this first "Manhattan-scale" project in biology, a much more ambitious goal is emerging for the post-genome era. This goal is to analyze the entire protein complement of the genome, first referred to as the proteome [Wasinger, Cordwell et al. (1995) Electrophoresis 16: 1090-4] in 1994 by Marc Wilkins and Keith Williams of the Macquarie University Center for Analytical Biotechnology (MUCAB) in Sydney, Australia. While the proteome is the entire expressed complement of a genome, those skilled in the art will recognize that proteomics involves the global analysis of entire proteomes in a single experimental process (i.e. multiplexed analysis).

In principle, just as whole genomes are now more rapidly analyzed using next-generation massively parallel DNA sequencing [Shaffer (2007) Nat Biotechnol 25: 149], equally powerful methods are needed for proteomics screening. The potential benefits of such screening for improving human health are enormous, since understanding the basis of diseases depends critically on understanding the machinery of the cell, i.e. proteins expressed by the genome.

In general, as detailed below, proteomics can be divided into two categories, that is, "classical" (forward) proteomics and reverse proteomics:

B.2 Classical Proteomics

In this "forward" proteomics model (see below for reverse), one begins with an entire proteome which is then linked or mapped to the genome during a protein analysis and identification process [Wasinger, Cordwell et al. (1995) Electrophoresis 16: 1090-4; Celis, Ostergaard, Jensen, Gromova, Rasmussen and Gromov (1998) FEBS Left 430: 64-72]. The proteomes are typically first extracted from complex biological samples such as cells, tissues or biological fluids for downstream multiplexed analysis. Classical proteomics methods were originally configured as separation and analysis of the entire extracted proteomes by two-dimensional gel electrophoresis, followed by identification of proteins excised from the gel by mass spectrometry [Wasinger, Cordwell et al. (1995) Electrophoresis 16: 1090-4], although identification by antibody recognition or protein sequencing has also been used [Celis, Ostergaard et al. (1998) FEBS Lett 430: 64-72]. Such approaches are now joined by "gel-free" or "shot-gun" proteomics methods that avoid the use of two-dimensional electrophoresis. These methods are usually based on fragmentation of the entire proteome into peptides, peptide pre-fractionation (typically by multi-dimensional high resolution liquid chromatography) and analysis/identification by mass spectrometry (see for example [Patton, Schulenberg and Steinberg (2002) Curr Opin Biotechnol 13: 321-8] and [Washburn, Wolters et al. (2001) Nat Biotechnol 19: 242-7]).

The most common application of classical proteomics is in differential protein expression profiling, where protein expression levels in a control sample are compared to that of a test sample in order to identify proteins of interest (e.g. disease associated) on a proteome-wide scale. However, variants have also been used, such as differential analysis of protein modification, for example, post-translational modifications such as phosphorylation (e.g. [Takano, Otani, Sakai, Kadoyama, Matsuyama, Matsumoto, Takenokuchi, Sumida and Taniguchi (2009) Neuroreport 20: 1648-53]).

In another embodiment of "forward" proteomics, extracted proteomes are mapped to the genome through specific recognition by affinity elements. In practice, this is usually achieved in multiplex format using antibody or "capture" arrays/microarrays, by capture and quantification of proteins from a complex mixture (proteome) using specific antibodies (affinity elements) printed to the array surface [Borrebaeck and Wingren (2009) J Proteomics 72: 928-35]. These techniques are also most typically used for proteome-wide protein expression profiling.

B.3 Interaction Based Proteomics

Expanding beyond the protein expression profiling that is typical of classical proteomics, an ideal proteomic screen would provide all the information necessary to identify all possible interactions between the M proteins in the proteome with N other molecules (e.g. proteome, nucleome and metabolome), in an M×N interaction matrix. It is to be understood in this case that there are M probe molecules and N prey molecules. In the case of a full probing of protein-protein interactions in a library of M proteins which potentially serve as both bait and prey, this matrix would have $M^2$ elements. While a variety of techniques exist to measure such interactions, they are usually based on screening the interaction of a single probe molecule against a set of other molecules, essentially providing only one row in the interaction matrix. One such extensively used method involves tandem affinity purification (TAP) of expressed target proteins and identification of interacting proteins by tandem mass spectrometry (MS/MS) [Collins and Choudhary (2008) Curr Opin Biotechnol 19: 324-30]. In contrast, yeast two-hybrid methods, based on in vivo screening of a protein library against a single protein or against an another library, can specify all the elements of an M×N matrix. However, this technique requires the screening and partial sequencing of M×N from different cell colonies, provides only binary information (e.g. interaction occurs or does not occur) and has as high as a 50% false-positive/negative rate [Suter, Kittanakom and Stagljar (2008) Curr Opin Biotechnol 19: 316-23].

B.4 Reverse Proteomics and Proteome Arrays

Reverse proteomics represents an important tool in interaction based proteomic screening. In this reverse format, a set of genes or a gene library (a "genome") is used to generate (synthesize) a proteome for study in a multiplexed format [Rual, Hirozane-Kishikawa et al. (2004) Genome Res 14: 2128-35]. In principle, the entire human proteome could be generated from the human genome and each protein analyzed for its different properties (e.g. protein interactions). While such a global translation of the human genome has never been achieved, even a limited set of genes can yield valuable information.

One widely used example of reverse proteomics is proteome microarrays (an "interaction chip"), that is, microarrays of purified recombinant proteins corresponding to an entire proteome (full expressed complement of a genome) or a large fraction thereof. Proteome microarrays are currently being used for various applications including mapping protein-protein interactions for elucidating cellular pathways [MacBeath and Schreiber (2000) Science 289: 1760-3.; Zhu, Bilgin et al. (2001) Science 293: 2101-5; Ramachandran, Hainsworth, Bhullar, Eisenstein, Rosen, Lau, Walter and LaBaer (2004) Science 305: 86-90], determining protein-small molecule interactions including with drug compounds [MacBeath and Schreiber (2000) Science 289: 1760-3.], analysis of enzymatic activities such as kinase substrate preference [MacBeath and Schreiber (2000) Science 289: 1760-3.; Zhu, Klemic et al. (2000) Nat Genet 26: 283-9], evaluating antibody specificity [Michaud, Salcius, Zhou, Bangham, Bonin, Guo, Snyder, Predki and Schweitzer (2003) Nat Biotechnol 21: 1509-12] and biomarker discovery [Sheridan (2005) Nat Biotechnol 23: 3-4], such as in the discovery of novel autoantigens in autoimmune diseases as well as cancers [Robinson, DiGennaro et al. (2002) Nat Med 8: 295-301; Robinson, Fontoura et al. (2003) Nat Biotechnol 21: 1033-9; Hudson, Pozdnyakova, Haines, Mor and Snyder (2007) Proc Natl Acad Sci USA 104: 17494-9; Babel, Barderas, Diaz-Uriarte, Martinez-Torrecuadrada, Sanchez-Carbayo and Casal (2009) Mol Cell Proteomics 8: 2382-95].

B.4.1 Conventional Cell-Derived Recombinant Proteome Arrays

Figure 20:
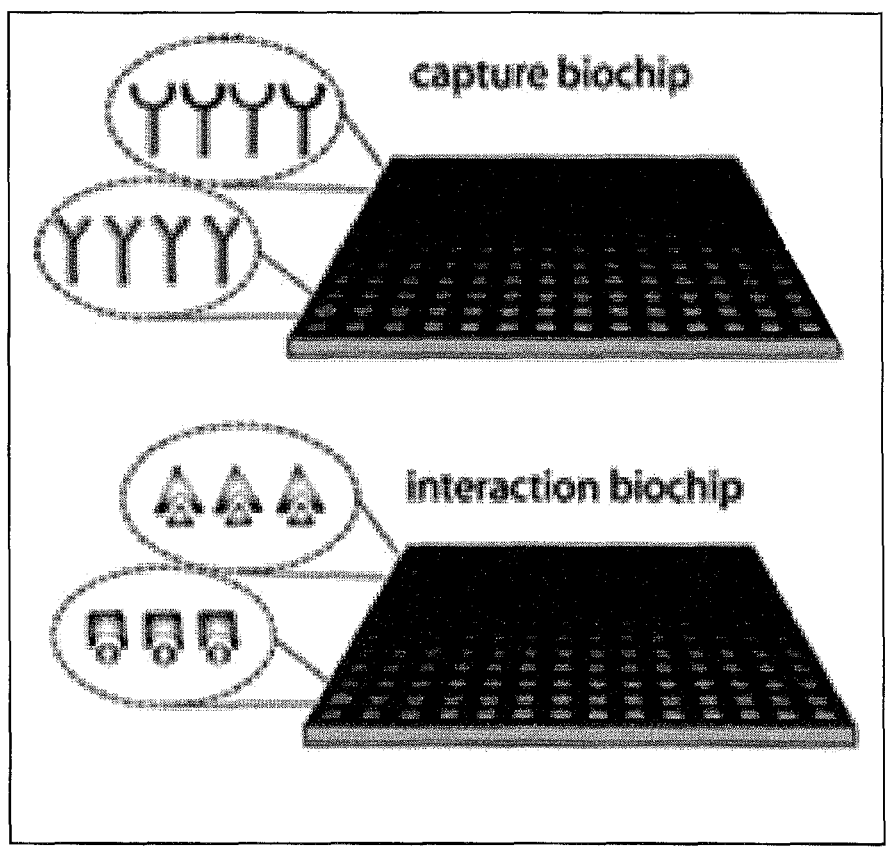

Unlike DNA microarrays [Schulze and Downward (2001) Nat Cell Biol 3: E190-5.], where oligonucleotide probes for each expressed gene can be readily synthesized, creating a purified set of arrayed cellular proteins or antibodies (as shown in FIG. 20) is significantly more difficult. This process involves the production of tens of thousands of recombinant proteins using gene cloning, in vivo cellular expression, protein purification and mechanical microarray printing [MacBeath and Schreiber (2000) Science 289: 1760-3.; Zhu, Bilgin et al. (2001) Science 293: 2101-5]. These methods are often slow, labor intensive and heavily dependent on highly specialized robotics, such as serial microarray printers/spotters which are expensive and subject to failure; the net result is prohibitively expensive protein arrays of limited density and limited scalability for larger protein content.

For example, Invitrogen has introduced the first commercial human proteome microarray [Zhu, Bilgin et al. (2001) Science 293: 2101-5]. It contains roughly 9,000 distinct proteins, representing a small fraction of the predicted human proteome [Melton (2004) Nature 429: 101-7], at a cost of $1,725/microarray (~$0.2/protein). While costs may come down as more efficient methods of protein production and isolation are introduced, fundamental limitations still remain—namely the need for individually cloning each gene, individually expressing each protein in cells, separate isolation of each protein, mechanical microarray printing of the proteins, stability of the protein stocks or arrays derived from them and difficulties in expressing proteins that are toxic to the host cell. Furthermore, at ~20,000 spots total (replicates and controls), Invitrogen's microarray capacity is nearly at it's maximum since protein arrays are not compatible with the photolithography used in DNA microarrays to create smaller and more densely packed spots. A 2005 review in Nature Biotechnology finds that "Invitrogen's recent launch of what it billed as the world's first commercially available human protein microarray may, paradoxically, signal the abandonment, for now at least, of the grand ambition of characterizing the entire human proteome using a single chip" [Sheridan (2005) Nat Biotechnol 23: 3-4]. Instead, the report contends, protein chip companies are focusing on selected microarray content (smaller protein subsets), custom tailored to specific applications.

An additional limitation of the current generation of proteomic arrays is the intrinsic low sensitivity and high noise which impedes biomarker discovery from clinical samples. Part of this problem derives from the low replicate number (duplicate) for each protein represented and the variability of spot printing and subsequent readout. In particular, conventional arrays are fabricated by printing and drying thousands of 100 micron protein spots on a flat surface (e.g. nitrocellulose film). The protein antibody interaction than occurs on top of this aggregated protein spot which is then again dried for read-out. For these reasons, the assay conditions are far from the ideal solution-phase functional assays. Ideally, proteins need to be arrayed in small "reaction vessels" where the protein-antibody interaction occurs and is measured. However, this is difficult, if not impossible to achieve using conventional protein microarray technology.

B.4.2 Cell-Free Expression-Based Proteome Arrays

Until recently, relatively high costs and low yields have discouraged the use of cell-free (in vitro) protein expression systems in the field of proteomics. However, recent improvements in this field hold great promise for solving many of the problems associated with conventional proteomic arrays [Rothschild and Gite (1999) Curr Opin Biotechnol 10: 64-70; He and Taussig (2001) Nucleic Acids Res 29: E73-3; Kawahashi, Doi, Takashima, Tsuda, Oishi, Oyama, Yonezawa, Miyamoto-Sato and Yanagawa (2003) Proteomics 3: 1236-43; Ramachandran, Hainsworth et al. (2004) Science 305: 86-90; Gite, Lim and Rothschild (2006) Biotechnology & Genetic Engineering Reviews 22: 151-169]. Advantages and improvements include: On-Demand Expression: Express specific proteins, on-demand, typically in <1 hr, even in eukaryotic (e.g. mammalian or insect) systems using a single facile reaction (e.g. Promega's batch mode rabbit reticulocyte or insect cell coupled transcription/translation system; Promega Corporation, Madison, Wis.). Recently, over 13,000 different proteins from the human genome were expressed using an improved cell-free wheat germ expression system demonstrating the feasibility of using cell-free techniques for a proteome factory [Goshima, Kawamura et al. (2008) Nat Methods 5: 1011-7]. High Yield: New "continuous exchange" cell-free (CECF) expression systems capable of ~1 mg/mL yields (e.g. Roche's Wheat Germ CECF; (Roche Applied Science, Indianapolis, Ind.)). Protein Compatibility: Often cellular systems cannot express proteins due to the cytotoxicity or interference with host cell physiology [Henrich, Lubitz and Plapp (1982) Mol Gen Genet 185: 493-7; Goff and Goldberg (1987) J Biol Chem 262: 4508-15; Nakano and Yamane (1998) Biotechnol Adv 16: 367-84; He and Taussig (2001) Nucleic Acids Res 29: E73-3; Endo and Sawasadki (2003) Biotechnol Adv 21: 695-713]. Membrane Proteins: Normal expression of these proteins in cells is not easily compatible with microarray technology since membrane proteins have to be isolated in detergent and reconstituted in model lipid bilayer systems. However, recently progress in cell-free protein techniques has made it possible to incorporate membrane proteins in a single step into nanolipoparticles [Cappuccio, Blanchette et al. (2008) Mol Cell Proteomics 7: 2246-53; Katzen, Fletcher et al. (2008) J Proteome Res 7: 3535-42; Cappuccio, Hinz et al. (2009) Methods Mol Biol 498: 273-96], small discoidal membranes mimicking the native membrane protein environment. In addition, commercial kits such as the Invitrogen MembraneMAX™ cell-free protein expression kits are available (Invitrogen, Carlsbad, Calif.).

B.4.3 Application of Reverse Proteomics and Proteome Microarrays to Autoantigen Discovery in Cancers and Autoimmune Diseases Autoimmune:

More than 80 illnesses have been described that are associated with activation of auto-reactive lymphocytes and the production of autoantibodies directed against normal tissue or cellular components (autoantigens) [von Muhlen and Tan (1995) Semin Arthritis Rheum 24: 323-58; Mellors (2002) 2005]. Collectively referred to as autoimmune diseases, they afflict an estimated 15-24 million people (at least 3-5%) in the U.S. and constitute a major economic and health burden [Jacobson, Gange, Rose and Graham (1997) Clin Immunol Immunopathol 84: 223-43]. A host of common diseases fall into this category including multiple sclerosis (MS), rheumatoid arthritis (RA), systemic lupus erythematosus (SLE), Sjögrens Syndrome (SjS), insulin-dependent diabetes (IDDM), myasthenia gravis (MG), psoriasis, scleroderma and primary biliary cirrhosis (PBC) [Mellors (2002) 2005].

The root causes of the immune dysfunction underpinning autoimmune disease are still not well understood. Consequently, autoimmune diseases generally remain difficult to diagnose based on clinical presentation, which typically involves a constellation of symptoms. The ability to detect serum autoantibodies greatly facilitates the diagnosis of autoimmune diseases. In the past, patient serum was screened for autoantibodies by indirect immunofluorescence (IIF) using a human cell line (Hep-2) as substrate. In recent years, national clinical laboratories have abandoned screening for autoantibodies by IIF and have switched to solid-phase assays. These assays, which include ELISAs and multiplexed bead-based platform technologies (e.g. Luminex Corporation, Austin, Tex.), use a limited number of purified native or recombinant antigens to screen for autoantibodies (termed here bait molecules as opposed to serum antibodies which are termed prey molecules). The rationale for the change to solid-phase assays is that these tests can be automated, significantly reducing labor costs. Furthermore, these assays produce quantitative and hence objective results, as opposed to the subjective nature of IIF.

The American College of Rheumatology recently convened an Ad Hoc committee to investigate whether screening for autoantibodies using solid phase assays is equivalent to screening for these antibodies using indirect immunofluorescence (http://www.rheumatology.org/publications/position/ana_position_stmt.pdf). After careful review of the available scientific literature, the committee determined that solid phase assays are not equivalent to IIF. The committee noted that the Hep-2 cell substrate contains more than 100 clinically-relevant autoantigens. In contrast, solid phase assays contain only a limited number of antigens. For example, the AtheNA™ anti-nuclear autoantibody (ANA) assay (Zeus Scientific, Branchburg, N.J.) based on the Luminex platform, screens for antibodies directed against only 14 nuclear autoantigens. Because the Hep-2 cell substrate and indirect immunofluorescence detects a larger number of autoantibodies, the committee concluded that solid phase assays, as they exist today, can not be used as a substitute for IIF to screen for autoantibodies.

For example, the limitations of solid phase assays for the detection of SLE-related autoantibodies were recently illustrated in a Case Record published in the New England Journal of Medicine [Kroshinsky, Kay and Nazarian (2009) N Engl J Med 361: 2166-76]. The appropriate diagnosis of SLE in the patient was significantly delayed because autoantibodies were not detected by the AtheNA™ Luminex assay. However; antinuclear antibodies were detected at high titer in the patient serum by IIF using the Hep-2 cell substrate.

Screening for autoantibodies by solid phase assays is significantly faster and more cost-effective than screening tests that rely on IIF. However, as described above, solid-phase assays contain far fewer autoantigens than are present in the Hep-2 cell substrate. Many of the autoantigens present in Hep-2 cells have not yet been characterized. To improve the sensitivity of solid phase assays, additional clinically-relevant autoantigens will have to be identified produced, purified and included in future solid phase assay kits.

Cancer:

In cancer, a growing body of evidence indicates [Chapman, Murray, McElveen, Sahin, Luxemburger, Tureci, Wiewrodt, Barnes and Robertson (2008) Thorax 63: 228-33] that autoantibodies form against tumor-associated autoantigens (TAA) and that these autoantibodies are present even in the early stages of disease.

There have been numerous reports which demonstrate the importance of TAA discovery for an immunological approach to cancer diagnostics. For example, a recent study on TAA for non-small and small-cell lung cancer [Chapman, Murray at al. (2008) Thorax 63: 228-33] reported that at least 1 antibody was detected out of a panel of 7 antigens in 76% of patients studied with 92% specificity. Since selection of the panel was based only on a small subset of proteins associated with cancer (p53, c-myc, HER2, NY-ESO-1, CAGE, MUC1 and GBU45) a more global proteomic approach is expected to lead to more sensitive and specific signatures. For example, in the case of heptocellular carcinoma (HCC), the use of serological proteome analysis (SERPA) led to a panel of 6 antigens which gave a sensitivity of 90% [Li, Chen, Yu, Li and Wang (2008) J Proteome Res 7: 611-20]. In the case of ovarian cancer, over 50 putative autoantigens involved in both a humoral and cell-mediated immune response were identified using a proteomic mass spectrometric approach [Philip, Murthy, Krakover, Sinnathamby, Zerfass, Keller and Philip (2007) J Proteome Res 6: 2509-17].

Reverse Proteomics in Autoantigen Discovery:

Proteomics and proteome microarrays in particular are ideally suited for the discovery of novel diagnostic autoantigen biomarkers for both cancers and autoimmune diseases. Small volumes of patient blood, plasma or serum samples are rapidly screened for autoantibodies, in unbiased fashion, against a large fraction of the human proteome present in an addressable chip in highly purified form. W. H. Robinson and P. J. Utz have done extensive work in this field using medium density protein arrays with a variety of autoimmune disorders. In addition to diagnosis, autoantigen biomarkers can be used for prognosis, disease staging and to assist in the development of tolerizing therapies [Robinson, DiGennaro et al. (2002) Nat Med 8: 295-301; Robinson, Garren, Utz and Steinman (2002) Clin Immunol 103: 7-12; Robinson, Steinman and Utz (2002) Arthritis Rheum 46: 885-93; Robinson, Fontoura et al, (2003) Nat Biotechnol 21: 1033-9; Graham, Robinson, Steinman and Utz (2004) Autoimmunity 37: 269-72]. Partial proteome microarrays have also been used for the discovery of TAA in colorectal cancer [Babel, Barderas et al. (2009) Mol Cell Proteomics 8: 2382-95], ovarian cancer [Hudson, Pozdnyakova et al. (2007) Proc Natl Acad Sci USA 104: 17494-9] and breast cancer [Anderson, Ramachandran at al. (2008) J Proteome Res]. The current invention will greatly facilitate and accelerate these goals by providing a faster, more flexible, less expensive and more robust method of producing and assaying protein and proteome arrays and with a greater scalability to true proteome-wide screening.

The following are examples of some of the many autoimmune diseases and cancers whose diagnosis, treatment and management may benefit from proteomics based autoantigen discovery.

Examples of Autoimmune Diseases:

Primary Biliary Cirrhosis:

PBC is an autoimmune disease characterized by the gradual progressive destruction of intrahepatic biliary ductules leading to hepatic fibrosis and liver failure (reviewed in [Kaplan (1996) N Engl J Med 335: 1570-80; Kaplan (2002) Gastroenterology 123: 1392-4; Talwalkar and Lindor (2003) Lancet 362: 53-61]). It is the third leading indication for liver transplantation. Diagnosis of PBC is currently achieved by abnormal liver function tests, antimitochondrial antibodies (AMAs) and characteristic histological findings in a liver biopsy specimen [Yang, Yu, Nakajima, Neuberg, Lindor and Bloch (2004) Clin Gastroenterol Hepatol 2: 1116-22]. However, initial PBC diagnosis is often missed because of the many vague and diffuse presenting symptoms which are characteristic of many other autoimmune diseases [Bloch, Yu, Yang, Graeme-Cook, Lindor, Viswanathan, Bloch and Nakajima (2005) J Rheumatol 32: 477-83]. Although AMAs are a sensitive and specific marker for this disease, the test may not be ordered in many patients, especially when the patient presents with vague symptoms of joint discomfort. In addition, even when AMAs are present, their titer is highly variable and the titer does not predict disease severity or prognosis [Leung, Coppel, Ansari, Munoz and Gershwin (1997) Semin Liver Dis 17: 61-9].

Systemic Lupus Erythematosus:

Systemic lupus erythematosus (SLE) is a chronic and potentially life-threatening autoimmune disease characterized by multiple organ involvement [Sherer, Gorstein, Fritzler and Shoenfeld (2004) Semin Arthritis Rheum 34: 501-37]. SLE afflicts 300,000 to 1.5 million people in the U.S., with 16,000 new cases/year [2009; Ward (2004) J Womens Health (Larchmt) 13: 713-8; Chakravarty, Bush, Manzi, Clarke and Ward (2007) Arthritis Rheum 56; 2092-4]. SLE affects primarily women in their child-bearing years, and is 9-fold more prevalent in women than men. The 10 year survival rate of this disease is 80-90%, with approximately 1,300 deaths per year. During 1979-1998, the annual number of deaths from lupus rose from 879 to 1,406 [(2002) MMWR Morb Mortal Wkly Rep 51: 371-4].

For the past several decades, indirect immunofluorescence (IIF), especially of the nucleus, has been the method of choice by physicians for the detection of autoantibodies present in the serum of autoimmune patients with SLE. Importantly, it remains the gold standard for anti-nuclear autoantibody (ANA) testing, including for SLE. Patient serum is serial diluted in two-fold increments and allowed to bind to a HEp-2 liver cell substrate on a microscope slide, which is then fluorescently stained to detect bound autoantibodies and examined under the microscope by a trained technician to identify the cellular staining patterns. However, this assay is problematic, as it is difficult to standardize owing to variations in the substrate and fixation process, variations in the microscopy apparatus, and due to the highly subjective interpretation of results [Jaskowski, Schroder, Martins, Mouritsen, Litwin and Hill (1996) Am J Clin Pathol 105: 468-73]. Furthermore, this approach is slow, laborious and not amenable to high throughput automation [Ulvestad, Kanestrom, Madland, Thomassen, Haga and Vollset (2000) Scand J Immunol 52: 309-15]. This lack of throughput is compounded by the fact that the diffuse presenting symptoms of SLE causes doctors to often indiscriminately order IIF ANA tests, wasting precious bandwidth [Suresh (2007) Br J Hosp Med (Lond) 68: 538-41].

Sjögren's Syndrome:

Sjögren's (pSjS) is an autoimmune disease characterized by chronic inflammation of the lacrimal and salivary glands, resulting in the hallmark symptoms of dry eyes and mouth. It considered the second most common autoimmune disease next to rheumatoid arthritis, however, most cases remain undiagnosed [Al-Hashimi (2007) Womens Health (Lond Engl) 3: 107-22]. The disease is differentiated between primary and secondary Sjogren's (pSjS and sSjS), whereby gland inflammation does not or does occur in the presence of another connective tissue disease, such as rheumatoid arthritis, systemic lupus erythematosus, primary biliary cirrhosis or scleroderma [Vitali, Bombardieri et al. (2002) Ann Rheum Dis 61: 554-8; Manoussakis (2004) Orphanet encyclopedia]. It is estimated that pSjS affects 1 to 4 million people in the United States. The disease affects predominantly women (90% of SjS patients) in the post-menopausal years (40-50), although people of any age can develop the disease [Pillemer, Matteson, Jacobsson, Martens, Melton, O'Fallon and Fox (2001) Mayo Clin Proc 76: 593-9; Manoussakis (2004) Orphanet encyclopedia; Alamanos, Tsifetaki, Voulgari, Venetsanopoulou, Siozos and Drosos (2006) Rheumatology (Oxford) 45: 187-91]. Misdiagnosis/underdiagnosis is primarily due to the wide range of often vague clinical manifestations which overlap with a broad spectrum of other autoimmune disorders. While ANAs directed against the Ro/La RNP complex (SSA 52 kDa Ro, SSA 60 kDa Ro and SSB La) are the most common autoantibodies in SjS, they are also present in other autoimmune diseases, especially SLE [Mahler (2007) Current Rheumatology Reviews 3: 67-78].

Example of Cancer Diseases:

There exists an urgent need to develop an effective non-invasive method of detecting colorectal cancer (CRC), the second leading cause of cancer deaths in the U.S. and Western world. The American Cancer Society estimates that there will be approximately 150,000 new cases of colorectal cancer (CRC) and 56,000 CRC related deaths per year. The life-time risk of colorectal adenocarcinoma is 6%, with it rising steeply at ages over 60 [Davies, Miller and Coleman (2005) Nat Rev Cancer 5: 199-209]. Such non-invasive testing, if instituted for a large segment of the population, could result in a dramatic reduction in the mortality due to this disease. The American Cancer Society recommends that individuals over the age of fifty with normal risk be screened at 1-5 year intervals using one or more of the current methods for early CRC detection, which include the fecal occult-blood test (FOBT) and endoscopic colorectal examination (colonoscopy). However, these methods are of limited effectiveness, compliance and/or capacity to handle population-wide screening.

In contrast, as described above, TAA hold significant promise for early non-invasive diagnosis of cancers such as CRC, especially if a panel of TAA with high specificity could be developed. However, relatively fewer TAA have been identified and validated thus far for CRC compared to other cancers, such as ovarian and lung (see above). In one study, the use of SEREX (serological identification of antigens by recombinant expression cloning) resulted in the identification of 8 different potential clones for TAA, three of which (C21ORF2, EPRS and NAP1L1) were found mainly in cancer patients' sera [Line, Slucka, Stengrevics, Silina, Li and Rees (2002) Cancer Immunol Immunother 51: 574-82]. WT1, which has been shown to be overexpressed, stimulates cytotoxic T-cells making it a candidate for anti-CRC-vaccine development [Koesters, Linnebacher, Coy, Germann, Schwitalle, Findeisen and von Knebel Doeberitz (2004) Int J Cancer 109: 385-92]. Other TAA associated with CRC include colorectal tumor-associated antigen-1 (COA-1) [Maccalli, Li, El-Gamil, Rosenberg and Robbins (2003) Cancer Res 63: 6735-43], tumor-associated antigen 90K/Mac-2-binding protein [Ulmer, Keeler, Loh, Chibbar, Torlakovic, Andre, Gabius and Laferte (2006) J Cell Biochem 98: 1351-66] and tumor-associated antigen TLP [Guadagni, Graziano, Roselli, Mariotti, Bernard, Sinibaldi-Vallebona, Rasi and Garaci (1999) Am J Pathol 154: 993-9].

SUMMARY OF THE INVENTION

A New Approach to Proteomics

One embodiment of this invention provides a novel, rapid and quantitative approach for global proteomic screening based on Matrix Assisted Laser Desorption Ionization Time-of-Flight Mass Spectrometry (MALDI-TOF MS) scanning/imaging performed on a random protein-bead array. This approach, termed by us as bead-based global proteomic screening (Bead-GPS), utilizes photocleavable mass tags to code both a protein library ("bait" molecules) displayed on individual beads randomly arrayed in an array substrate such as a pico-well plate. Bead-GPS also uses a library of probe ("prey") molecules such as proteins, nucleic acids and even complex biological samples such as serum from patients containing serum antibodies or cell lysates, which are mixed with (i.e. used to query) the protein-bead array. Because we have shown that MALDI-TOF MS can detect multiple mass tags from an individual bead that has both the bait (e.g. protein) and probe (prey) molecules attached, it is possible to rapidly identify all the interactions which occur among the millions of possible interactions in the proteome. In addition, the ability to perform a fluorescent scan, either before or after MALDI-TOF MS scanning or imaging, on the same random bead-protein array (FIG. 21), provides additional information about the position of beads in the array displaying positive interactions between bait and prey and also information about the strength of these interactions.

An additional embodiment of this invention involves rapid scanning of a random array of beads for potential beads which exhibit specific interact of the bait molecule residing on the bead and attached through a binding agent (e.g. bait molecule is a specific autoantigen bound to bead surface through an antibody binding agent) with a prey molecule (e.g. autoantibodies from a patients blood) which interacts with said bait molecule. Beads displaying positive interactions between autoantigens and autoantibodies are first identified on the basis of detection of fluorescence from a fluorpophore which is directly or indirectly linked to the prey molecule through a binding agent and then the identity of the bait molecules residing on the bead determined by decoding the identity of bead using a coding agent such as a mass tag. Two different methods of decoding positive beads (e.g. positive-hits) in the bead array are based on: i) MALDI-TOF scanning/imaging of individual beads, containing mass tags which in some cases are photocleavable (PC) mass tags, the beads being randomly arrayed on a specially designed pico-well slide containing ½-million wells in the dimensions of a standard microscope slide or ii) Massively parallel RT-PCR or hybridization-based DNA/RNA microarray using photocleavable nucleic acid-tags (such as photocleavable DNA-tags). In either case, the aqueous environment provided for interaction between bait and prey (probe), the high number of replicate beads for each bead species in the total library, plus the higher binding capacity per bead compared to conventional microarrays provides significant improvements in the biomarker discovery process compared to conventional methods.

Bead-GPS can be readily adapted to a number of useful applications in proteomics, biomarker discovery and biomolecular profiling. This includes:

High Throughput Screening of a Drug Library Against a Proteomic Library:

It is of great value in the pharmaceutical industry to screen the binding of a small molecule compound library which can serve as potential therapeutic drugs against a range of protein molecules or other biologically active molecules such as nucleic acids. In this embodiment all compounds in the drug library (i.e. prey molecules) which bind to a particular protein (bait molecule) residing on a particular bead can be identified by subjecting the individual beads to MALDI-MS and determining the unique mass and fragmentation pattern of the drug compound(s). Thus in this embodiment the drug molecule serves on its own as a unique mass-tag which can be distinguished from other mass tags. This is an especially useful approach since drug compounds in such a library are often characterized by mass spectrometry during their synthesis and purification. As demonstrated by the recent study performed using the industry-standard 384-well plate and MALDI triple quadrupole mass spectrometry [Rapid Commun Mass Spectrom. 2009 Oct. 30; 23(20):3293-300. "Extending matrix-assisted laser desorption/ionization triple quadrupole mass spectrometry enzyme screening assays to targets with small molecule substrates" Rathore R, Corr J J, Lebre D T, Seibel W L, Greis K D], such approach is feasible. Yet, compared to the 384-well design, the bead-based screening offers a significant improvement in sample throughput as hundreds of thousands proteins can be assayed on a single slide [MacBeath and Schreiber (2000) Science 289: 1760-3.].

Global Protein Expression Profiling:

Expression profiling of specific proteins in a particular complex mixture such as a biological fluid or tissue or a cell culture is extremely important in current biothedical research. In this application the various proteins in the sample whose expression level is to be measured is considered the prey molecules whereas specific antibodies immobilized on beads which could potential bind to the proteins in the sample are considered the bait molecules. In this embodiment, different samples whose protein expression level are to be compared are labeled with different photocleavable (PC) isotope coded mass tags. Such mass tags for example could comprise photocleavable peptides with identical sequences but containing different isotopes labels which thereby result in different masses for each photocleavable polypeptide. The labeled sample is then incubated with an antibody-bead library which is encoded using PC-mass tags. The relative expression level of specific proteins in the sample for which there are cognate antibody-beads in the library can then be determined similar to the use of printed antibody microarrays with a fluorescent read-out. In one embodiment, the comparison of expression level of proteins between two or more samples is performed by (i) direct labeling of all proteins in the sample with a PC-mass tag reactive towards, for example, primary amine or sulfhydryl groups in the protein. The PC-mass tags have an identical peptide sequence but variable molecular weight achieved by incorporation of isotope-labeled amino acids at specific positions; (ii) Capturing individual proteins on antibody-coated beads, which are also coded using a set of PC mass tags; (iii) Distributing beads into individual wells on a pico-plate and eluting the PC mass tags by UV-irradiation and application of MALDI matrix; and (iv) measuring relative intensity of isotope-labeled mass tags for each of the antibody beads.

Massively Parallel Multi-Analyte Analysis:

The concentration of a large number of analytes in a biological or clinical sample (e.g. prey molecules) including hormones, cytokines and other bio-molecules can be determined similar to other bead-based multiplex assays such as the Luminex xMAP® technology based on fluorescent flow-cytometry. However, compared to Luminex which is limited to only 100 analytes, Bead-GPS allows a much larger number to be detected due to the virtually unlimited number of combinations of mass tags available to code the bait molecules which are immobilized on beads.

Global Functional Screening:

In one embodiment of this invention, the effects active biomolecules (e.g. prey molecules) on a library of a mass-tagged protein-bead library (bait molecules) can be determined. Such global functional screening is extremely useful in biomedical applications where the effects and specificity of a particular functional molecule such as a kinase is to be determined for a library of different proteins. For example, a single kinase, proteases, methylases, phosphorylases or mixtures of these molecules can be contacted with the entire bead library either before or after it is arrayed and alterations in the bait molecule residing on individual beads along with the identity of the bait molecule determined using MALDI-MS. This is possible because of MALDI-MS and related techniques such as MALDI-MS-MS to detect, at the level of individual amino acids, modifications such as phosphorylation, ubiquitination or methylation. Because each bead also contains a unique photocleavable mass tag the identity of the bait protein residing on the bead can be uniquely determined. In this application it is to be noted that the prey molecules do not need to remain bound to the bait molecules but may only transiently interact to produce an alteration in the bait molecule. It should be also noted that in this application detection of the interaction of prey molecules with the bait molecules is possible because of the alteration the prey molecule produces on the bait molecule.

Key Elements of the Present Invention

MALDI-TOF MS Imaging/Scanning of Individual Beads in an Array: MALDI-TOF MS spectra are recorded of molecules such as proteins, polypeptides, antibodies or nucleic acids attached directly or indirectly to individual beads by directly exposing the beads to the MALDI-TOF MS laser beam and analyzing by mass spectrometry the molecules that enter the mass spectrometer (heretofore referred to a MALDI-TOF MS imaging of beads). MALDI-TOF MS bead imaging of multiple beads is accomplished by scanning over an area of the MALDI-TOF MS substrate plate in small steps to allow sufficiently high special resolution to measure individual beads. While examples of beads used in MALDI-TOF MS imaging given for this invention ranged in size from 34-150 microns in diameter and consisted of agarose beads, it is to be understood that this invention could also apply to larger or smaller beads of different composition. For example, smaller size beads could be analyzed using a commercially available Bruker UltraflexTreme (Bruker Daltronics) which features a 10 micron focused laser for MALDI-TOF MS. In addition, various software programs allow high resolution (<100 microns) to be achieved using instruments with only a 100 micron beam diameter, by interpolating data from steps smaller than 100 microns. Although Time-of-Flight (TOF) MALDI mass spectrometry is the preferred method of analysis in this invention, related techniques, such as MALDI triple quadrupole (MALDI-QqQ) mass spectrometry or Fourier transform MS can be used as well.

Bead-Sorted Libraries of in vitro Expressed Proteins (BS-LIVE-PRO):

BS-LIVE-PRO are rapidly produced by expressing each protein separately in cell-free translation reactions and then binding the expressed protein through an affinity tag to coated beads. Alternatively, single molecule solid-phase PCR technology (e.g. emulsion PCR) is used to create a Bead-Sorted Library of in vitro Expressible DNA (BS-LIVE-DNA) in single reaction and the beads then cell-free expressed into a BS-LIVE-PRO in a single reaction whereby nascent proteins are captured onto their cognate DNA-containing bead. Advances in cell-free translation technology including tRNA mediated protein engineering developed by AmberGen make it possible to engineer these protein libraries for optimal proteomic screening [Gite, Mamaev, Olejnik and Rothschild (2000) Anal Biochem 279: 218-25; Gite, Lim, Carlson, Olejnik, Zehnbauer and Rothschild (2003) Nat Biotechnol 21: 194-7; Mamaev, Olejnik, Olejnik and Rothschild (2004) Anal Biochem 326: 25-32;

Olejnik, Gite, Mamaev and Rothschild (2005) Methods 36: 252-60; Gite, Lim et al. (2006) Biotechnology & Genetic Engineering Reviews 22: 151-169].

Specially Designed Pico-Well Plates Suitable for MALDI-MS and Fluorescence Scanning:

We have developed a novel substrate consisting of a slide with ½ million individual etched wells in the dimensions of a standard microscope slide, in order to randomly array the bead library with one bead per well. Both MALDI-MS and fluorescence scanning can be used to rapidly image each individual bead in the array to detect positive biomarker hits along the identity of the protein on the beads by using mass tags. Increased sensitivity is obtained by using a thin layer of gold coating to neutralize charge on plate. Dimensions of the wells can be selected to control for different size beads (diameter of well) in addition to how far bead is exposed above slide surface (depth of well). This control is extremely to obtain optimal results such as high resolution MALDI MS Image scans.

Photocleavable Mass Tags:

The identity of each bait molecule such as a protein on a specific bead in the randomly arrayed library of beads as well as positive biomarker hits based on binding of an interacting molecule (prey molecule), such as an antibody, small molecule drug candidate, or other biomolecule, are rapidly identified by using AmberGen's photocleavable (PC) mass tags which are protected by over 10 U.S. patents [e.g. U.S. Pat. Nos. 5,948,624; 5,986,076; 6,589,736; 7,312,038; 7,339,045; 7,211,394; 6,057,096; 6,218,530; 7,057,031; 7,195,874; 7,485,427; 7,547,530]. Each PC-mass tag consists of a polypeptide with a unique sequence and mass, attached through a photocleavable linker to the bead or probe (prey), which are read by MALDI-MS. Adding a PC-mass tag to the probe (prey), such as a crude biological sample, allows "bar-coding" of a particular sample so multiple samples can be simultaneously measured, Beads can also be encoded for specific samples by using mass tags.

Photocleavable DNA Tags:

Photocleavable DNA tags provide a second method of decoding beads and rapidly identifying biomarker hits. These tags consist of a unique DNA sequence linked to the bead, bait or prey molecules through a proprietary photocleavable phosphoramidite developed by AmberGen and marketed by Glen Research (Sterling, Va.).

Selective Removal of Photocleavable Mass Tags or DNA Tags from Positive Beads:

In addition to decoding of individual beads using MALDI-MS bead imaging, positive beads (beads exhibiting an interaction between the attached bait molecules and prey molecules) can be decoded by selective photocleavage of the mass tags. For example, a conventional fluorescence scanner can be modified to include a laser with excitation wavelength and intensity sufficient to photocleave mass tags or DNA tags from the beads when the fluorescent scan detects a positive hit (interaction). For example, such a device would allow collection of all mass tags or DNA tags from positive beads in a bead array such that the tags could then be analyzed with an appropriate reading device. In the case of mass tags, the entire set of selectively removed mass tags could be read using a conventional (non-scanning) mass spectrometer in a single measurement. Similarly, the DNA tags could be read using an RT-PCR device containing suitable probes for each DNA tag or by using massively-parallel sequencing of individual DNA tags. The advantage of this approach is that a single measurement allows all positive beads in bead array to be identified.

Fluorescence and MALDI MS Image Synchronization for Bead Selection:

An important feature of one embodiment of this invention is the ability to synchronize the fluorescent scan with the MALDI-MS decoding thereby reducing the number of beads which need to be scanned by MALDI-MS. In order to improve accuracy, synchronization beads consisting of a fluorescent label and unique mass tag can be added in the random bead array. Such synchronization beads allow more accurate registration of the fluorescence and MALDI images. In addition to pico-wells formed from fiber optic bundles, a photolithographic method of well fabrication can be utilized to increase accuracy of the position of each well.

Physical Bead Selection Prior to MALDI-MS Analysis or Imaging:

An alternative (or complement) to direct selection of positive hits (beads) by fluorescence imaging prior to MALDI-MS decoding is the use of physical methods to separate positive beads from negative beads. One such approach is the use of fluorescence activated cell-sorting (FACS) (see Experimental Example 11). A second method is use of a magnetic bead sorting techniques.

Although selection either by imaging or physical separation of positive hits (beads) prior to MALDI-MS decoding is the preferred method, it should be noted that it is not required. As demonstrated, mass tags can be used alone for both bead identification and autoantibody readout (see Experimental Examples). In this case, since hits are not pre-imaged by fluorescence, the entire library is imaged by MALDI-MS in the pico-well plates. Importantly, the newer generation of faster scanning MALDI-MS instruments can do this in a relatively short amount of time.

Mass Tags for Bead Decoding

Basic Concept: Once beads have been sorted or selected for positive "hits" on the basis of fluorescence scanning as described above, the next step in one embodiment of this invention is decoding the beads. We have developed a new method of decoding based on the use of photocleavable mass tags. In one embodiment of this invention, the mass tags evaluated are modified polypeptides whose sequence has been chosen so that its mass is unique (i.e. differs from every other mass tag used in the library). In a second embodiment, the mass tags are isotopically labeled polypeptides with the same sequence but different masses. In a third embodiment, the mass tags consist of a different polymer than a polypeptide such as an oligonucleotide. It is to be understood that in this invention there are a variety of molecules which would serve as mass tags and it is not limited to one class of molecule or polymer.

In principle, a relatively small peptide (e.g. an octamer, N=8) can provide sufficient number of sequences to provide sufficient unique masses to satisfy even a large library of 100,0000 different "bait" species ($20^N \approx 25 \times 10^9$), In practice, the number of viable sequences depends on the mass resolution of the MALDI-MS instrument which is often better than 0.1 daltons in the mass range measured. In addition, any degeneracy in the molecular weight of the mass tags can be decoded using the ability of MALDI-MS to sequence small peptides (<5,000 MW). Additional "fine-tuning" of masses can be accomplished by modification of the mass tag such as the addition of fluorescent labels.

Figure 22:
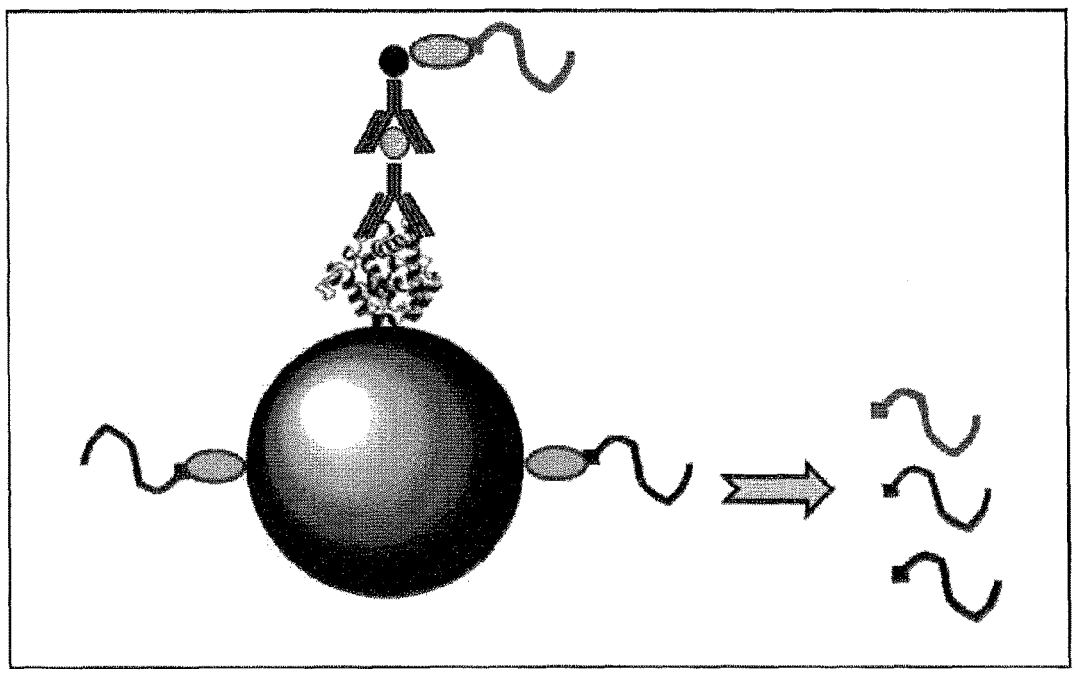

As shown in FIG. 22, multiple mass tags can be deployed on each bead to determine the identity of the attached protein (red), the sample being screened in cases where multiple samples are scanned (sometimes referred to as bar-coding) (purple) and the presence of an interacting probe or prey (e.g. antibody) indicating a positive hit or biomarker (green).

Since, as described above, beads can be pre-selected by fluorescence scanning on the pico-well slide, this last mass tag serves to reduce false-positives ensuring higher accuracy for biomarker selection.

Photocleavable Linkers

In some Experimental Examples shown in this patent, which used mass tags attached to beads for identification, the mass tags were not directly covalently linked to the bead surface but instead bound through an antibody-polypeptide interaction (e.g. Example 3). However, this is non-ideal since stringent wash steps could result in partial removal of the tags. One solution to this problem is to use covalently attached mass tags which are photo-released upon exposure to the proper light. Alternatively, a near-covalent strength linkage between (strept)avidin and biotin ($K_d=10^{-15}$) can be used in conjunction with a photocleavable linker.

AmberGen has developed a novel class of photocleavable linkers (PC-Linkers) useful in a variety of applications such as photocleavage assisted molecular purification, tRNA-mediated protein engineering, photo-activation of compounds, bio-molecules and viruses as well as photocleavable mass-tagging for multiplexed assays [Olejnik, Krzymanska-Olejnik and Rothschild (1996) Nucleic Acids Res 24: 361-6; Olejnik, Krzymanska-Olejnik and Rothschild (1998) Nucleic Acids Res 26: 3572-6; Olejnik, Ludemann et al. (1999) Nucleic Acids Res 27: 4626-31]. In the case of mass-tagging of the proteomic bead-library, a short peptide with 7 or 8 amino acids is linked to the beads via a photocleavable linker. Note that previous experiments have demonstrated that AmberGen's PC-Linker is rapidly photo-cleaved with 95% efficiency is less than 10 minutes using a low-intensity commercial black-light [Olejnik, Ludemann et al. (1999) Nucleic Acids Res 27: 4626-31].

Figure 23:
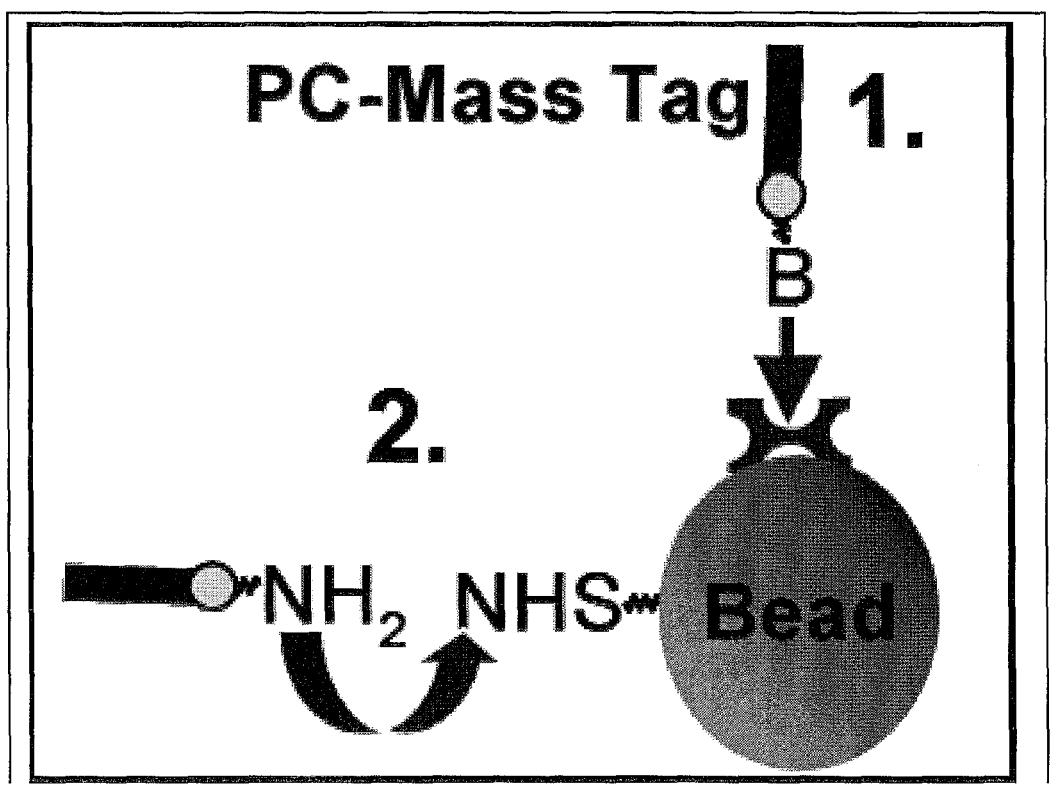

In one embodiment of the invention photocleavable (PC)-mass-tags for protein identification are attached to beads in one of two ways as illustrated in FIG. 23 and detailed below:

Ultra-High Affinity Biotin-(Strept)Avidin:

Peptide mass tags modified at the N-terminus, for example, with AmberGen's photocleavable biotin are attached to (strept)avidin coated beads. This mass-tagging method has already been demonstrated in the Experimental Examples (see Example 5).

Direct Covalent:

Peptide mass tags bearing an N-terminal photocleavable primary amine moiety can be chemically attached to beads. In the example in FIG. 23, NHS-activated (primary amine-reactive) beads are used for this procedure. This is highly analogous to AmberGen's phosphoramidite technology distributed through Glen Research (Sterling, Va.) for introducing a photocleavable primary amine at the 5' end of DNA [Olejnik, Krzymanska-Olejnik et al. (1998) Nucleic Acids Res 26: 3572-6]. Here, peptide mass tags lacking lysines (reactive primary amine on side chain), or where lysines are blocked on the ε-amine, will be used to avoid non-cleavable attachment to the amine-reactive beads.

In one embodiment for the production of PC-mass tag libraries, a library of peptides pre-screened by mass spectrometry can be commercially synthesized by available vendors such as Mimotopes (Austria), Peptide 2.0 Inc. (Chantilly, Va.) or GenScript Inc. (Piscataway, N.J.) and used to create the mass tags which will be photocleavably linked to the beads. High throughput peptide synthesis services are available from these vendors (e.g. soluble peptide arrays in 96-well plates) and peptides can be purchased with full HPLC and mass spectrometry quality controls. Conventional solid-phase chemical peptide synthesis begins at the C-terminus and ends at the N-terminus. The growing peptide is tethered to the solid-phase synthesis resin via its C-terminal carboxyl group, exposing its N-terminal amine (after deprotection) and allowing sequential attachment of another N-terminal blocked amino acid precursor (again followed by deprotection). Thus, the attachment of N-terminal modified PC-Biotin or PC-amine (amine protected) amino acid precursors at the final cycle of synthesis would be a relatively strait forward process.

We have estimated that due to the high analytical sensitivity of mass spectrometry (attomoles), even adding 10 fmoles per bead of mass tags (10-mer), the aforementioned peptides with N-terminal PC-Linker modification and all quality control data will add only pennies (¢10) to the cost of an entire proteome-bead library (e.g. at 500,000 beads/library). Note that data in the Experimental Examples has already shown that strong MALDI-TOF MS mass-imaging signal can be achieved when 5 fmoles/bead is added (5 fmoles maximum assuming 100% binding; see Example 5).

Figure 24:
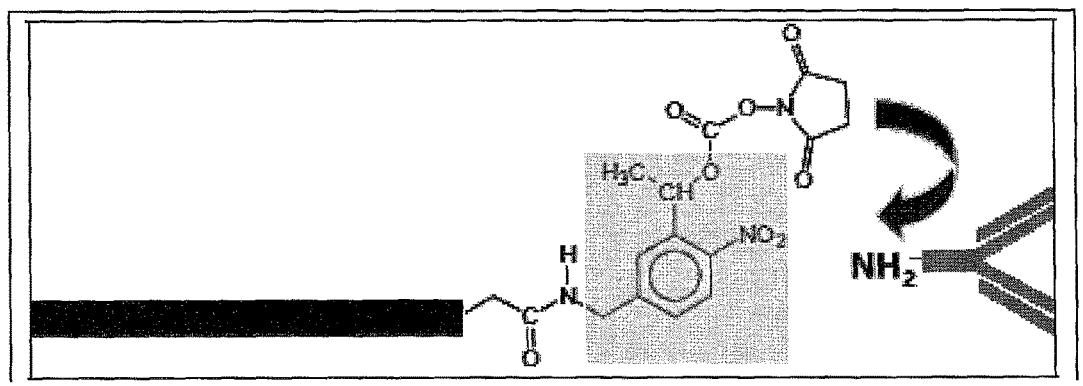

In addition to PC-mass tags attached to the beads for identification purposes, the present invention can utilize PC-mass tags attached to the probes used to query the bead library. In the example of using proteome bead-libraries for autoantigen discovery, the PC-mass tag is attached to the anti-[human IgG] secondary antibody probe used to detect the bound serum autoantibody. In this case, only one species of unique mass tag is required. This has already been experimentally demonstrated in Experimental Example 7. In one embodiment of the invention, custom reagents can be synthesized to allow direct covalent labeling of probes (e.g. antibodies) with PC-mass tags (FIG. 24).

MALDI-MS for Mass-Imaging of Individual Beads

An important feature of one embodiment of this invention is the ability of MALDI-MS to rapidly scan/image individual beads. In particular, we have demonstrated (see Examples) that MALDI-MS is capable of rapidly decoding PC-mass tags, including for example in conjunction with read-out antibodies (probes) to detect positive autoantibody interactions with protein autoantigens (bait) on beads. This capability to quantitatively measure, using mass spectrometry, molecules from individual beads offers many advantages not limited to just mass tag decoding, but also for direct identification of proteins and other bio-molecules residing on the bead surface or indirectly attached to the bead.

Instrumentation and Software

As an example of the ability of MALDI-MS to image individual beads, measurements were performed using an ABI 4800 Plus MALDI-TOF-TOF mass spectrometer (see Examples), although such measurements are not limited to this particular model of MALDI-TOF instrument. Typically, scanning is done using the ABI 4800 software in the positive ion reflector mode with internal calibration using 50-200 laser pulses per sample spot, which results in measurement times of ~0.25-1 s per bead.

In general, mass spectrometry and MALDI-MS in particular have proven to be highly amenable to high throughput applications in both clinical and basic research settings. For example, Sequenom Inc. (San Diego, Calif.) has established MALDI-MS as an effective technique in the field of genotype profiling, and is providing diagnostic products in this area. As a second example of automation of mass spectrometry in clinical diagnostics, the Pediatrix Medical Group (Sunrise, Fla.), the largest provider in the US for neonatal blood tests, uses tandem array mass spectrometry to detect metabolic disorders and has screened over 2 million babies using this method.

In the case of this invention, many improvements are envisioned which can facilitate automation and high throughput biomarker discovery. For example, multiplexing can be achieved at several stages including during the preparation of the bead library and in bar-coding multiple sample. Importantly, the use of a highly automated mass spectrometer such as the ABI 4800 Plus MALDI-TOF-TOF MS or the more advanced ABI 5800 will also facilitate high throughput analysis at the MALDI-MS bead scanning stage. For example, this system uses advanced software designed for automated scanning of a two-dimensional area, data collection and spectral processing. As an example, we already demonstrated the ability to automatically scan approximately 10,000 beads in the pico-well MALDI plate in one hour (see Examples). The use of the ABI 5800 should reduce this time to 1/10 (6 minutes). Furthermore, using one of the commercially available plate-loading robots will allow the use of the instrument in operator-free mode, 24-hours a day. As an example of automation levels achievable with MALDI-MS, Sequenom, Inc. has introduced a MALDI-based system for SNP analysis which is capable of analyzing 100,000 genotypes per day.

Finally, the MALDI-MS imaging of individual beads described in this invention requires software to analyze data and to identify mass tags on individual beads. There are a variety of software packages available both commercially and in the public domain for this purpose. As an example, we performed image acquisition and analysis using public domain software 4000 Series and BioMap software respectively (www.maldi-msi.org). BioMap is a powerful biomedical image analysis software package supporting various data types generated by optical, PET, CT and mass spectrometry based imaging. The BioMap platform allows visualization and storage of large volumes of data including experiment-specific information such as scan ID, experimental protocol and sample history. It is also a flexible tool that can be easily modified to accommodate a specific requirement. It is contemplated that as part of this invention, improved software for imaging of individual beads and mass tags can be made that is designed for a MALDI-MS bead-imaging workflow, such as automated co-registration of fluorescent and MALDI-MS scan images and identification of positive "hits" based on the detection of PC-mass tags.

Mass Tag Decoding

In general, a requirement of mass tag decoding is that each mass tag peak must correspond to the correct molecular weight predicted by the mass tag molecular structure, such as for example a given polypeptide sequence plus any modifications or isotope labeling, within the resolution of the spectrometer in the specific mass range (~0.1 Da in 600-4,000 Da range).

It is highly desirable that each mass tag peak must have a signal-to-noise ratio of at least 50:1, although lower signal-to-noise is sufficient for some applications. For comparison, the signal-to-noise ratio of single prototype mass tags attached to beads incorporated into arrays as described in the Experimental Examples are routinely >50:1 using a set of standard mass spectral parameters. Note that the signal-to-noise ratio in all experiments is determined using the ABI4800 software, which measures the integrated target peak intensity and ratios this to the integrated intensity of a nearby background region which exhibits no detectable peaks.

Importantly, spectral resolution and mass accuracy of the ABI 4800 Plus MALDI-TOF-TOF analyzer is sufficient to unambiguously identify peptides separated by as little as 0.1 Da. However, one potential problem is the appearance of several peaks for each peptide in the mass spectra, which are separated by 1 Da (the "isotope envelope"), due to the presence of small amounts of mass-shifted C13 and N15 atoms in the protein sequence. In the case of two mass tags separated by only a few Daltons, the spectral overlap may affect the tag identification. This will be addressed by using, in real-time, a spectral processing routine called peak de-isotoping. The routine, which is built-in into the ABI 4800 data acquisition software, replaces multiple peaks in the isotope envelope with a single mono-isotopic peak (corresponding to the sequence containing only C12 and N14 atoms).

In Situ Mass-Fingerprinting of Proteome Bead-Arrays

Rather than the addition of exogenous mass tags, or any other tags, it is possible to utilize the bead-bound bait molecules (e.g. recombinant proteins) themselves as identification codes. Analogous to mass spectrometry based on mass-fingerprinting used in classical proteomics, proteins are digested with protease (e.g. trypsin) and the resultant peptide "fingerprint" used for protein identification. If necessary, the peptides are further fragmented in the TOF/TOF tandem mass spectrometer and sequenced using the standard capabilities of today's instruments. Experimental Examples 8 and 9 demonstrate this capability in MALDI-MS bead imaging mode.

Photocleavable DNA Tags

In addition to peptide based decoding of a bead library, we have developed an alternative method of coding individual beads based on the use of photocleavable (PC)-DNA tags. Such tags are also based on proprietary photocleavage technology developed by AmberGen [U.S. Pat. Nos. 5,948, 624; 5,986,076; 6,589,736; 7,312,038; 7,339,045; 7,211, 394; 6,057,096; 6,218,530; 7,057,031; 7,195,874; 7,485, 427; 7,547,530] which offers convenient synthesis of DNA molecules with a 5'-modification consisting of a photocleavable linker such as PC-aminotag-phosphoramidites commercially distributed by Glen Research Inc. These tags can be directly linked to the activated beads similar to the method used for PC-mass tags and released upon exposure to near-UV light (see Experimental Examples). Once removed from individual positive beads, these PC-DNA tags can be rapidly decoded and quantified in bulk using a massively parallel PCR or sequencing platform. One embodiment of this is shown in Experimental Example 10. In addition, MALDI-MS bead imaging of PC-DNA tags from beads or particles is also possible.

Importantly, photocleavage from individual beads and collection of DNA tags (or mass tags) from positive beads can be easily accomplished almost simultaneous with fluorescent scanning by using a modified fluorescence microarray scanner. In particular, a laser normally used for scanning the image can be replaced with a laser capable of photocleavage of DNA tags from individual beads such as a pulsed Nd-Yag laser with 355 nm output which are widely commercially available at low cost. It has been demonstrated by us that such lasers can photocleave >90% of the tags on a bead sample in less than a few seconds. Since commercial fluorescent scanners operating with multiple wavelengths and different lasers are designed to perform sequential scans maintaining image registration, software image identification of positive beads would allow the Nd-Yag laser to be switched on to expose only positive beads during a sequential registered scan. Scan resolution is normally 3-5 microns, allowing high precision for Nd-Yag laser beam to photocleave DNA tags from 34 micceon beads located in the pico-well plate (beads used extensively in Experimental Examples). Alternatively, a scanner using a CCD imager along with a photocleaving laser can be readily used to selectively remove DNA tags from specific beads identified as positive in the fluorescent scan. Photocleaved DNA tags can be collected in a thin fluidic chamber overlaying the array for subsequent decoding. Importantly, selection of the positive hits is simplified for this approach since the imaging and photo-release are done simultaneously in the same instrument.

DETAILED DESCRIPTION OF THE INVENTION

Figure 25:
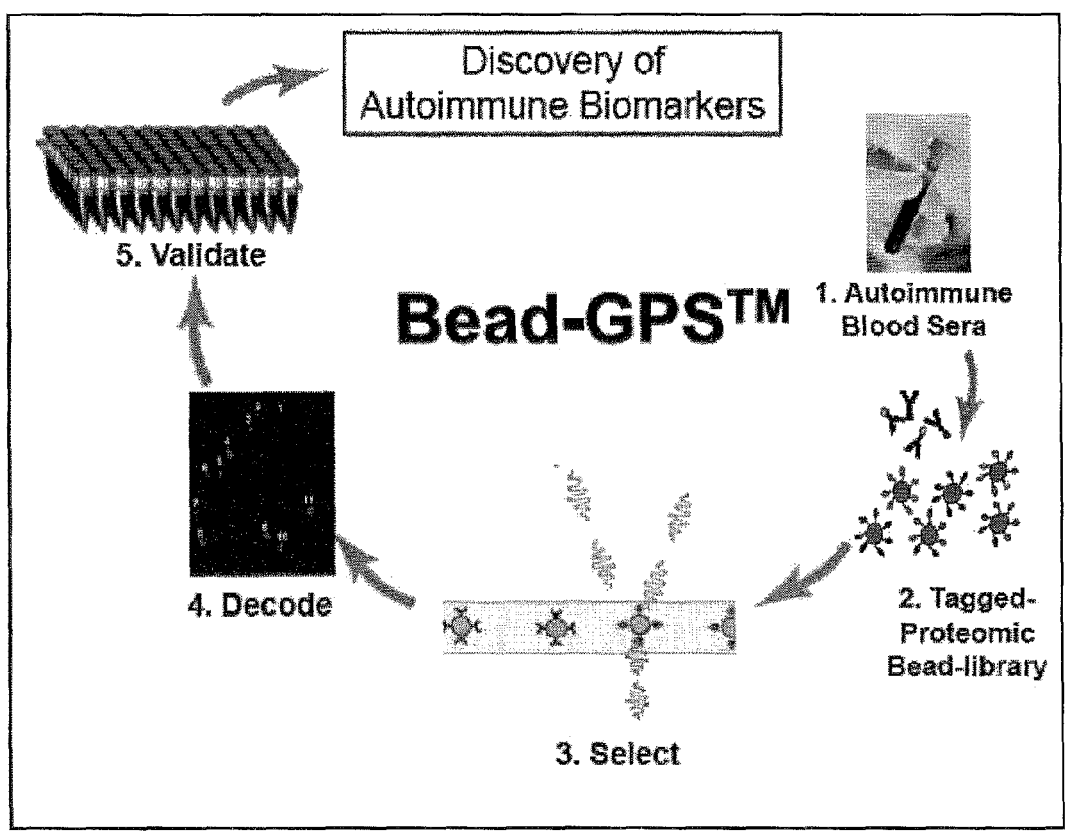

Example of Approach:

A simplified flow diagram for one embodiment of the present invent designed for discovery of autoimmune biomarkers is shown in FIG. 25. It consists of several steps briefly described below and in more detail in the following sections.

1. Sample:

For the discovery process, the sample consists of blood sera obtained from patients with a known autoimmune disease or no known disease (control). Auto antibodies that are typically present in such autoimmune disease patients constitute the prey molecules in this invention 2. Probe Proteomic Bead-Library with Sample:

The sera are mixed with a proteome bead library prepared using recombinant or cell-free protein expression methods. The full library will encompass 15,000 unique human proteins and 20 bead replicates for each protein in the library (total 300,000 beads). These proteins constitute the bait molecules in this invention and are also potential autoantigens or biomarkers that can be utilized in diagnostic tests for autoantigen diseases. In some applications, after mixing the proteomic bead-library with sample, the beads are randomly arrayed into a pico-well plate suitable for both fluorescent and MALDI-MS imaging.

3. Selection:

Positive beads that interacted with autoantibodies present in the sera are selected for decoding. A variety of methods are provided for selection. In one preferred method, beads are first scanned for fluorescence which originates from fluorophores that are bound directly or indirectly to the autoimmune antibodies through binding agents. In one embodiment, the fluorescence label is bound directly to a secondary antibody which is specific for the class of antibodies in the sera (e.g. human IgG). In this case, the secondary antibody serves as the binding agent. In all cases, autoantibodies which bind to beads will result in fluorescence emitted from the beads where prey molecules interact that is detected by conventional fluorescent scanners. In a second embodiment, the beads which are positive are identified using flow-cytometry often and physical separated from other beads (FACS). In a third method, the beads which are positive are physically separated using magnetic beads.

In another embodiment, the positive beads are selected using MALDI-MS bead imaging wherein the mass-tag is attached to the prey molecule, either directly or indirectly through a binding agent. For example, the prey molecule could be an autoantibody directed at a specific autoantigen on an individual bead. In some cases the mass tag is attached via a binding agent such as a secondary antibody. In these cases, positive hits are identified by detection of the specific mass tag associated with the prey molecule.

It is also to be understood that in the present invention different mass tags can be attached directed or indirectly to different prey molecules in order to distinguish which prey molecules interact with which bait molecules. For example, in the case of studying protein-protein interactions, a library of proteins can be coded by attaching different mass tags to each type of protein in the library. Once a protein in the library (prey molecule) interacts with a specific bait molecule on a specific bead, its identity can be determined because of its attachment to a specific mass tag which is different from other mass tags used to code prey molecules and specific bead types.

In another example, different mass tags are used to code autoantibodies originating from different samples. In this embodiment, each sample which may contain autoantibodies are mixed with a suspension of beads and then the autoantibodies allowed to interact with the bait molecules residing on beads. Mass tags specific for each sample are then attached to autoantibodies (prey molecules) through a binding agent which in this case is a secondary antibody. The various bead suspensions exposed individually to different samples are then mixed together and an bead array formed which is measured using MALDI-MS-Imaging. The beads which have bound prey molecules can then be identified along with the sample which the prey molecules originated since each prey molecule (autoantibody) has a unique mass tag.

4. Decoding:

The beads selected in the previous step as positive are decoded to determine the identity of the protein residing on the bead. This is accomplished by measuring the mass of the photocleavable mass tag present on the selected bead by MALDI-MS. A variety of other methods are also described in this invention to determine the identity of photocleavable tag including RT-PCR and DNA hybridization.

5. Validation:

Using a new patient cohort, each individual biomarker determined in steps 1-4 is clinically validated by testing for its diagnostic sensitivity and specificity using an independent method such as two-epitope solid-phase $T^2$-ELISA™ assay based on cell-free protein synthesis technology.

Bead Library Construction

Several methods can be used to construct the proteomic-bead library. One method termed Parallel Preparation, consists of cell-free expression in a separate reaction of each protein in the library from a specially designed plasmid containing the target gene. This is followed by binding of the expressed protein to beads and pooling of all beads in a bead-library. A second method described in US Patent Application Nos. 20090264298, 20090270278, 20090286286, 20100062451 and 20100075374, termed here as the Batch Preparation method, involves only two reactions to create the entire library and relies on advanced methods utilizing single-molecule solid-phase emulsion PCR and self-assembling cell-free expression.

Figure 26:
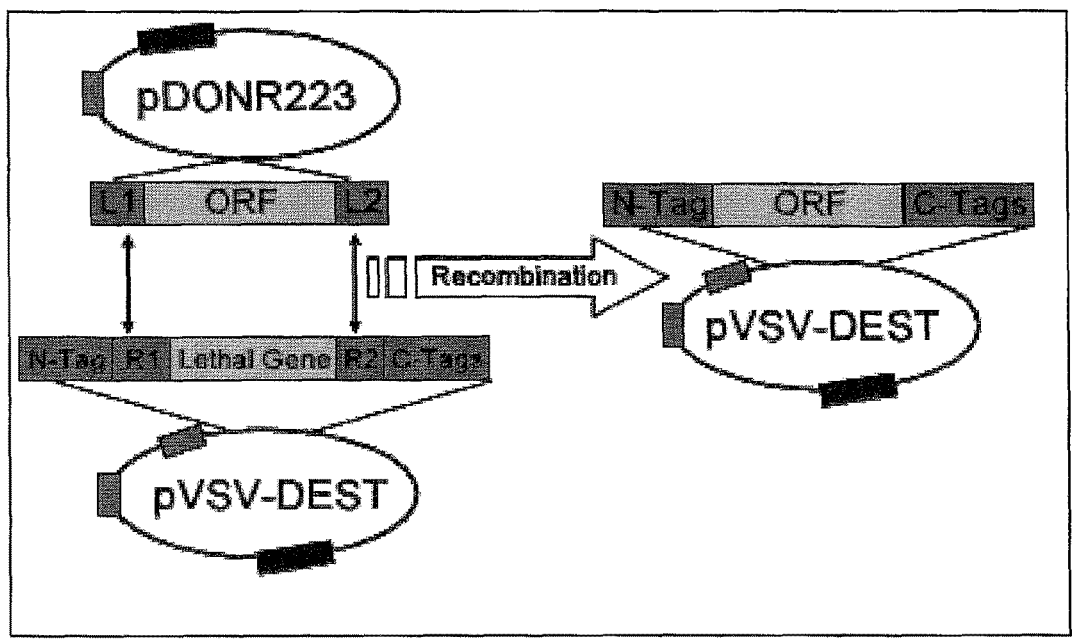

We described below several examples of steps used in bead library construction in the present invention:

Plasmid Construction:

As illustrated in FIG. 26, we have developed a facile approach for constructing the plasmids used in the cell-free protein translation reactions which is based on the commercially available 12,000-member Open Reading Frame (ORF) template library (ORFeome) [Rual, Hirozane-Kishikawa et al. (2004) Genome Res 14: 2128-35] derived from NIH backed Mammalian Gene Collection. This library can be transferred into a custom in-house developed destination vector (pVSV-DEST vector) using the high throughout Gateway™ recombination method (Invitrogen). The Gateway™ system allows flexibility by facilitating recombination into a variety of expressible acceptor (destination) vectors. Our pVSV-DEST acceptor vector affords excellent expression in a variety of cell-free reaction mixtures including E. coli, rabbit reticulocyte and wheat germ lysates. Gateway™ compatible acceptor vectors for insect cell lysate expression systems have also been prepared by AmberGen. In addition to the Open Reading Frame (ORF) inserts, nucleic acid sequences coding for common epitope tags at the N- and C-terminal end of the nascent protein are included (a key feature of the ORFeome is that the stop codon is absent, allowing for N-Tagging). The Gateway™ process is rapid, facile and efficient and avoids tedious sub-cloning.

Cell-Free Protein Transcription & Translation:

Customized plasmid constructs as described above will be used to express the required protein for the library in a cell-free (in vitro) expression system. Until recently, relatively high costs and low yields have discouraged the use of cell-free protein expression systems in the field of proteomics. However, recent dramatic improvements in this field hold great promise for solving many of the problems that have previously limited the use of this approach. Advantages and improvements include: On-Demand Expression: Express specific proteins, on-demand, typically in <1 hr, even in eukaryotic (e.g. mammalian) systems using a single facile reaction (e.g. Promega's batch mode rabbit reticulocyte or insect cell coupled transcription/translation system). High Yield: New "continuous exchange" cell-free (CECF) expression systems capable of ~1 mg/mL yields (e.g. Roche's Wheat Germ CECF now sold by 5 Prime, Inc.). In these systems, the expression reaction is separated from a feeding buffer by a semi-permeable membrane. The feeding buffer provides a continuous supply of small molecule precursors while absorbing (by diffusion) inhibitory byproducts. The devices (FIG. 27)) fit into a 96-well microtiter plate frame for automation. Protein Compatibility: Often proteins cannot be expressed in cellular systems due to cytotoxicity or interference with host cell physiology [Henrich, Lubitz et al. (1982) Mol Gen Genet 185: 493-7; Goff and Goldberg (1987) 1 Biol Chem 262: 4508-15; Nakano and Yamane (1998) Biotechnol Adv 16: 367-84; He and Taussig (2001) Nucleic Acids Res 29: E73-3; Endo and Sawasaki (2003) Biotechnol Adv 21: 695-713]. Membrane Proteins: The ability to express membrane proteins in nanolipoparticles [Cappuccio, Blanchette et al. (2008) Mol Cell Proteomics 7: 2246-53; Katzen, Fletcher et al (2008) J Proteome Res 7: 3535-42; Cappuccio, Hinz et al. (2009) Methods Mol Biol 498: 273-96], small discoidal membranes mimicking the native membrane protein environment, using commercial kits such as the Invitrogen MembraneMAX™ cell-free protein expression kits [Cappuccio, Blanchette et al. (2008) Mol Cell Proteomics 7: 2246-53; Katzen, Fletcher et al (2008) J Proteome Res 7: 3535-42; Cappuccio, Hinz et al. (2009) Methods Mol Biol 498: 273-96].

Since the proteomic-library will consist of a wide-variety of different proteins it is essential that cell-free reactions are designed to be compatible with expression of these different types of proteins. However, there is abundant evidence that such a diversity of proteins can be universally expressed if the proper system is chosen. For example, recent studies reported in Nature Methods [Goshima, Kawamura et al. (2008) Nat Methods 5: 1011-7] using wheat germ expression system has been shown to be capable of expressing at least 13,346 proteins from the proteome. The expression system was a variant of the aforementioned high yield CECF system, except that as an alternative to the 2-chambered devices, the so-called "bilayer" method was used to overlay the feeding buffer directly onto the expression reaction [Sawasaki, Hasegawa, Tsuchimochi, Kamura, Ogasawara, Kuroita and Endo (2002) FEBS Lett 514: 102-5]. Recently, synthetic nanolipoparticles (NLP) [Cappuccio, Blanchette et al. (2008) Mol Cell Proteomics 7: 2246-53; Katzen, Fletcher et al. (2008) J Proteome Res 7: 3535-42; Cappuccio, Hinz at al. (2009) Methods Mol Biol 498: 273-96], small discoidal membranes mimicking the native membrane protein environment, have been used for cell-free expression of properly folded and functional membrane proteins.

Figure 28:
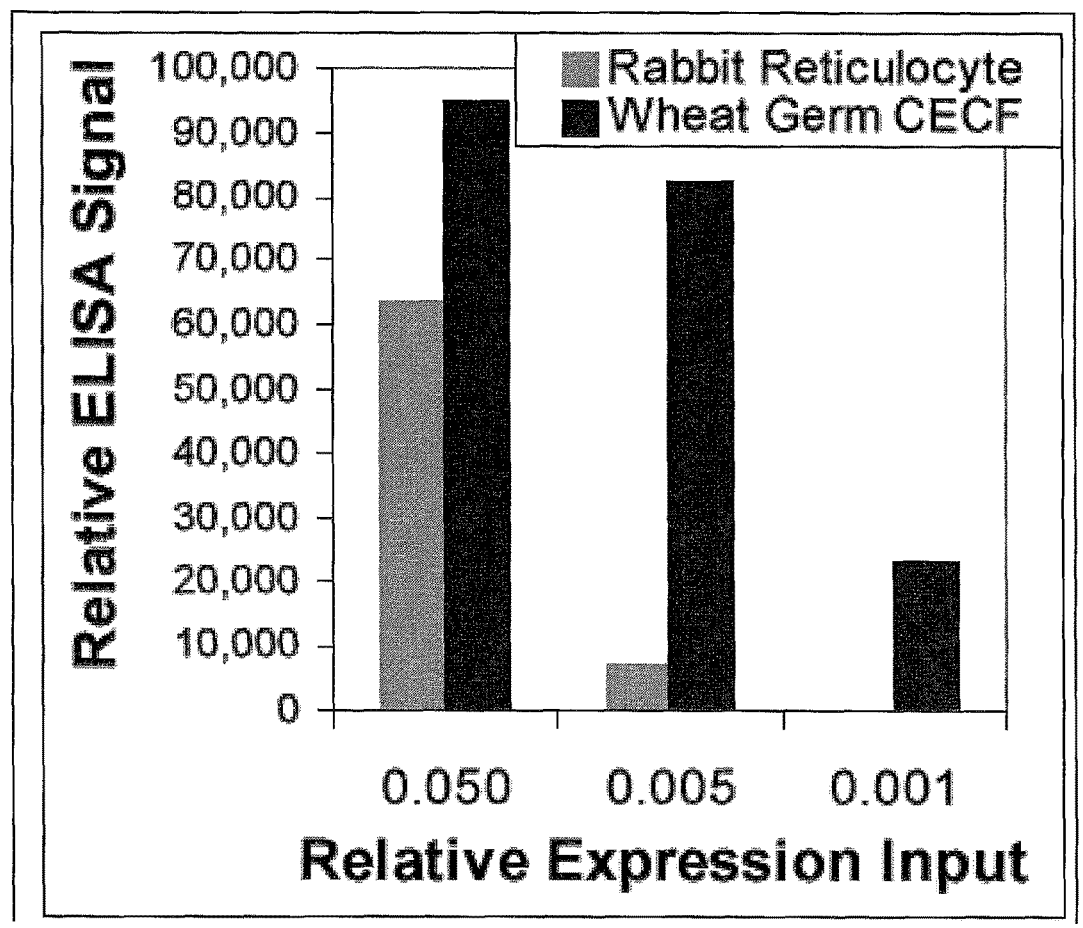

In one example of the prototype library construction used in this invention, we have used the Promega rabbit reticulocyte cell-free expression system, known for its ability to produce functional, properly folded and even post-translationally modified proteins, including multi-pass membrane proteins, especially considering it is a mammalian system, and as a cell lysate, native chaperones are not removed [Gibbs, Zouzias and Freedberg (1985) Biochim Biophys Acta 824: 247-55; Hirose, Kim, Miyazaki, Park and Murakami (1985) J Biol Chem 260: 16400-5; Vorburger, Kitten and Nigg (1989) Embo J 8: 4007-13; Pensiero, Dveksler, Cardellichio, Jiang, Elia, Dieffenbach and Holmes (1992) J Virol 66: 4028-39; Middleton and Bulleid (1993) Biochem J 296 (Pt 2): 511-7; Popov, Tam, Li and Reithmeier (1997) J Biol Chem 272: 18325-32; Lyford and Rosenberg (1999) J Biol Chem 274: 25675-81]. Examples of two high yield systems which can be used in conjunction with library construction are: i) insect cell coupled transcription/translation systems (Promega) and ii) wheat-germ continuous flow system (Roche; now sold by 5 Prime Inc.). FIG. 28 shows that the 100-fold expected yield improvement of the Wheat Germ CECF system over the rabbit reticulocyte is in fact achieved. In this example, a known autoantigen, snRNP C, was cell-free expressed in both systems and analyzed by the AmberGen's aforementioned $T^2$-ELISA™ assay. To avoid saturation of the capture antibody on the ELISA plate, the expression reaction was serial diluted prior to input into the assay. At the lowest expression input, the wheat germ system is measured at 94-fold better yield than the rabbit reticulocyte, in line with the manufacturer reported yields of the 2 systems (600 and 7 ng/µL respectively).

Figure 29:
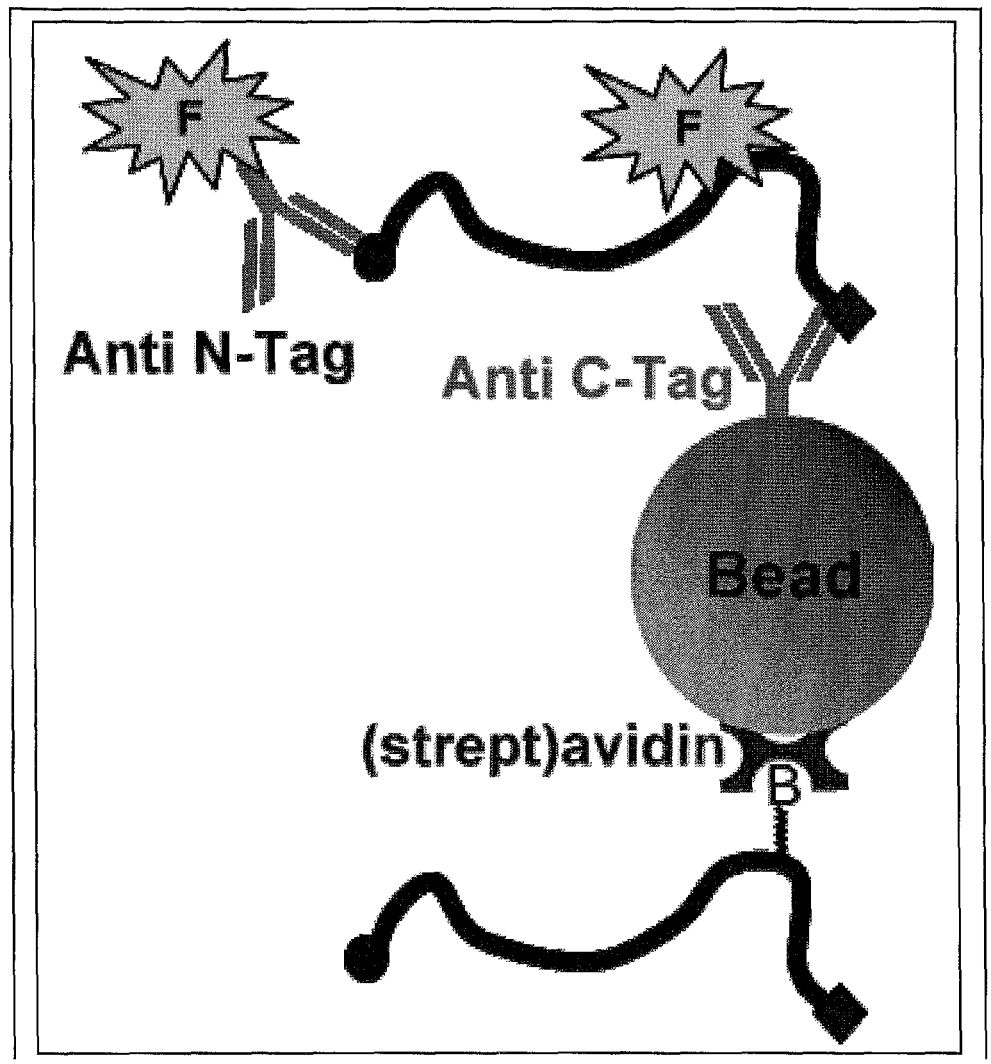

One-step Capture of Protein on Bead: As illustrated in FIG. 29, in one embodiment of the present invention each expressed protein in the library is purified and attached to the bead through a simple one-step process. This is accomplished through the common HSV-epitope (C-Tag) incorporated into each protein which binds to an anti-HSV antibody present on the 34-micron agarose beads. We have measured a 75% capture efficiency from cell-free expression lysates with this antibody system [Lim and Rothschild (2008) Anal Biochem 383: 103-115]. It should also be noted that we have shown this attachment method to be extremely stable. For instance, after overnight incubation of a mixed population of protein-beads at room temperature with vigorous shaking, no significant drop in signal and no bead-to-bead cross-contamination was observed.

As an alternative to the above approach, tRNA mediated engineering technology such as described in various patents issued to AmberGen Inc. [e.g. U.S. Pat. Nos. 5,643,722; 5,922,858; 6,210,941; 6,303,337; 6,306,628; 6,344,320; 6,358,689; 6,566,070; 6,596,481; 6,875,592; 6,949,341; 7,169,558; 7,252,932; 7,288,372 and 7,524,941] can be used to co-translationally incorporate biotin labels for attachment to (strept)avidin beads [Lim and Rothschild (2008) Anal Biochem 383: 103-115], thereby exploiting the unparalleled affinity of this interaction (Kd=1015, roughly 6-orders of magnitude better than an average antibody).

An important feature of the present invention when agarose beads are used is that it exploits the extremely high protein binding capacity of the porous 6% cross-linked 3-dimensional matrix of the 34 micron agarose beads. According to the manufacturer's specifications (GE Life Sciences), the chemical surface activation (primary amine-reactive NHS groups) of the uncoated agarose beads is 10 μmoles/mL of packed bead volume, which would correspond to 50,000 pg/bead of antibody attachment capacity. However, in practice, due to steric factors, the much larger antibody cannot be loaded to such levels. The typical antibody binding capacity of such beads is ~10 mg/mL of beads, or ~300 pg or 2 fmoles/bead (1 mL 30 million beads). This still compares favorably to conventional 2-dimensional planar proteome microarrays such as Invitrogen's ProtoArrays®, with published densities of 1 pg/spot maximum (100 micron spots) [Zhu, Bilgin et al. (2001) Science 293: 2101-5]. Furthermore, this should easily facilitate our targeted intended loading of 10 pg (0.2 fmoles) per bead of expressed protein on average, in addition to the loading of the peptide mass-tags. Note that because an antibody is larger (150 kDa) than a typical protein (calculations on 50 kDa), 30 pg/bead (0.2 fmoles) of antibody is targeted.

Figure 30:
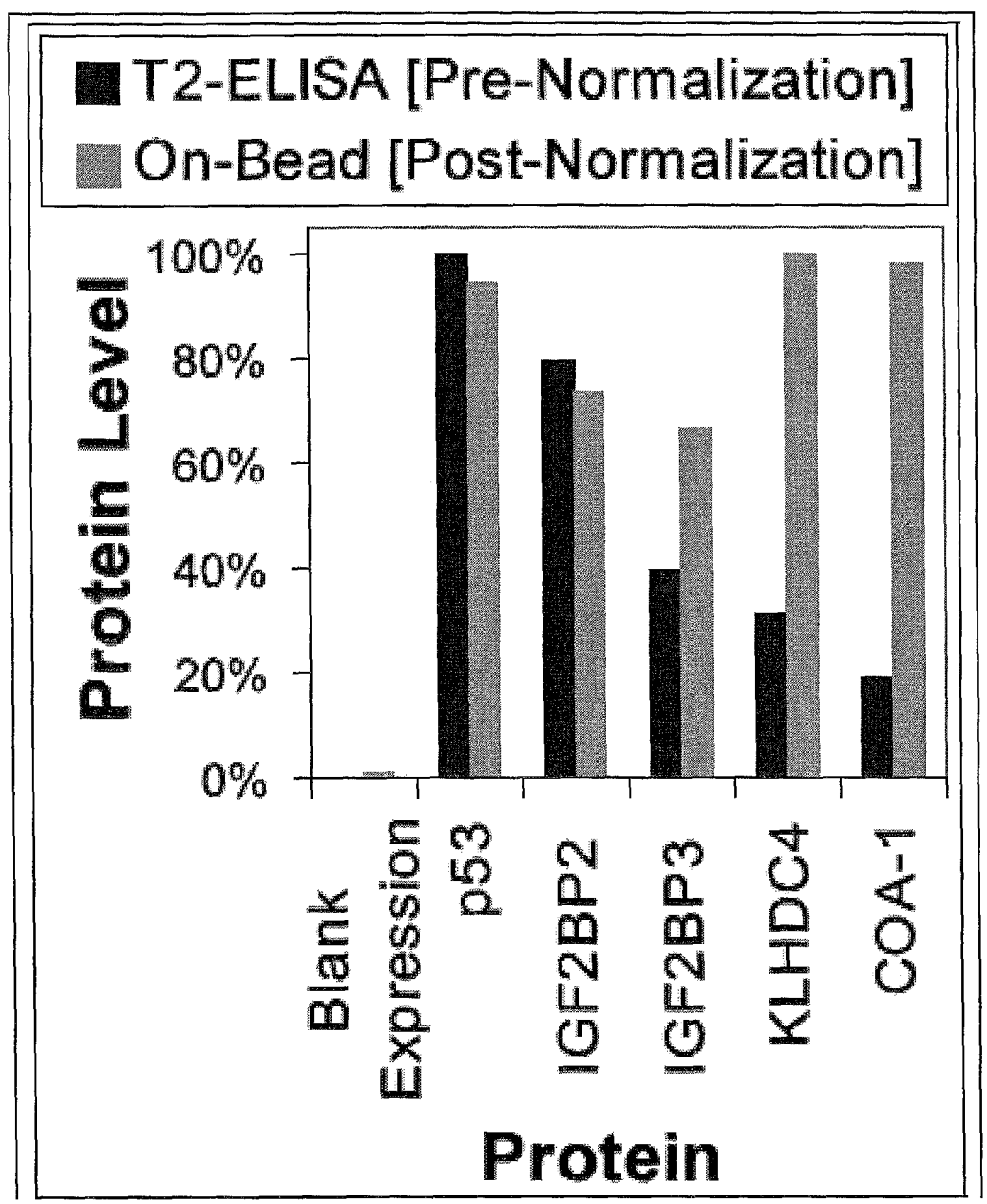

Another important feature of the bead-based capture is the ability to easily normalize for protein-protein variances in expression yield (see FIG. 30).

Automation of Bead-Library Fabrication:

An important feature of the bead-library fabrication is the ability to fully automate the process. This ability stems from relatively few steps involved in the overall preparation of the protein-beads. In essence, because of the cell-free expression and in situ protein capture, the fabrication of the bead library is only a series of steps involving mixing of reagents and washing beads. In particular, each step can be carried out in parallel on standard 96-well plates using our in-house robotic plate handling systems. For example, transfer of the genes from the ORFeome library to the pVSV-DEST expression vectors essentially involves a single recombination step using the Gateway™ recombination system. In fact, high throughput automated Gateway™ recombination has been done with 93% efficiency without the need for bacterial plating and/or colony picking at any stage [Janney, Roby, Getbehead, Bell, Daniels and Chesnut 2009; Aguiar, LaBaer et al. (2004) Genome Res 14: 2076-82]. Similarly, expression of the protein in a high yield coupled translation/transcription reaction requires just one step which involves mixing reaction components and vector in a tube followed by incubation at a controlled temperature. The purification of the protein from the reaction system and binding to beads also involves a single-step process. Since our library encompasses ~15,000 proteins, this will require methods that involve robotically processing approximately 150×96-well plates for each of the 5-steps (note we anticipate that the ORFeome will expand to this number from its currently available 12,000 clones). This number of plates can be easily accommodated using industry standard multi-plate stacking devices which are compatible with our robotic systems.

Alternative Batch Library Production with Advanced Single-Molecule Technologies:

As an alternative to the Parallel Preparation method of fabricating the proteome bead-libraries in the present invention, an alternative method described in US Patent Application Nos. 20090264298, 20090270278, 20090286286, 20100062451 and 20100075374 is potentially more efficient and cost effective. This fully multiplexed Batch Preparation method uses a single-tube reaction to first produce an entire bead sorted library of in vitro expressible DNA (BS-LIVE-DNA). For this, universal PCR primer beads (vector targeted) are emulsified in oil with the expressible ORFeome library as template such that single beads are compartmentalized in aqueous droplets (millions per reaction) containing single copies of template. The emulsion PCR reaction thus clones and amplifies single DNA molecules onto beads, and is normally used for genetic assays [Dressman, Yan, Traverso, Kinzler and Vogelstein (2003) Proc Natl Acad Sci USA 100: 8817-22]. After loading the common capture antibody onto the resultant BS-LIVE-DNA beads (via a biotin-(strept)avidin bridge), the bead population is subjected to a single-tube self-assembling cell-free expression reaction [Nord, Uhlen and Nygren (2003) J Biotechnol 106: 1-13; Ramachandran, Hainsworth et al. (2004) Science 305: 86-90] to convert BS-LIVE-DNA to a bead sorted library of in vitro expressed proteins (BS-LIVE-PRO). In this reaction, proteins are simultaneously translated and captured back onto the parent DNA beads from which they were made, by way of the capture antibody directed against a common epitope tag in each protein. Although not required per se, methods to reduce mRNA/protein escape from its parent DNA encoded bead can be employed, such as expression in an emulsion or in the pico-well plates to reduce diffusion.

MALDI-MS Measurements of Individual Bead in an Array

An important feature of this invention is the demonstrated ability of MALDI-MS to rapidly measure a variety of molecules residing on individual beads as part of an array of beads. In one preferred embodiment of this invention this ability allows decoding of individual beads that have been identified as displaying positive interactions between bait molecules residing on bead and prey molecules which interact with said bait molecules. In several example described in this invention; we have demonstrated that MALDI-MS is capable of rapidly decode PC-Mass-Tags on beads, including their utilization to detection the interaction of autoantibodies with autoantigens residing on individual beads. In general this ability to measure molecular interactions on individual beads using MALDI-MS, offers many advantages not limited to just mass-tag decoding but also for direct identification of proteins and other biomolecules residing on the bead surface or indirectly attached to the bead as described below.

Several examples of the ability of MALDI-MS to image individual beads that were performed using an ABI 4800 Plus MALDI-TOF-TOF mass spectrometer (see Examples below) although such measurements are not limited to this particular model of MALDI-TOF instrument. Typically, scanning is done using the ABI 4800 software in the positive ion reflector mode with internal calibration using 50-200 laser pulses per sample spot, which results in measurement times of ~0.25-1 s per bead. Image acquisition and analysis is performed using public domain software (www.maldi-msi.org; 4000 Series and BioMap software respectively).

Fluorescent Selection of Positive Beads

Fluorescent Scanning of Beads in Pico-Well Plate:

In one embodiment of the present invent designed for biomarker discovery involving autoimmune disease, hits corresponding to proteins that interact with autoimmune antibodies in the sample serum (i.e. putative biomarkers) are selected by detection of fluorescent spots on a conventional proteomic microarray. In contrast, the present invention relies on identification of positive beads. This can be accomplished in several ways such as but not limited to fluorescent scanning of the beads residing in a pico-well plates after exposure to the test sera. The positive beads identified can then be decoded using MALDI-MS bead scanning and positive hits further confirmed by detection of mass-tags attached to the read-out antibody.

Fluorescent Labeling of the Probe (Prey) Molecule:

There are a multitude of fluorescent based methods commonly used to identify the interaction of a bait molecule with probe (prey) molecule. One common method is based on using a fluorescently-labeled antibody directed against the probe molecule which is applied either before or after the bait-prey interaction occurs. In the case of autoimmune antibodies residing in patient sera for example which are themselves the prey molecules, a fluorescently labeled secondary antibody is used which is directed against the autoimmune antibody. Alternatively, a fluorescently labeled streptavidin molecule can be used directed at a biotinylated antibody which is in turn directed against the probe molecule such as an autoimmune antibody. In all of these cases the antibody serves as a binding agent coupling the prey molecule with a fluorescent molecule. The binding agent might also comprise a group residing on the prey molecule which facilitates a covalent linkage with the fluorescent label such as through at activated or reactive chemical group. For example, the epsilon amino group of lysines residing on proteins can be chemically labelled with appropriate fluorophores which are commercially available. It is to be understood that labeling of the probe molecules is not limited to a single fluorescent molecule. In some embodiments it is advantageous to use different fluorescent labels for different prey molecules that might be coupled to the prey molecule through different binding agents such as antibodies or reactive chemical groups. It is also to be understudy that probe molecules can also comprise a coding agent such as a photocleavable mass tag.

As listed below, there are several key advantages to this approach over conventional microarrays including:

More Reliable Hit-Identification Due to Increased Replicates:

The ability to scan in a few minutes a large bead library of beads such as V-million beads arrayed on the pico-well substrate provides more reliable hit-identification than conventional microarrays. In comparison to the typical <20,000 spots with 2-replicates used on the conventional proteomic microarrays, the current invention can scan significantly more replicates (~20) providing better statistics for identifying weak protein-antibody interactions.

False-Positive Rejection:

Since in one embodiment of the invention the probe antibody is doubly labeled with not only a fluorescent label but a photocleavable mass-tag designed for MALDI-MS bead imaging read-out, this assures that any false positive beads selected during the sort step will be rejected during decoding. See FIG. 7 (Experimental Examples) for one embodiment of this redundant design.

Multi-Dimensional Hit Identification:

The use of multiple fluorescent labels with different wavelengths of excitation provides more robust ability to separate different positive hits. For example, the probe antibody can be coded with different fluorescent dyes in order to differentially label different samples scanned. Such a capability is not possible using conventional microarrays since the sera is applied directly to chip instead of to beads in separate reaction vessels prior to application to pico-well slide.

Non-Dry Conditions:

Conventional proteome microarray fabrication involves several steps which subject the proteins to non-physiological conditions. For example, printing followed by drying can lead to protein denaturation. Microarrays are also stored and shipped dry for long periods of time which can lead to further protein alterations. In addition, antibody interactions occur on two-dimensional protein spots printed on an array surface which could alter the ability of the antibody to freely interact with all proteins in the spot. In contrast, the beads used in the present invention can be kept fully hydrated so the proteins are never exposed to drying. Furthermore, the antibody-antigen interaction and hence selection of positive hits occurs in a fully controllable aqueous environment selected to promote native protein conformation.

In-Line Quantification of Protein Per Bead

Variability of protein content on each bead can be easily accounted for in hit selection by using AmberGen's proprietary FluoroTag™ technology (FIG. 29 and described in U.S. Pat. Nos. 5,643,722; 5,922,858; 6,210,941; 6,303,337; 6,306,628; 6,344,320; 6,358,689; 6,566,070; 6,596,481; 6,875,592; 6,949,341; 7,169,558; 7,252,932) which allows incorporation of fluorescent labels during cell-free synthesis. Alternatively, two-tag technology described in U.S. Pat. No. 7,423,122 provides a means of probing protein content on beads using a fluorescently labeled antibody directed against the N-terminal epitope of each protein.

Fluorescence-MALDI Image Synchronization for Bead Selection

An important feature of one embodiment of this invention is the ability to synchronize the fluorescent scan with the MALDI-MS measurements on the bead array thereby reducing the number of beads which need to be scanned by MALDI-MS. In this embodiment, beads which exhibit an interaction between the bait molecule residing on the bead and prey molecule is measured first using conventional fluorescent scanning and detection methods to determine if a fluorescently labeled prey molecule has interacted with the bait molecule on a particular bead in the array. The position of the positive hits detected in this scan are then used to direct the MALDI-MS spectrometer to the position of these positive beads in order to, determine the mass of the mass tags residing on individual bead and thus the identity of the protein. It is to be understood that this approach is not limited to fluorescent measurements but other detectable properties such absorption, luminescence, Raman, infrared could be used to detect positive interactions of bait and prey molecules and the positions determined used to guide measurements of the bead array for subsequent MALDI-MS measurements and decoding.

Typically, fluorescent detection is performed with a conventional fluorescent scanner which can assay hundreds of thousands of beads in a single scan in a few minutes at high resolution (typically 3-5 microns). The arraying of the beads on a substrate with uniform spaced wells of proper depth allows only one bead per well such as for the case of the pico-well plates designed for 34 micron diameter beads described above thus preventing the overlap of beads and subsequent ambiguous measurements. Once the positive-hits are identified, the mass spectrometer can be directed to measure the mass tags residing on those particular beads identified by fluorescence, thereby avoiding the measurement of mass tags on every bead residing in the array.

As described, elsewhere in this invention prey molecules can also be preferentially attached to mass-tags, either directly or through binding agents, thus providing an separate means to detect and confirm positive hits (i.e. interaction of prey and bait molecules on a bead) and also to determine the identity of one or more prey molecules which might exist in a mixture or solution and may interact with the bait molecule residing on an individual bead.

One embodiment of this invention utilizes beads which are both mass-tagged and fluorescently labeled to aid in guiding the MALDI-MASS spectrometer to measure more accurately to the position of beads with positive hits identified by fluorescence. In this embodiment, the x-y position of the so-called synchronization beads is first determined in the fluorescent scan. The synchronization beads comprise a fluorescent label and a mass tag. The fluorescent label used for synchronization beads has properties different from those fluorescent labels used to label prey molecules (e.g. a distinguishable emission spectrum). In addition, the mass tag(s) used for synchronization beads has a different mass then other mass tags used to identify beads with bait molecules or prey molecules. Once the x-y coordinates of these synchronization beads is determined from the fluorescent image of the bead array, the information can be used to guide the MALDI-MS instrument to find the same beads in the MALDI-MS generated image.

Confirmation that the MALDI-MS system is measuring the correct bead in the array is provided by measuring the corresponding mass tag residing on the synchronization beads. Importantly, once the synchronization beads are identified in both the fluorescent image and MALDI image, the position of positive beads identified by the fluorescent scan can be more accurately located in the MALDI-MS scan and mass tags measured to determine the identity of the bait and prey molecules residing on the bead. Increased accuracy for identification of positive hits can be accomplished by increasing the number of synchronization beads randomly incorporated into the array, thus providing more local coordinate information to determine precise location of nearby positive-hits. This method is especially useful for MALDI-MS systems which do not intrinsically have high resolution scanning capability (e.g. MALDI laser beam diameter which exceeds the size of the bead diameter) or in cases where the positional accuracy of the wells incorporated into the pico-well plates vary in position compared to exact 2-D periodic lattice.

It is to be understood that in addition to using fluorescently labeled synchronization beads described above other detectable properties can be used including absorbance in the visible, infrared or UV, Raman scattering and even magnetic properties. In each case, a scan of this property provides the MALDI-MS system with coordinates that aid in scanning of the beads. As one example, of how this feature might be implemented on commercially available instruments, the Bruker Ultraflextreme MALDI-MS spectrometer is equipped with software that allows one to synchronize features obtained by scanning the sample on an external system based on fluorescence or absorption properties with a visual image obtained using its high resolution camera incorporated into the machine.

In one preferred embodiment, the detection of fluorescent or other properties such a light absorption of the beads is measured directly on the MALDI-MS system in order to identify positive hits (positive interactions between prey and bait) and then used this information to determine which beads are measured directly by MALDIMS.

For example, the high resolution capability of the camera and imaging system which is incorporated into the Bruker Ultraflextreme MALDI-MS instrument allows detection of beads of less than 20 microns that have been colored with a light absorbing chromogenic dye. Since a variety of chromogenic based agents have been developed to label positive interactions between bait and prey molecules such as the use of antibodies conjugated to horse radish peroxidase (HRP). A similar labeling method can be used to directly label positive bait and prey interactions on individual beads which can be detected directly in the MALDI-MS instrument such as the Bruker Ultraflextreme. Those skilled in the art of MALDI-MS instrumentation will also recognize it is possible to incorporate fluorescent detection so that fluorescent labeling methods can be utilized to identify bait-prey interactions on individual beads.

In addition to pico-wells formed from fiber optic bundles, a photolithographic method of well fabrication can be utilized to increase accuracy of the position of each well. In addition, the ability of fluorescent scanners to detect multiple wavelengths will enable marker beads to be utilized that will allow more accurate registration of the fluorescence and MALDI images to be made.

Additional Methods of Selecting Positive Bait-Prey Interactions on Beads for MALDI-MS Decoding.

An alternative (or complement) to direct selection of positive hits (beads) by fluorescence imaging prior to MALDI-MS decoding is the use of physical methods to separate positive beads from negative beads. One such approach is the use of fluorescence assisted cell-sorting (FACS). A second method is based on a magnetic bead sorting techniques.

Similar to conventional magnetic cell-separation techniques, the protein-beads of Bead-GPS™ can be pre-isolated by small (1 micron) magnetic particles prior to fluorescence imaging and/or MALDI-MS decoding. Moreover, magnetic particle manipulation is particularly amenable to automation, for example, as achieved by Bio-Rad's (Hercules, Calif.) BioPlex multiplex immunoassay system.

Figure 11:
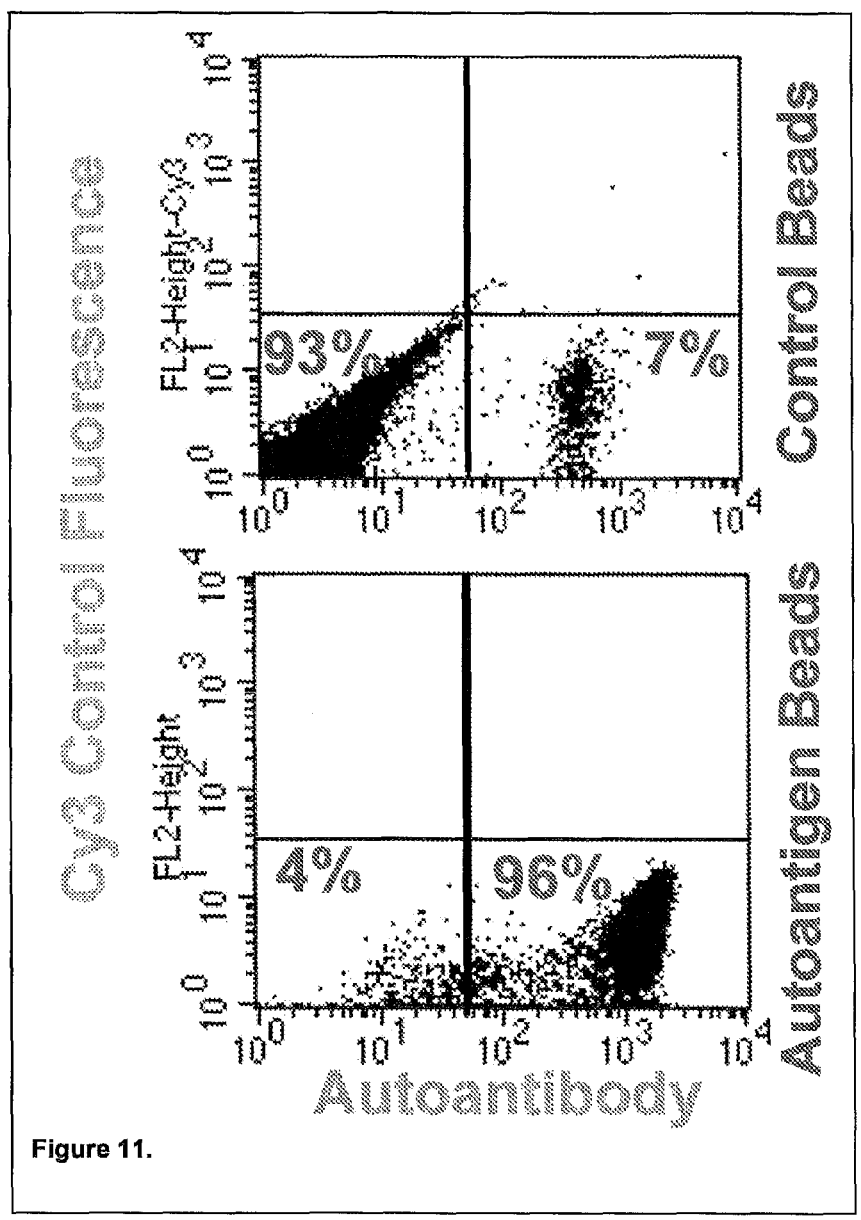

Another embodiment of this invention involves the isolation of the 34 micron agarose beads using fluorescence activated cell sorting (FACS). Importantly, this method is high throughput (can process millions of beads in a few minutes) and has the ability for greater reproducibility and specificity than the magnetic method, since beads can be analyzed by multiple parameters on a bead-by-bead basis. As shown in FIG. 11 (Experimental Examples), blank protein beads (cell-free expression lacking expressible DNA) and beads containing a novel autoimmune autoantigen for PBC were separately prepared and probed with an appropriate antigen positive human serum. Bound autoantibody was detected with a fluorescently labeled secondary antibody (fluorescein). As seen, using the same cutoffs, 93% of the control beads were scored negative while 96% of the autoantigen beads were scored positive. Specificity of the fluorescence signal is verified by analysis in using a second fluorescence channel (Cy3), showing no significant signal.

Although selection either by imaging or physical separation of positive hits (beads) prior to MALDI-MS decoding is the preferred method, it should be noted that it is not required. As demonstrated, mass-tags can be used alone for both bead identification and autoantibody readout (see examples). In this case, since hits are not pre-imaged by fluorescence, the entire library is imaged by MALDI-MS in the pico-well plates. Importantly, the newer generation of faster scanning MALDI-MS instruments can do this in a relatively short amount of time.

Mass-Tags for Bead and Prey Decoding

Basic Concept:

Once beads have been sorted or selected for positive "hits" on the basis of fluorescence scanning as described above, the next step in one preferred embodiment of this invention is decoding the beads in order to identify the bait molecules which are bound to them. A similar process is also used for identifying prey molecules which interact with the bait molecules (see below), It is also to be understood that the use of fluorescence scanning in some embodiments is not necessary in cases where each bead in the bead array is canned individually. In this case, positive hits can be identified using decoding methods described in this invention.

One preferred embodiment of the invention which entails a method of detecting the interaction of prey molecules with bait molecules, comprises: a) providing a mixture comprising first and second beads, said first bead comprising a first mass tag and a first bait molecule, said second bead comprising a second mass tag and a second bait molecule, wherein said first and second bait molecules and said first and second mass tags are different; b) making an array with said beads; c) contacting said first and second bait molecules with a solution comprising a prey molecule, wherein said prey molecule comprises a mass tag; and d) subjecting said array to MALDI mass spec analysis under conditions wherein binding of said prey molecules to a bait molecule is detected.

A second embodiment of the invention involves reversing steps b) and c) listed above so that the contacting of said and first and second bait molecules with a solution comprising a prey molecule occurs before making an array of said beads.

It is to be understood that the bait and prey molecules can consist of a large variety of different biomolecules or biologically active molecules such as proteins, antibodies or potential drug compounds. For example, bait or prey molecules includes but are not limited to proteins, polypeptides, nucleic acid molecules, lipids, carbohydrates, biologically active drug compounds, hormones, antigens, antibodies and combinations of these molecules. The aforementioned bait and/or prey molecules can also be labeled using standard fluorescent labeling reagents comprising one or more fluorophores (see examples) in order to identify positive bait/prey interactions and facilitate fluorescent image synchronization with MALDI-MS imaging as described elsewhere in this invention.

In one example, bait molecules consist of various proteins selected from a protein library such as can be expressed as described in this invention using the commercially available 12,000-member Open Reading Frame (ORF) template library (ORFeome), whereas prey molecules consist of autoantibodies present in a patent's blood that are associate with autoantigens underlying an autoimmune disease such as primary biliary cirrhosis or lupus. Similarly, antigens might be tumor specific (tumor associated antigens (TAAs) related to a particular cancer tumor and antibodies freely circulating in blood may be formed in response to these TAAs and used as biomarkers for detection of the cancer or to predict the course of the cancer (prognostic). Detecting and identifying the interaction of specific antigens with specific antibodies using the present invention provides critical information in designing diagnostic tests, prognostic tests and therapeutic methods related to these specific autoimmune diseases and for specific cancers.

In another example, bait molecules consist of various proteins selected from a protein library such as expressed from the commercially available 12,000-member Open Reading Frame (ORF) template library (ORFeome), whereas prey molecules consist of small molecules that have been selected using standard screening methods well known in the pharmaceutical industry as potential drug compounds. Alternatively the prey molecules might be part a small compound library used to screen for possible drug candidates or drug targets. Detecting and identifying the interaction of a library of small compounds and library of proteins simultaneously using the present invention provides critical information for the pharmaceutical industry in identifying potentially useful drugs, drug targets and also to identify side-effects of drugs.

In another example, both bait and prey molecules consist of various molecules selected from a protein library such as expressed from the commercially available 12,000-member Open Reading Frame (ORF) template library (ORFeome) proteins. In this case, the detection and identification of specific protein-protein interactions provides important information for elucidating various cellular pathways and the role that specific proteins play in active cellular process and in disease. In addition, this information can lead to the discovery of new biomarkers for diagnosis and new drug targets to treat specific diseases involving these cellular pathways.

In another example, bait molecules consist of various proteins selected from a protein library such as expressed from the commercially available 12,000-member Open Reading Frame (ORF) template library (ORFeome) which have been treated with a biologically active molecule which produces a chemical or structural change in particular proteins or polypeptides in the library, whereas prey molecules consist of molecules which are detect or probe chemical and structural changes in the bait molecules. As one example, the protein bait molecules is treated with a specific kinase which causes phosphorylation of specific Tyr, Ser or Thr residues present in the sequence of specific proteins or polypeptides. Once the proteins are treated with this kinase, antibodies that are specific for phosphorylated Tyr, Ser or Thr which constitute the prey molecules are allowed to interact with said protein bait molecules. Detecting and identifying the interaction of specific antibodies with the phosphorylated proteins provides important information about kinase substrate specificity and can identify new drug targets and drugs to treat specific diseases.

In another example, bait molecules consist of various antibodies selected for their specific interaction with a target analytes such as a particular proteins or other molecules whose concentration in a sample is to be determined, whereas prey molecules consist of various antibodies selected for their specific interactions with the same set of target analytes. In this case, detecting and identifying the interaction of bait and prey via mutual interaction with the analyte provides important information about the analytes presence in the sample and its concentration. Such a "sandwich" configuration of antibodies directed against a target analyte in a mixture to be measured is commonly used in sandwich ELISAs and is well known to those in the field of biochemistry and molecular biology. In this case, using the methods provided in this invention, the concentration of thousands of analytes in a sample can be simultaneously measured. In addition, using methods described for coding bait and prey with mass tags, the expression level of thousands of analytes in multiple samples can be determined.

It is to be understood in addition that the mass tags used to code bait or prey molecules can consist of a wide variety of molecules and their isotope labeled variants including but not limited to polypeptides, oligonucleotides, linear block co-polymers, branched polymers and small molecules such as those part of a small compound library used to probe drug targets.

In one embodiment, the method of decoding is based on the use of mass-tags and more preferably photocleavable mass-tags which remain covalently attached to the bead or attached via a binding agent until exposed to light (see below). In one preferred embodiment of this invention, the mass-tags are modified polypeptides whose sequence has been chosen so that its mass is unique (i.e. differs from every other mass tag used in the library). In a second embodiment, the mass-tags are isotopically labeled molecules with the same structure but different masses. In a third embodiment, the mass tags consist of a different polymers than a polypeptide such as an oligonucleotide. In a forth example, a 2,2'-(ethylenedioxy)-bis-(ethylamine) is used as the basic building block for constructing the mass tag. It is to be understood that in this invention there are a variety of molecules which would serve as mass tags and it is not limited to one class of molecule or polymer.

In the case of polypeptides or modified polypeptides which serve as mass tags it is to be understood that a relatively small peptide (e.g. an octamer, N=8) can provide sufficient number of sequences to provide sufficient unique masses to satisfy even a large-library of 100,0000 different proteins (20N=~25×109). In practice, the number of viable sequences depends on the mass resolution of the MALDI-MS instrument which is often better than 0.1 daltons in the mass range measured. In addition, any degeneracy in the molecular weight of the mass tags can be decoded using the ability of MALDI-MS to sequence small peptides (<5,000 MW), commonly know as MS-MS-TOF. Additional "fine-tuning" of masses can be accomplished by modification of the mass-tag such as the addition of fluorescent labels.

As shown in FIG. 22, multiple-mass tags can be deployed on each bead to determine the identity of the attached protein (red), the sample being screened in cases where multiple samples are scanned (sometimes referred to as bar-coding) (purple) and the presence of an interacting antibody indicating a positive hit or biomarker (green). Since, as described above beads have been already selected by fluorescence scanning an the pico-well slide, this last mass-tag serves to reduce false-positives ensuring higher accuracy for biomarker selection.

A single mass tag of sufficient length or multiple mass tags can be used to code a bead set which is contacted with a solution of prey molecules from a set of multiple solutions in order to determine the presence of prey molecules in each solution. In this case, solution 1 containing a set of prey molecules is mixed with beads coded with mas tags that are unique for that set of bait molecules and solution 2 containing a different set of prey molecules is mixed with the beads coded with a different mass tags that uniquely coded that set of bait molecules. The beads from these two steps after contact with the respective solution 1 and 2 containing prey molecules are then mixed together and used to form a random array. The fact that different sets of mass tags are used to code the two sets of beads allows the prey from solution 1 which interact with bead set 1 and the prey from solution 2 which interact with bead set 2 to be uniquely determined. It will be understood by those familiar with the barcoding approach applied in genomic DNA sequencing that such an approach will allow prey interaction with bait to be determined uniquely for a large set of samples.

Photocleavable Linkers for Mass Tags

In some embodiments where mass-tags are attached to beads for identification of bait and/or directly to prey molecules, the mass tags do not need to be directly covalently linked to the bead surface or prey molecule but instead bound through a binding agent such as an antibody-polypeptide interaction (e.g. Experimental Example 3). However, this is non-ideal since stringent wash steps can result in partial removal of the tags (as observed during the course of some our experiments). One solution to this problem is covalently attached mass-tags which are photo-released upon exposure to UV-light. Alternatively, a near-covalent strength linkage between (strept)avidin and biotin ($Kd=10^{-15}$) can be used in conjunction with a photocleavable linker (e.g. Experimental Example 5).

AmberGen has developed a novel class of photocleavable linkers (PC-Linkers) useful in a variety of applications such as photocleavage assisted molecular purification, tRNA-mediated protein engineering, photo-activation of compounds, biomolecules and viruses as well as photocleavable mass-tagging for multiplexed assays [Olejnik, Krzymanska-Olejnik et al. (1996) Nucleic Acids Res 24: 361-6; Olejnik, Krzymanska-Olejnik et al. (1998) Nucleic Acids Res 26: 3572-6; Olejnik, Ludemann et al. (1999) Nucleic Acids Res 27: 4626-31], In the case of mass-tagging of the proteomic bead-library, a short peptide with 7 or 8 amino acids is linked to the beads via a photocleavable linker. Note that previous experiments have demonstrated that AmberGen's PC-Linker is rapidly photocleaved with 95% efficiency is less than 10 minutes using a low-intensity commercial black-light [Olejnik, Ludemann et al. (1999) Nucleic Acids Res 27: 4626-31].

Figure 5:
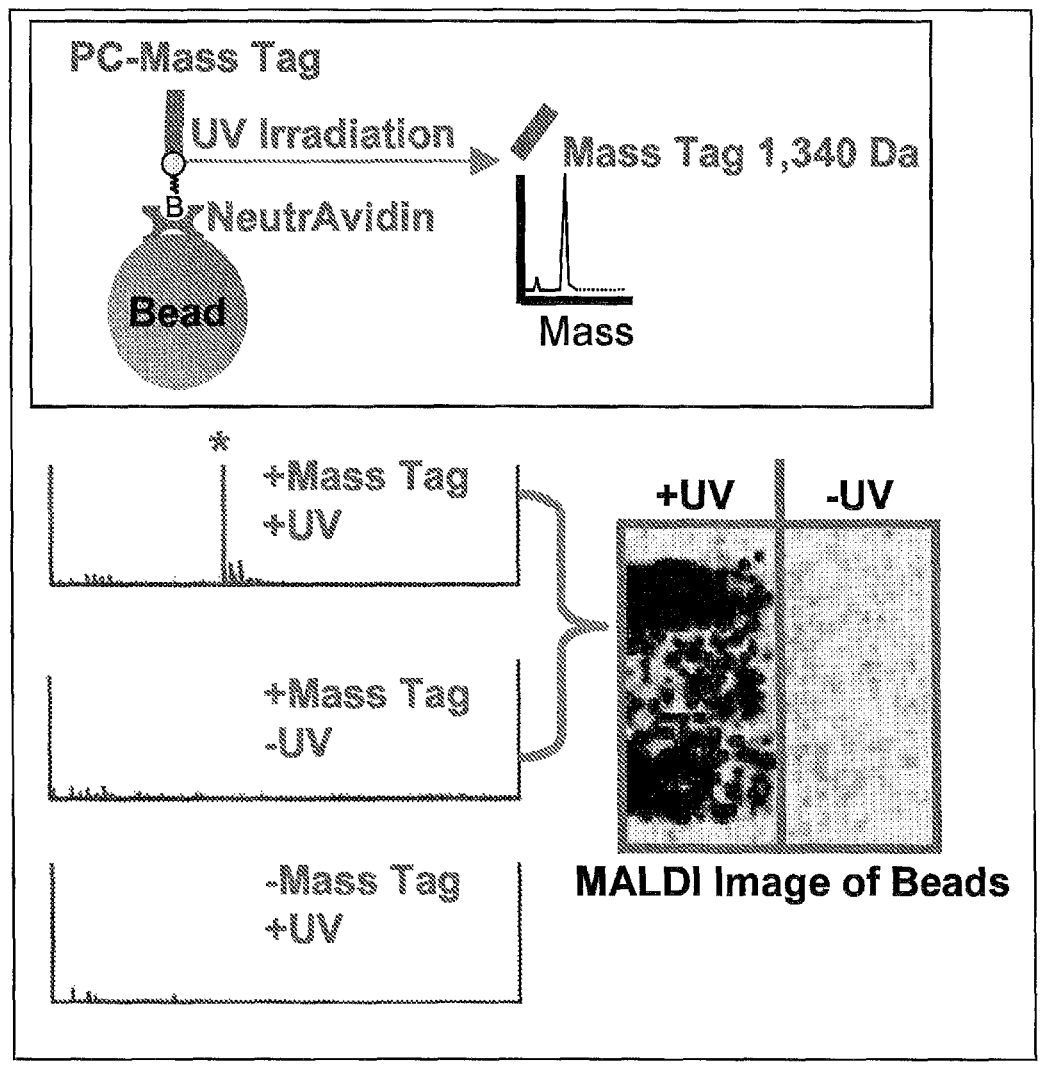

In one embodiment of the invention PC-Mass-Tags for protein identification are attached to beads in either one of 2 ways as illustrated in FIG. 23 and detailed below:

Ultra-High Affinity Biotin-(Strept)Avidin: Peptide mass-tags modified at the N-terminus with AmberGen's photocleavable biotin are attached to (strept)avidin coated beads (see FIG. 29 for attachment options of the cell-free expressed proteins). This mass-tagging method has already been demonstrated in the Experimental Examples (FIG. 5).

Direct Covalent: Using the primary amine-reactive NHS chemistry on the uncoated agarose beads, peptide mass-tags bearing an N-terminal photocleavable primary amine moiety will be chemically attached simultaneously with the attachment of the protein capture element (e.g. capture antibody). This is highly analogous to AmberGen's phosphoramidite technology distributed through Glen Research Inc. for introducing a photocleavable primary amine at the 5' end of DNA [Olejnik, Krzymanska-Olejnik et al. (1998) Nucleic Acids Res 26: 3572-6]. For this method, peptide mass-tags lacking lysines (reactive primary amine on side chain), or where lysines are blocked on the ε-amine, will be used to avoid non-cleavable attachment to the NHS-activated agarose beads.

A library of peptides pre-screened by mass spectrometry could be obtained by commercial synthesis from a variety of available vendors such as Mimotopes (Austria), Peptide 2.0 Inc. (Chantilly, Va.) or GenScript Inc. (Piscataway, N.J.) and used to create the mass-tags which will be photocleavably linked to the beads. High throughput peptide synthesis services are available from these vendors (e.g. soluble peptide arrays in 96-well plates) and peptides can be purchased with full HPLC and mass spectrometry quality controls. Conventional solid-phase chemical peptide synthesis begins at the C-terminus and ends at the N-terminus. The growing peptide is tethered to the solid-phase synthesis resin via its C-terminal carboxyl group, exposing its N-terminal amine (after deprotection) and allowing sequential attachment of another N-terminal blocked amino acid precursor (again followed by deprotection). Thus, the attachment of N-terminal modified PC-Biotin or PC-amine (amine protected) amino acid precursors at the final cycle of synthesis is a relatively strait forward process.

We have calculated that due to the high analytical sensitivity of mass spectrometry (attomoles), even adding 10 fmoles per bead of mass-tags (10-mer), the aforementioned peptides with N-terminal PC-Linker modification and all quality control data will add only pennies (¢10) to the cost of an entire proteome-bead library.

In addition to PC-Mass-Tags attached to the beads for identification purposes, Bead-GPS™ utilizes PC-Mass-Tags attached to the probes used to query the proteome library. In the case of autoantigen discovery, the PC-Mass-Tag is attached to the anti-human IgG secondary antibody used to detect the bound serum autoantibody. In this case, only one species of unique mass-tag is required. This has already been demonstrated in Experimental Example 7 (FIG. 7) using PC-Biotin. In one embodiment, custom reagents can be synthesized to allow direct covalent labeling of probes (e.g. antibodies) with PC-Mass-Tags (FIG. 24;).

Mass-Tag Decoding

In general, a requirement of mass-tag decoding is that each mass-tag peak must correspond to the correct molecular weight predicted by the mass tag molecular structure such as for example a given polypeptide sequence plus any modifications or isotope labeling within the resolution of the spectrometer in the specific mass range (~0.1 Da in 600-4,000 Da range).

It is highly desirable that each mass-tag peak must have a signal-to-noise ratio of at least 50:1, although lower signal-to-noise is sufficient for some applications. For comparison, the signal-to-noise ratio of single prototype mass-tags attached to beads incorporated into ordered arrays as described in the examples are routinely greater than 250:1 using a set of standard mass spectral parameters. Note that the signal-to-noise ratio in all experiments is determined using the ABI4800 software, which measures the integrated target peak intensity and ratios this to the integrated intensity of a nearby background region which exhibits no detectable peaks.

Importantly, spectral resolution and mass accuracy of the ABI 4800 Plus MALDI-TOF-TOP analyzer is sufficient to unambiguously identify peptides separated by as little as 0.1 Da. However, one potential problem is the appearance of several peaks for each peptide in the mass spectra, which are separated by 1 Da (the "isotope envelope"), due to the presence of small amounts of mass-shifted C13 and N15 atoms in the protein sequence. In the case of two mass tags separated by only a few Daltons, the spectral overlap may affect the tag identification. This will be addressed by using, in real-time, a spectral processing routine called peak de-isotoping. The routine, which is built-in into the ABI 4800 data acquisition software, replaces multiple peaks in the isotope envelope with a single mono-isotopic peak (corresponding to the sequence containing only C12 and N14 atoms).

MALDI-MS Imaging Software

The MALD-MS imaging of individual beads described in this invention require software to analyze data and to identify mass-tags on individual beads. There are a variety of software packages available commercially for this purpose. As an example, we have utilized BioMap in the Experimental Examples, which is a powerful biomedical image analysis software package supporting various data types generated by optical, PET, CT and mass-spectrometry based imaging. The BioMap platform allows visualization and storage of large volumes of data including experiment-specific information such as scan ID, experimental protocol and sample history. It is also a flexible tool that can be easily modified to accommodate a specific requirement. It is contemplated that as part of this invention improved imaging of individual beads and mass-tags can be made that is designed for MALD-MS bead-imaging workflow, such as automated co-registration of fluorescent and MALDI-MS scan images and identification of positive "hits" based on the detection of PC-Mass Tags.

Automation

In general, mass spectrometry and MALDI-MS in particular have proven to be highly amenable to high throughput applications in both clinical and basic research settings. For example, Sequenom Inc. has established MALDI-MS as an effective technique in the field of genotype profiling, and is providing diagnostic products in this area. As a second example of automation of mass spectrometry in clinical diagnostics, the Pediatrix Medical Group, the largest provider in the US for neonatal blood tests, uses tandem array mass spectrometry to detect metabolic disorders and has screened over 2 million babies using this method.

In the case of this invention, many improvements are envisioned which can facilitate automation and high throughput biomarker discovery. For example, multiplexing can be achieved at several stages including during the preparation of the bead library and in bar-coding multiple sample. Importantly, the use of a highly automated mass spectrometer such as the ABI 4800 Plus MALDI-TOF MS or the more advanced ABI 5800 will also facilitate high throughput analysis at the MALDI-MS bead scanning stage. For example, this system uses advanced software designed for automated scanning of a two-dimensional area, data collection and spectral processing. The ability to automatically scan approximately 10,000 beads in the pico-well MALDI plate in one hour is possible. Use of the ABI 5800 should reduce this time to $\frac{1}{10}$ (6 minutes). Furthermore, using one of the commercially available plate-loading robots will allow use of the instrument in the operator-free mode, 24 hours a day. As an example of automation levels achievable with MALDI, Sequenom, Inc. has introduced a MALDI-based system for SNP analysis which is capable of analyzing 100,000 genotypes per day.

In Situ Mass-Fingerprinting of Proteome Bead-Arrays

Figure 9:
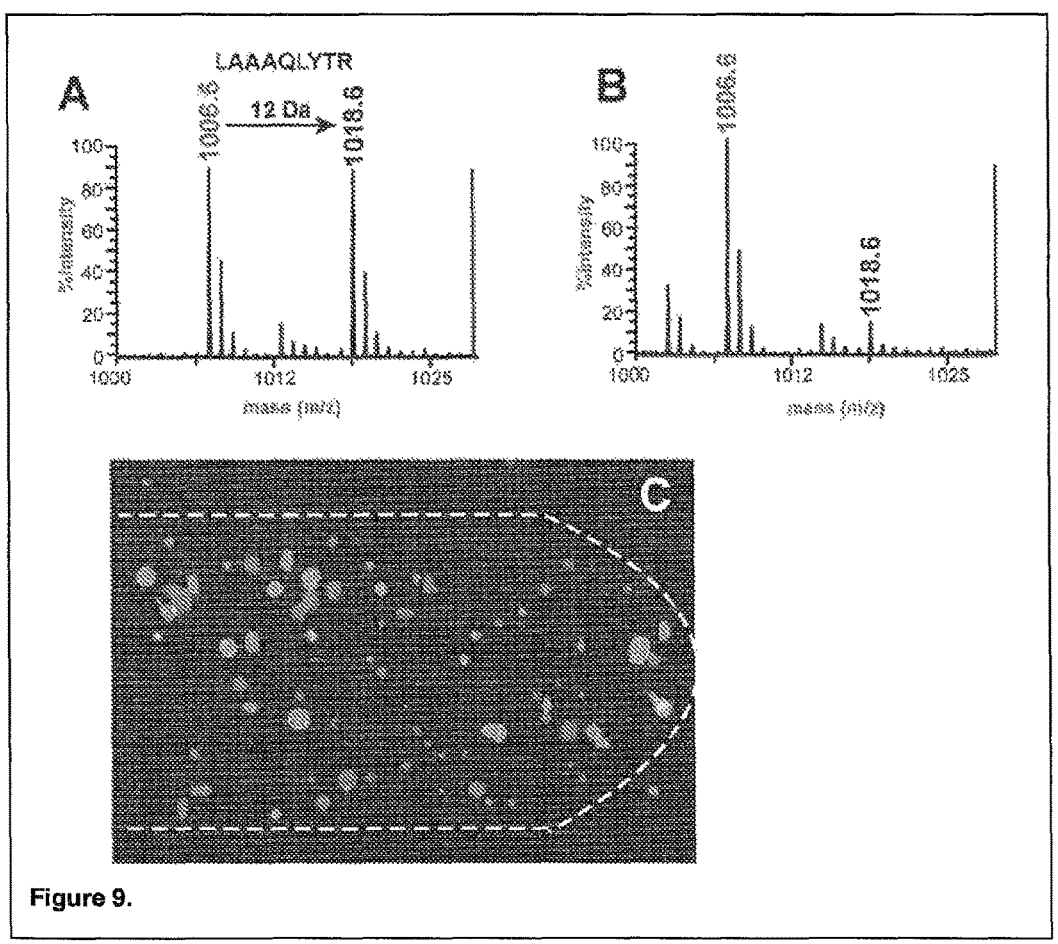

Rather that the addition of exogenous mass-tags, or any other tags, it is possible to utilize the bead-bound cell-free expressed human proteins themselves as identification codes. Analogous to mass spectrometry based on mass-fingerprinting used in classical proteomics, proteins are digested with protease (e.g. trypsin) and the resultant peptide "fingerprint" used for protein identification. If necessary, the peptides are further fragmented in the TOF/TOF tandem mass spectrometer and sequenced using the standard capabilities of today's instruments. We have explored this possibility using in situ trypsinization of protein-bead arrays in the pico-well plates. In the experiment shown in FIG. 31, human p53 and GST A2 beads were produced using the aforementioned methods (antibody-mediated C-Tag capture; 75-100 micron beads in this case). Following deposition into a MALDI plate, the beads were sprayed with an ultra-fine mist of trypsin solution and allowed to digest in a humidified chamber. The reaction was stopped by spraying on the MALDI matrix solution (denaturing). Individual beads were then imaged by MALDI-MS. In this case, MALDI images were generated based on single identifying tryptic fragments (confirmed by tandem MS/MS sequencing) corresponding to the p53 and GST proteins. See also Experimental Example 9 (FIG. 9A-C).

Application to Detection of Genetic Mutations Using MALDI-MS-Imaging, Mass Tags and Arrays of Beads One embodiment of this invention is directed towards the multiplex detection of mutations which might exist in multiple regions of single genes or multiple genes. In order to detect such mutations, a nascent protein or polypeptide (typically a portion of a gene product, wherein the portion is between 5 and 200 amino acids in length, and more commonly between 5 and 100 amino acids in length, and more preferably between 5 and around 60 amino acids in length—so that one can work in the size range that corresponds to optimal sensitivity on most mass spectrometry equipment) is (in one embodiment) first synthesized in a cell-free or cellular translation system from message RNA or DNA coding for the protein which may contain a possible mutation. The nascent protein or polypeptide is then separated from the cell-free or cellular translation system using an N-terminal (located at or close to the N-terminal end of the protein) which is designed to bind to a binding agent on the surface of a bead. For example, the C-terminal epitope can consist of an HSV sequence as discussed here and binding agent on the bead consists of an anti-HSV directed antibody. A C-terminal epitope is not used to avoid the case of chain truncating mutations which would eliminate this epitope.

This process as described above can then be repeated to examine additional sequences in a given gene or multiple genes. In cases where genomic material is used this may be necessary in order to span whole exons or pieces of exons such as in the BRCA1 or BRCA2 gene which contains over 50 exons. Alternatively, different sequences in different genes may wish to be examined in the case for example of a tumor where multiple oncogenes may be suspect. Thus, using the methods described in this invention, a library of beads will be formed each one containing a sequences derived from different gene sequences and also containing unique mass tags coding that particular type of bead. In this case, the sequence interrogated on the individual bead may be a mixture of wild-type sequence and mutant sequences derived from the same region of the gene interrogated.

The resulting isolated material (which may contain both wild-type and mutant peptide sequences) is then analyzed by mass spectrometry consisting of the measurement of individual beads which are part of a bead array. Detection of a peak in the mass spectrum with a mass correlating with the expected wild-type peptide indicate the wild-type peptide. Detection of a peak in the mass spectrum with a mass not correlating with the wild-type peptide indicates a mutation.

It is important to note that in this example, the mass of the wild-type sequence and the resulting peak it produces from an individual bead serves the role of a mass-tag, e.g. it allows one to identify the bait species captured on the bead. The presence of a mutation is then identified by the additional peaks from the bead which do not correspond to the wild-type species. For example, a missense change of a wild-type sequence which corresponded to a codon shift from TAT to TCT would result in the substitution of a Tyr with a Ser and a subsequent mass shift of +176 daltons. It will be understood by those practiced in the art of mass spectrometry that advanced systems are able to distinguish much small shifts even below 1 dalton so almost all substitutions can be detected. Furthermore, MS-MS techniques allow sequencing of the peptides to resolve any ambiguity if the wild-type peptide is not unambiguously identified by its mass. In some embodiments it may be advantageous to also code the bead containing a particular polypeptide species using mass tags as described extensively in this invention. For example, in this embodiment the molecules capture with a binding agent on the bead surface consist of nascent proteins or polypeptides synthesized in a cell-free or cellular translation system from message RNA or DNA coding for the region which may contain a possible mutation. Furthermore, the nascent proteins produced in the cell free reaction could be added in separate reactions to a particular mass-tagged bead as described previously under parallel method or formed using the batch techniques described before.

It is to be understood that the protein bead library used in this embodiment could be formed using the Parallel Synthesis methods described previously or the Batch Synthesis methods described previously. In the Parallel Synthesis methods each protein or polypeptide sequence is synthesized using PCR and cell-free synthesis in separate reactions and the resulting proteins added to individual suspensions of beads whereas in the Batch Preparation method, the entire library can be formed in two multiplex reactions. In either case, the overall library is randomly arrayed and the individual beads measured using mass spectrometry.

Photocleavable DNA-Tags

In addition to peptide based decoding of the proteome-bead library, we have developed an alternative method of coding individual beads based on the use of PC-DNA-Tags. Such tags are also based on proprietary photocleavage technology developed by AmberGen (see U.S. Pat. Nos. 5,948,624; 5,986,076; 6,589,736; 7,312,038; 7,339,045; 7,211,394; 6,057,096; 6,218,530; 7,057,031; 7,195,874; 7,485,427; 7,547,530) which offers convenient synthesis of DNA molecules with a 5'-modification consisting of a photocleavable linker such as PC-aminotag-phosphoramidites commercially distributed by Glen Research Inc (Sterling, Va.). These tags can be directly linked to the activated agarose beads similar to the method used for PC-Mass-Tags and released upon exposure to near-UV light. Once removed from individual positive beads, these PC-DNA-Tags can be rapidly decoded and quantified in bulk using a massively parallel PCR platform.

One embodiment of this invention involves use of photocleavable DNA-tags to code and decode beads. As an example, solid-phase (bead) PCR with universal photocleavably attached primers, can be used to separately amplify various human ORF plasmid inserts on a 34 micron agarose beads; thus creating photocleavably tethered DNA amplicons (pure species on each bead). Several different DNA-bead species are then pooled at various ratios and then photocleaved.

Figure 10:
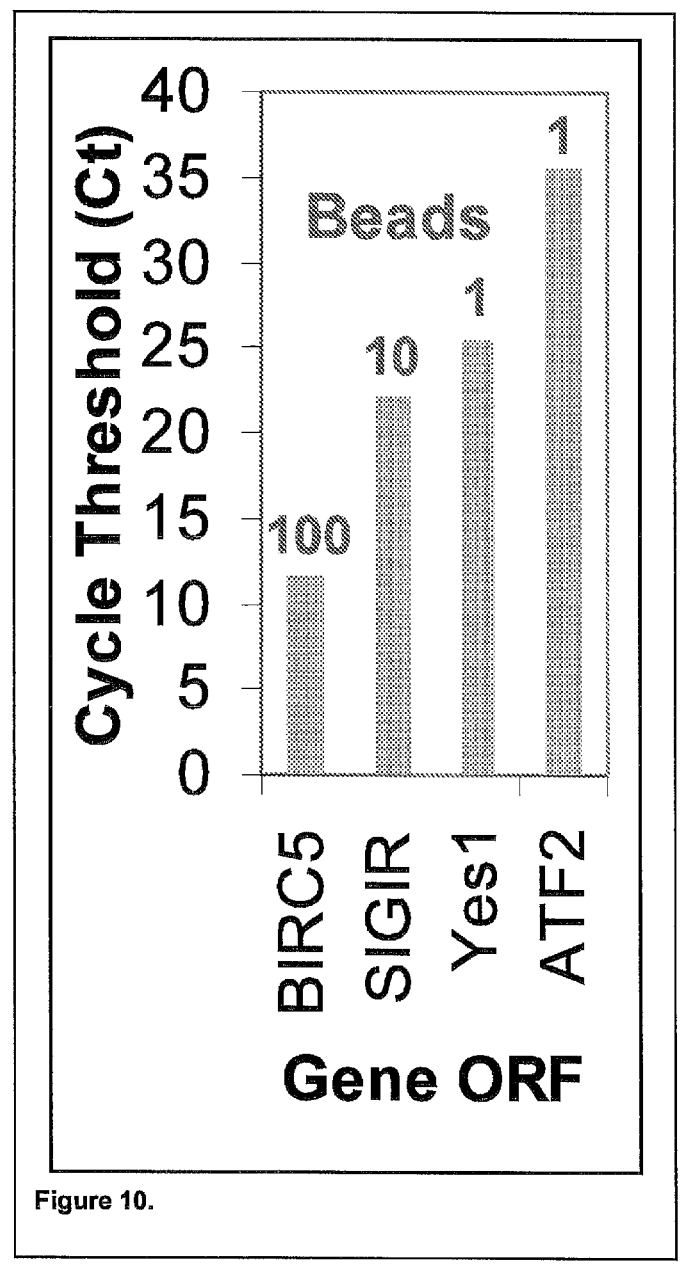

The photo-released DNA is then analyzed on a suitable instrument which can detect the DNA-tags such as a standard DNA hybridization chip (e.g. DNA microarray) or an RT-PCR device. In the case of DNA hybridization chips, many chips are available such as from Affymetrix which have probes for thousands of genes that can be used to detect the release of specific DNA sequences photoreleased from the beads. Commercial prototypes have also been introduced such as by WaferGen Inc. that can simultaneously analyze large numbers of such PC-DNA tags. In one example, a 5,000-member prototype RT-PCR chip was used containing probes to all members of the test bead library evaluated. As shown in FIG. 10 (Experimental Examples), gene ORFs were positively identified from as little as a single bead, with Cycle Threshold (Ct) values approximately following the bead numbers.

Importantly, attachment of PC-DNA-tags is fully compatible with the Parallel protein-bead library production methods described above. Photocleavage of the individual beads and collection of DNA-tags from positive beads can be easily accomplished almost simultaneous with fluorescent scanning (i.e. bead selection step) by using a modified fluorescence microarray scanner. In particular, a laser normally used for scanning the image can be replaced with a laser capable of photocleavage of DNA from individual beads such as a pulsed Nd-Yag laser with 355 nm output which are widely commercially available at low cost. It has been demonstrated by us that such lasers can photocleave >90% of the tags on a bead sample in less than a few seconds. Since commercial fluorescent scanners operating with multiple wavelengths and different lasers are designed to perform sequential scans maintaining image registration, software image identification of positive beads would allow the Nd-Yag laser to be switched on to expose only positive beads during a sequential registered scan. Scan resolution is normally 3-5 μallowing high precision for Nd-Yag laser beam to photocleave DNA-tags from 35 beads located in the pico-well plate. Alternatively a scanner using a CCD imager along with a photocleaving laser can be readily used to selectively remove DNA-tags from specific beads identified as positive in the fluorescent scan. Photocleaved DNA-tags can be collected in a thin fluidic chamber overlaying the array for subsequent decoding. Importantly, selection of the positive hits is simplified for this approach since the imaging and photo-release are done simultaneously in the same instrument.

Importantly, both the in situ trypsinization and PC-DNA based decoding approaches are also fully compatible with the Batch method of protein-library construction described earlier which involves single-molecule solid-phase emulsion PCR to create a bead-sorted library of expressible DNA in a single reaction, which is then converted to a bead-sorted library of in vitro expressed proteins in a single self-assembling cell-free protein synthesis reaction.

EXPERIMENTAL

Example 1. Affinity Purification of Cell-Free Expressed Peptides onto an Agarose Bead Affinity Resin Followed by Mass Spectrometry Detection from Single Beads In this Example a test peptide corresponding to a segment of the APC gene, with an expected molecular weight of 6,203 Da, containing an N-terminal FLAG® epitope tag (Sigma-Aldrich, St. Louis, Mo.), was synthesized in a recombinant cell-free transcription/translation reaction according to the manufacturer's instructions (PureSystem; Post Genome Institute Co., LTD., Japan).

The nascent peptide from the reaction was then purified on mouse anti-FLAG antibody-coated agarose affinity beads (~75-150 micron diameter). For this, the crude cell-free expression mixtures were diluted with 50 μL of AB-T [100 mM ammonium bicarbonate with 0.1% Triton X-100 (v/v)]. Mouse anti-FLAG antibody coated agarose affinity beads were used in batch mode to purify the cell-free expressed peptides (EZview™ Red Anti-FLAG® M2 Affinity Gel, Sigma-Aldrich, St. Louis, Mo.). The diluted crude cell-free expression mixtures were combined directly with ~1 μL beads in 0.5 mL polypropylene PCR tubes. The mixtures were then incubated for 20 minutes at room temperature with gentle mixing to keep the beads suspended. The beads were then spun down in a micro-centrifuge (~16,000× g) and the fluid supernatant removed and discarded. The beads were then washed 2×10 min each in mass spectrometry grade water (MSG-Water), removing the fluid supernatant as before. After removing the final wash, beads were re-suspended in 50 mL MSG-Water and individual beads were selected from suspension by careful pipetting and deposited onto a stainless steel plate for matrix assisted laser desorption ionization time-of-flight mass spectrometry (MALDI-TOF or MALDI-MS). A small volume (0.2-0.5 μL) of MALDI-TOF matrix solution (20 mg/mL sinapinic acid matrix in 50% acetonitrile and 0.1% trifluoroacetic acid) was immediately applied directly on top of the beads. The droplet was then allowed to dry/crystallize under ambient conditions without disturbance. The size of the final spot was approximately 2 mm in diameter with the beads near the center of spot. Once completely dried, the spots were analyzed using a Voyager-DE MALDI-TOF mass spectrometer (Applied Biosystems; Foster City, Calif.). The MALDI-TOF spectra were acquired on the outer edge of the spot, inside the spot in the immediate vicinity of the beads and also directly from the beads.

Results.

FIG. 1 shows that the peptide was observed at the correct mass of 6,203 Da (mass includes N-terminal formylation produced in the cell-free expression system). These data confirm that the amount of peptide that can be bound to single agarose beads of roughly 100 microns in diameter, is sufficient to be detected by MALDI-TOF mass spectrometry. This is consistent with the reported capacity of the agarose beads, which at >100 ng/μL beads and approximately 1,000 individual beads per μL bead volume, would amount to approximately 20 femtomoles of a 6,000 Da peptide. This falls within range of the sensitivity of MALDI-TOF mass spectrometry. The signal intensity was typically higher near the beads, although the matrix solution can elute peptides from the beads resulting in peptide spreading prior to drying of the matrix solution spot.

Example 2. Mass Spectrometry Readout and Mass-Imaging from Individually Resolved Beads In this Example, two test peptides with molecular weights of 3,483 Da and 3,287 Da, each containing an N-terminal FLAG® epitope tag (Sigma-Aldrich, St. Louis, Mo.), were separately synthesized in a recombinant cell-free transcription/translation reaction according to the manufacturer's instructions (PureSystem; Post Genome Institute Co., LTD., Japan). The nascent peptides from each reaction were then separately purified on mouse anti-FLAG antibody-coated agarose affinity beads (EZview™ Red Anti-FLAG® M2 Affinity Gel, Sigma-Aldrich, St. Louis, Mo.) (~75-150 micron diameter). The beads were then mixed in a 9:1 ratio and manually deposited in a random pattern on a suitable substrate for MALDI-TOF mass spectrometry. The MALDI-TOF matrix (CHCA) was sprayed on in a thin and uniform film and allowed to dry. MALDI-TOF imaging of the surface was performed using an ABI 4800 Plus MALDI-TOF/TOF mass spectrometer (Applied Biosystems; Foster City, Calif.). The surface of the substrate was scanned with the instrument's laser, in the instrument's reflector mode, in the 1,500-4,000 m/z (mass/charge) spectral range and two images were constructed using spectral intensity at the m/z corresponding to the molecular weight of the peptides.

Figure 2:
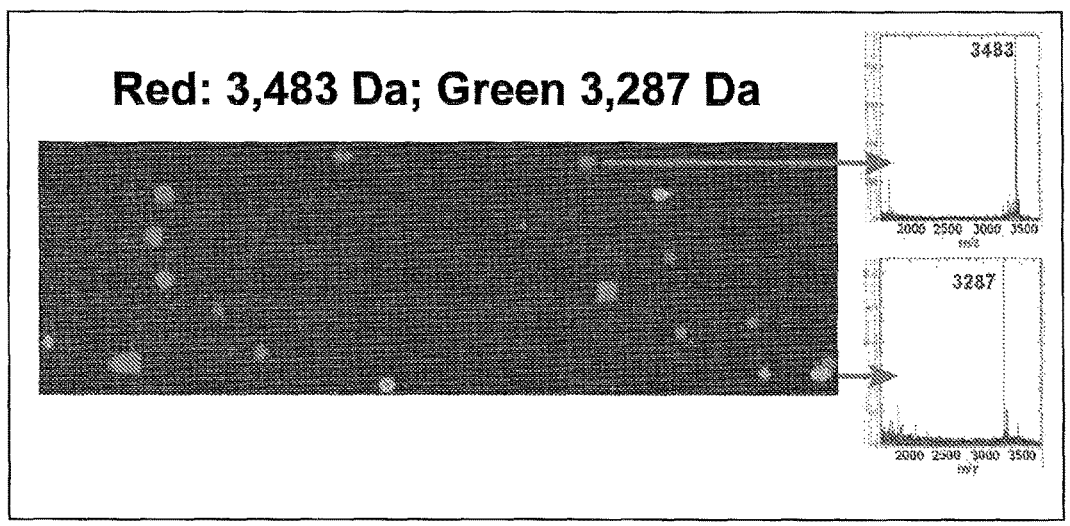

Results:

A two-color image overlay was created from the two mass-images of the beads that were constructed using the spectral intensity at the m/z corresponding to the molecular weight of the two test peptides (FIG. 2). Two distinct and resolved populations of beads are visible on the substrate, with the ratio of the two bead species in the mass-image being in excellent agreement with the mixing ratio. The spectral analysis of each spot reveals a single strong MALDI-TOF peak, indicating that each bead carries a homogenous population of one peptide. This work verifies the ability of MALDI-TOF mass spectrometry to scan and image individual beads that carry compounds (peptides in this embodiment) detectible by their unique mass.

Example 3. Mass Spectrometry Readout and Mass-Imaging from Individually Resolved 34 Micron Beads Deposited in Pico-Well Plates: Mass-Tagging of Analyte-Bearing Beads for Identification In this Example, 34 micron agarose beads were conjugated to an antibody directed against the HSV epitope tag. The beads were then loaded with different recombinant proteins bearing this HSV epitope tag. The beads were additionally bound to one of three different peptide "mass tags" of unique mass, corresponding to the HSV peptide epitope itself, conjugated on the N-terminus to different fluorophores. The beads were then deposited into a special pico-well plate and mass-imaged by scanning MALDITOF mass spectrometry. Separately, the presence of the recombinant proteins was detected on the same batch of beads by probing with a fluorescently labeled antibody directed against the common VSV-G epitope tag, also present in the recombinant proteins.

Development of Pico-Well Plates for MALDI-TOF Bead Scanning

In order to create mass images of beads or particles, it may be advantageous to randomly array the beads in a regular two-dimensional grid, similar to spots in a conventional microarray. This maximizes bead density, yet assures bead separation, and allows the MALDI-TOF instrument to efficiently and rapidly move from one bead to another, for optimal scan speed. Furthermore, in order to maximize bead resolution, it may also be advantageous to contain each bead in its own microscopic well. Finally, cross-platform imaging of the beads, such as by mass spectrometry and fluorescence, may be advantageous in certain embodiments of the technology.

For this purpose, we developed a novel dual-use pico-well substrate suitable for both mass spectrometric and light based analyses. This substrate, whose overall dimensions are 75.0 mm long by 25.0 mm wide and 1.0 mm thick, is sliced from a fiber optic bundle (block of fused optic fibers) and fabricated by the etching of 44 micron diameter by 55 micron deep pico-wells (i.e. picoliter scale volume) at the ends of the optical fibers that are positioned 50 microns from center-to-center in a hexagonal ordered array (Incom Inc., Charlton, Mass.). The result is >0.5 million wells in the dimensions of a standard microarray or microscope slide (75×25×1 mm). The design allows deposition of only one bead per well, but maximum access of the MALDI-TOF laser beam to vaporize the matrix coating the bead and allow mass analysis. Since the array is fabricated from a fiber optic bundle, it also forms a face-plate for convenient measurement of light based signals, for example fluorescence or luminescence from each bead (each well) using direct-contact CCD cameras or by using conventional fluorescence microarray scanners.

Preparation of Anti-HSV Antibody Coated 34 Micron Agarose Affinity Beads

34 Micron diameter agarose beads were conjugated to an anti-HSV tag antibody for later use in capturing peptides bearing this epitope tag. To do so, an anti-HSV monoclonal antibody (EMD Biosciences, Inc., San Diego, Calif.) was diluted to 0.5 mg/mL in a final buffer of 200 mM sodium bicarbonate and 200 mM NaCl (Binding Buffer). 6% cross-linked NHS-activated 34 micron agarose beads (NHS HP SpinTrap, GE Healthcare Life Sciences, Piscataway, N.J.) were washed 4× in several bead volumes of ice cold 1 mM HCl. Beads were then reacted with the anti-HSV antibody solution at a ratio of 6 µg of antibody per each µL of actual bead volume for 1 hour with gentle mixing.

Beads were then washed 1× briefly and 2× 30 min with several bead volumes each of 200 mM glycine and 1 mM EDTA in Binding Buffer. Beads were then washed 2× 5 min in Binding Buffer, 2× 5 min in 10 mM Tris, 1 mM EDTA, pH 8 with 200 mM NaCl, and ix briefly in 10 mM Tris, 1 mM EDTA, pH 8 with 50 mM NaCl. Beads were then prepared to a 20% (v/v) suspension in 10 mM Tris, 1 mM EDTA, pH 8 with 50 mM NaCl and stored at +4° C.

Preparing Modified HSV Peptide Mass Tags of Different Mass

Peptides of unique mass were prepared by chemical modification with different fluorophores of the HSV-Tag peptide (KQPELAPEDPED), which was purchased from Sigma-Aldrich (St. Louis, Mo.). To do so, the peptide was prepared to 5 mg/mL in 100 mM sodium bicarbonate and reacted overnight (with mixing) with equimolar amounts of the Cy3-NHS or Cy5-NHS activated (primary amine reactive) fluorescent dye labeling reagents (GE Healthcare Life Sciences, Piscataway, N.J.). Peptides were used without further purification (MALDI-TOF analysis showed that the peptides were almost exclusively labeled at a ratio of 1 dye per peptide molecule). Because the NHS activated labeling reagents react only with primary amines, selective labeling of the N-terminal lysine is anticipated. The unlabelled as well as Cy3 and Cy5 labeled HSV peptides provided three species of unique mass tags, 1,368 Da, 2,048 Da and 2,074 Da respectively, which were used in subsequent steps.

Binding of Recombinant Proteins and HSV Peptide Mass Tags to the Anti-HSV Agarose Affinity Beads Human p53 and human KLHL12 were expressed recombinantly in a cell-free reaction. Expression reactions were performed using a transcription/translation coupled rabbit reticulocyte lysate system (TNT® T7 Quick for PCR DNA; Promega, Madison; WI) according to the manufacturer's instructions. The expression plasmid used was a derivative of the pETBlue-2 vector (EMD Biosciences, Inc., San Diego, Calif.) containing a C-terminal polyhistidine (HHH-HHH) and HSV epitope tag (QPELAPEDPED) as well as an N-terminal VSV-G epitope tag (YTDIEMNRLGK) flanking the Open Reading Frame (ORF) inserts of human p53 or human KLHL12. A parallel negative control expression reaction was performed lacking only the plasmid DNA.

After the expression reaction, the nascent proteins were isolated onto the aforementioned anti-HSV antibody coated agarose affinity beads. Protein isolation onto the beads was performed in batch mode using 0.45 micron pore size, PVDF membrane, micro-centrifuge Filtration Devices to facilitate manipulation of the small volumes of affinity beads and exchange the buffers (Ultrafree-MC Durapore Micro-Centrifuge Filtration Devices, 400 µL capacity; Millipore, Billerica, Mass.). Filtration Devices were used unless otherwise stated. For each sample (1 Filtration Device per sample), 1 µL packed bead volume (~30,000 beads) was washed briefly 4× 400 µL with TBS [TBS=50 mM Tris (2-amino-2-(hydroxymethyl)-1,3-propanediol) pH 7.5 and 200 mM NaCl] and then 2× 400 µL briefly with high purity Molecular Biology Grade Water (MBG-Water). Washed bead pellets were then re-suspended at a ratio of 50 µL of crude expression reaction per µL packed bead volume (~30,000 beads) and mixed for 30 min to capture the target nascent recombinant protein. Beads were then washed briefly 3× 400 µL with TBS-T [TBS with 0.05% v/v Tween-20] and then 1× 400 µL with Block Buffer [1% w/v BSA in TBS-T].

Next, the beads (which at this stage already contained the nascent recombinant proteins; 1 µL packed bead volume each sample) were additionally loaded with the aforementioned HSV peptide mass tags. 730 pmoles of the aforementioned HSV peptide mass tags was added to each of the three bead samples (blank, human p53 and human KLHL 12 bead samples), one unique mass tag species per bead sample, in 200 µL of Block Buffer. This corresponded to ~25 fmoles of HSV peptide mass tag added per bead. HSV peptide mass tags were allowed to bind for 30 min with mixing. Beads were then washed 3× 400 µL briefly with TBS-T, 3× 400 µL TBS and then 4× 400 µL with Mass Spectrometry Grade Water (MSG-Water).

MALDI-TOF Mass Spectrometry Imaging of Beads

As a result of the previous steps in this Example, the three mass-tagged bead species were as follows: Blank beads (no recombinant protein) coded with the unlabeled HSV peptide mass tag (1,368 Da), human p53 beads coded with the Cy3 labeled HSV peptide mass tag (2,048 Da) and human KLHL12 beads coded with the Cy5 labeled HSV peptide mass tag (2,074 Da). Next, the three bead species were pooled in equal amounts and the pooled bead population was then deposited into the aforementioned pico-well plates by brief centrifugation. MALDI-TOF imaging (scanning) of the pico-well plate was performed essentially as described in Example 2, in order to detect the HSV peptide mass tags from individual beads.

Verification of Bound Recombinant Proteins

In order to verify the presence of bound recombinant protein on the beads, an aliquot of the same batch of beads was saved after loading the recombinant proteins but before loading the HSV peptide mass tags. These beads were probed with a fluorescently (Cy3) labeled anti-VSV-G tag antibody (Sigma-Aldrich, St. Louis, Mo.) in order to detect this common N-terminal epitope tag present in all the nascent recombinant proteins. To do so, beads were probed with 200 µL of antibody diluted from the manufacturer supplied stock at 1/50 in Block Buffer. Probing was performed for 30 min with mixing. Using the aforementioned Filtration Devices, beads were then washed 4× 400 µL briefly with TBS-T and then 2× 400 µL with TBS.

Beads were then embedded in a thin polyacrylamide film on a glass microscope slide for fluorescence imaging. The acrylamide mix was prepared by mixing 487 µL TBS, 113 µL of a 40% acrylamide and bis-acrylamide mixture (19:1 ratio; Bio-Rad Laboratories, Hercules, Calif.), 1 µL of 100% TEMED (Bio-Rad Laboratories, Hercules, Calif.) and 6 µL of a 10% (w/v) ammonium persulfate solution (prepared in water). This acrylamide mix was used to resuspend the washed bead pellet to form 1% (v/v) beads. Approximately 10-20 µL of the bead suspension was placed on a standard glass microscope slide, overlaid with an 18 mm round microscope cover glass and allowed to polymerize for approximately 10 min. The microscope slides were fluorescently imaged using a GenePix 4200 laser based microarray scanner (Molecular Devices, Sunnyvale, Calif.).

Figure 3A:
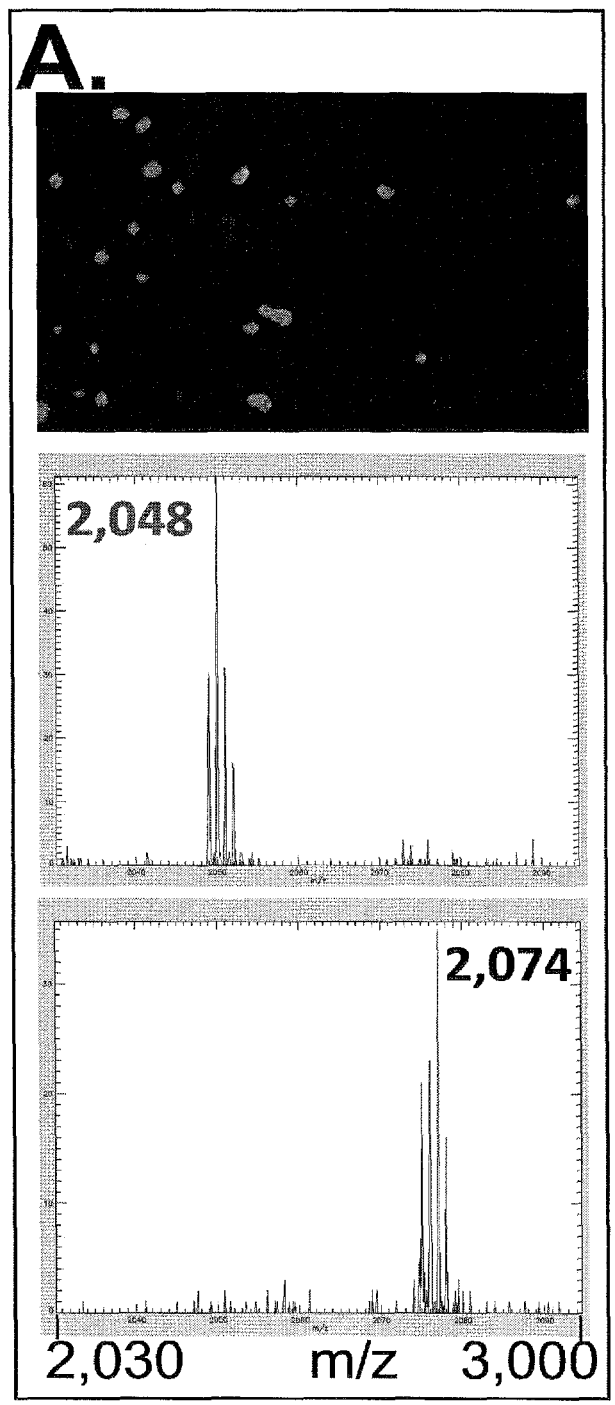
Figure 3B:
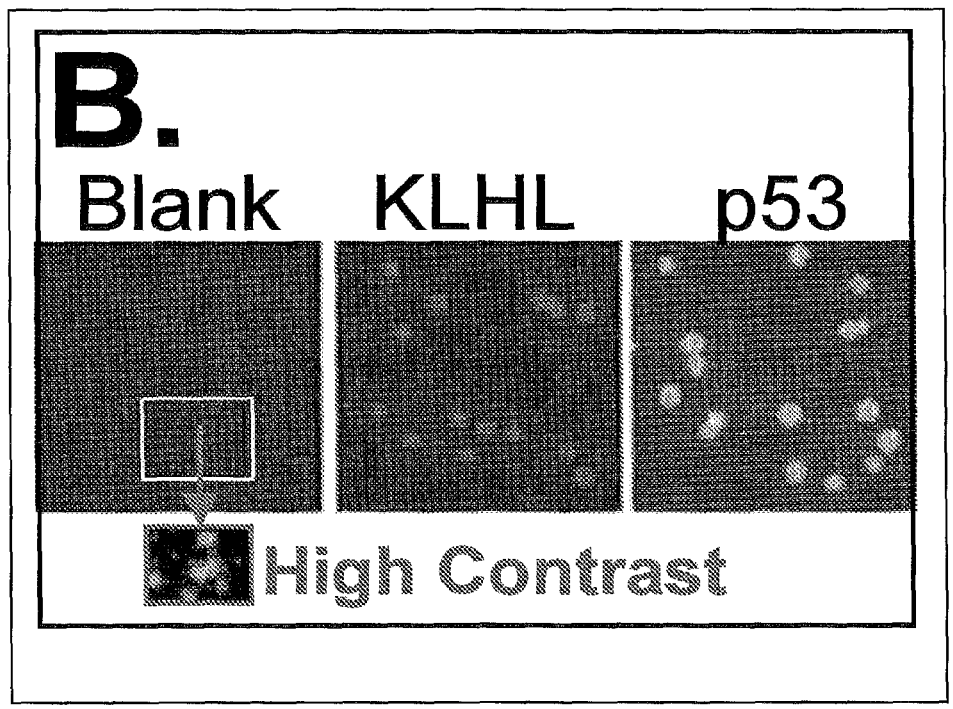

Results:

Two recombinant human proteins (p53 and KLHL), each having a common C-terminal HSV epitope tag, were expressed in a cell-free system and loaded/isolated onto anti-HSV antibody-coated 34 micron agarose beads. As a negative control, blank beads were also prepared in the same manner except only the expressible DNA was omitted from the cell-free protein synthesis reaction. After protein expression and bead-capture, each of the three bead species was additionally loaded with a unique HSV peptide mass tag having a molecular weight of 1,368, 2,048 or 2,074 Da (binding to beads again mediated by the anti-HSV antibody coating). The 3 bead species were then pooled and loaded into the aforementioned pico-well plates. For MALDI-TOF mass spectrometry, the matrix was applied as a thin and uniform film to the plate surface. The surface was then scanned in the MALDI-TOF mass spectrometry reflector mode in the 1,500-4,000 m/z spectral range. Three mass images were constructed using spectral intensity at the m/z corresponding to the molecular weight of the HSV peptide mass tags. Three distinct populations of beads are visible on the pico-well plate (FIG. 3A). The spectral analysis of each spot reveals a single strong MALDI-TOF peak, indicating that each bead carries a homogenous population of peptide mass tag. Importantly, separate antibody-mediated fluorescence detection of the expressed recombinant proteins on the beads demonstrates that in addition to the mass tags, the expressed proteins are also present with signal-to-noise ratios of 10:1 and 60:1 for KLHL and p53 respectively (FIG. 3B). This work verifies the ability of MALDI-TOF mass spectrometry to scan, image and resolve individual beads and identify different analytes on the beads (in this embodiment recombinant proteins) by virtue of co-loaded peptide mass tags.

Example 4. Synchronization of Fluorescence Image and Mass Spectrometry Mass-Image of Individually Resolved Beads In this Example, 34 micron agarose beads coated with the anti-HSV tag antibody were loaded with cell-free expressed recombinant human p53 or recombinant human KLHL12, both of which contained the HSV epitope tag; performed exactly as described in Example 3. Also as in Example 3, a parallel set of blank beads was prepared in the same manner except only the expression DNA was omitted from the cell-free reaction used to synthesize the recombinant proteins.

Beads were then loaded with different HSV peptide mass tags labeled on their N-terminus with different fluorophores in order to create unique masses; done exactly as described in Example 3.

As a result of the previous steps in this Example, the three mass-tagged bead species were as follows: Blank beads (no recombinant protein) coded with the unlabeled HSV peptide mass tag (1,368 Da), human p53 beads coded with the Cy3 labeled HSV peptide mass tag (2,048 Da) and human KLHL12 beads coded with the Cy5 labeled HSV peptide mass tag (2,074 Da). The three bead species were pooled, the pooled beads deposited in the aforementioned pico-well plates and the beads then mass-imaged with MALDI-TOF mass spectrometry exactly as described in Example 3, in order to detect the mass tags on individual beads.

After MALDI-TOF mass-imaging, the same area of the pico-well plates was fluorescently imaged using a GenePix 4200 laser based microarray scanner (Molecular Devices, Sunnyvale, Calif.).

Figure 4:
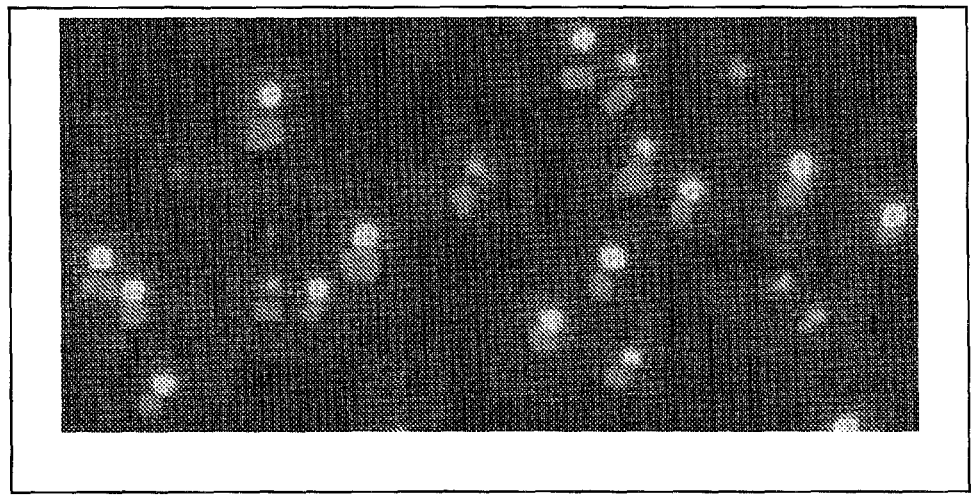

In this Example, the mass-image of the Cy3 labeled HSV peptide mass tag (2,048 Da) was overlaid (synchronized) with the fluorescence (Cy3) image of the same HSV peptide mass tag (same region of pico-well plate). Results in FIG. 4 show excellent concordance between the fluorescence and mass images. The small number of discordant beads is believed to be non-specific autofluorescence of beads lacking the peptide mass tag, imperfections in the MALDI-TOF matrix coating and/or

Example 5. Photocleavable Mass Tags—Mass Spectrometry Readout and Mass-Imaging from Individually Resolved Beads Preparation of NeutrAvidin Coated 34 Micron Agarose Affinity Beads Performed in the same manner as in Example 3 for the anti-HSV antibody coating of 34 micron agarose beads except in this case NeutrAvidin biotin binding protein (Invitrogen, Carlsbad, Calif.) was conjugated to the beads and loaded at a ratio 10 µg per µL of packed agarose bead volume (NeutrAvidin concentration at binding step was 2.5 µg/µL).

Preparation of Photocleavable (PC) Biotin Labeled Peptide Mass Tags

Performed in the same manner as in Example 3 for the N-terminal fluorescence labeling of the HSV peptide mass tags except that the target peptide was the VSV-G peptide (YTDIEMNRLGK) (Roche Applied Science, Indianapolis, Ind.) (1,340 Da) and instead of using NHS-activated (primary amine reactive) fluorescence dye labeling reagents, AmberGen's NHS-activated photocleavable (PC) biotin labeling reagent was used (AmberGen Incorporated, Watertown, Mass.) [Olejnik, Sonar, Krzymanska-Olejnik and Rothschild (1995) Proceedings of the National Academy of Science (USA) 92: 7590-7594; Pandori, Hobson, Olejnik, Krzymanska-Olejnik, Rothschild, Palmer, Phillips and Sano (2002) Chem Biol 9: 567-73].

Binding of PC-Biotin Peptide Mass Tags to NeutrAvidin Agarose Affinity Beads 250 pmoles of the aforementioned PC-Biotin labeled VSV-G peptide mass tag was added to 1.5 µL of packed NeutrAvidin agarose bead volume (~45,000 beads) in 50 µL of Block Buffer (see Example 3 for buffer compositions). This corresponds to ~5 fmoles of PC-Biotin VSV-G peptide mass tag added per bead. The PC-Biotin VSV-G peptide mass tag was allowed to bind for 30 min with mixing. Beads were then washed 3× 400 µL briefly with TBS-T, 3× 400 µL TBS and then 4× 400 µL with Mass Spectrometry Grade Water (MSG-Water).

Mass Tag Photocleavage and MALDI-TOF Mass Spectrometry Imaging of Beads

Next, the beads loaded with the PC-Biotin VSV-G peptide mass tag were then deposited into the aforementioned pico-well plates (Example 3) by brief centrifugation. MALDI-TOF imaging (scanning) of the pico-well plate was performed essentially as described in Example 2, in order to detect the VSV-G peptide mass tags from individual beads, with the following exceptions: After bead deposition but before matrix coating and MALDI-TOF imaging, photo-release of the captured mass tag was achieved via illumination of the pico-well plates for 5 min with near-UV light (365 nm peak UV lamp, Blak-Ray Lamp, Model XX-15, UVP, Upland, Calif.) at a 5 cm distance. The power output under these conditions was approximately 2.6 mW/cm$^2$ at 360 nm, 1.0 mW/cm$^2$ at 310 nm and 0.16 mW/cm$^2$ at 250 nm. For the minus light negative control (−UV), a portion of the pico-well plate was masked using an opaque solid barrier.

Results:

As demonstrated by the mass-image in FIG. 5, specific and robust VSV-G peptide mass tag signal is observed coming from individually resolved beads following light pre-treatment (+UV) to break the photocleavable biotin linkage to the NeutrAvidia agarose beads prior to MALDI-TOF mass spectrometry (MALDI-TOF mass spectrometer laser itself is inefficient at photocleaving linker). Representative mass spectra are also shown from individual beads in FIG. 5. The VSV-G peptide is observed at its correct mass (1,340 Da), confirming full photocleavage of the PC-Biotin moiety from the peptide (which restores the peptide to its native unmodified state). Very weak to no peptide signal is observed without light pre-treatment (−UV) and no signal is observed when the peptide is omitted from the beads (−Mass Tag). Note that the saturating signal observed in the light treated sample reduced the resolution of single beads by mass-imaging in this Example (although single beads are still observed). However, in the minus light permutation (−UV), the dramatically weaker signal better shows individually resolved 34 micron beads by MALDI-TOF mass spectrometry mass-imaging in the pico-well plates.

Example 6

Photocleavable Mass Tags (for Bead Identification) Co-Loaded with "Bait" Molecules for Multiplex Bioassays: "Bait" Detection and Mass Spectrometry Readout from Beads One embodiment of mass spectrometry mass-imaging of beads or particles is to load onto the beads both a mass tag for bead identification and "bait" molecules or compounds for use in multiplex bioassays. In this Example, beads are co-loaded with both photocleavable (PC) peptide mass tags for identification and human recombinant proteins as "bait" compounds.

Preparation of Dual Affinity Beads Coated with Both NeutrAvidin and the Anti-HSV Tag Capture Antibody Performed in the same manner as in Example 3 for the anti-HSV antibody coating of 34 micron agarose beads except in this case both the anti-HSV antibody and NeutrAvidin (Invitrogen, Carlsbad, Calif.) were conjugated to the same batch of beads. In this case, instead of 6 µg of anti-HSV antibody per µL packed agarose bead volume as done in Example 3, 4 µg of anti-HSV antibody and 2 µg of NeutrAvidin (6 µg total protein) was co-loaded per each µL of packed agarose bead volume.

Fluorescent Labeling of Dual Affinity Beads for Bead-ELISA Assay

The aforementioned dual affinity beads were directly labeled with fluorescence in order to enable normalization of total bead number per sample in downstream bead-ELISA assays (see later in this Example for Bead-ELISA). The beads were fluorescently labeled as follows: The aforementioned Filtration Devices (see Example 3) were used to manipulate the beads in the following procedures unless otherwise noted. Beads were washed 4× briefly with several bead bed volumes each of Conjugation Buffer (200 mM sodium bicarbonate and 200 mM NaCl). Beads were then prepared to a 25% v/v bead suspension in Conjugation Buffer. Beads were then labeled with 270 pmoles of the Alexa Fluor® 594 SSE labeling reagent (Invitrogen, Carlsbad, Calif.) per each ML of packed bead volume (~30,000 beads) for roughly 10 fmoles added labeling reagent per bead. Labeling reagent was added from a 27 mM stock in anhydrous DMSO. The labeling reaction was performed for 30 min with gentle mixing and protected from light. Beads were then washed 4× briefly in several bead bed volumes of quench buffer (100 mM glycine in TBS; see Example 3 for TBS) and then 2× briefly in several bead bed volumes of 0.1% BSA w/v in TBS. Beads were then prepared to a 10% v/v bead suspension in 0.1% BSA w/v in TBS and stored at +4° C. protected from light.

As a quality control measure, 1 µL of packed bead volume in 100 µL of 0.1% BSA w/v in TBS was transferred to the wells of a 96-well opaque black flat bottom microtiter plate. Beads were allowed to settle by gravity for 5 min and the Alexa Fluor® 594 fluorescence read in a TECAN Spetra-Fluor Plus plate reader (Tecan Group Ltd., Männedorf, Switzerland) using a 560 nm excitation filter and 612 nm emissions filter. Using several replicate samplings, fluorescence signal was compared to beads lacking the Alexa Fluor® 594 (same bead amount), yielding an average signal-to-noise ratio of 11:1.

Preparation of Photocleavable (PC) Biotin Labeled Peptide Mass Tags

Performed in the same manner as in Example 5 except that the bradykinin peptide (Sigma-Aldrich, St. Louis, Mo.) (RPPGFSPFR) was used instead of the VSV-G peptide in Example 5.

Binding of PC-Biotin Peptide Mass Tags to Dual Affinity Beads 112.5 pmoles of the aforementioned PC-Biotin labeled bradykinin peptide mass tag was added to 0.75 µL of packed dual affinity agarose bead volume (~22,500 beads) in 225 µL of Block Buffer (see Example 3 for buffer compositions). This corresponds to ~5 fmoles of PC-Biotin bradykinin peptide mass tag per bead. The PC-Biotin bradykinin peptide mass tag was allowed to bind for 30 min with mixing. Beads were then washed 4× 400 µL briefly with TBS-T (see Example 3 for buffer). As a negative control, a parallel batch of beads was processed in the same manner except that the PC-Biotin labeled bradykinin peptide mass tag was omitted.

Binding of Recombinant Protein as "Bait" to Dual Affinity Beads

Performed exactly as in Example 3 with the following exceptions: The aforementioned dual affinity beads, with and without the PC-Biotin labeled bradykinin peptide mass tag, were used for recombinant protein capture instead of the anti-HSV beads from Example 3. To create beads containing the "bait" (nascent recombinant protein), the dual affinity beads were loaded with cell-free expressed recombinant human p53 protein (see Example 3). The p53 contained the HSV epitope tag for binding to the beads. Prior to capture on the beads, in this Example, the crude cell-free expression reactions was mixed with equal volume of 5% BSA w/v in TBS-T and pre-clarified by passing the solution through the aforementioned Filtration Devices (see Example 3). Also as in Example 3, a parallel set of blank beads was prepared in the same manner except only the expression DNA was omitted from the cell-free reaction used to synthesize the recombinant protein.

After loading the protein to the beads, washing was also performed as in Example 3. These bead samples (bead suspensions) were then each split, whereby half of each sample was used for a Bead-ELISA for detection of the bead-bound p53 bait molecules and the other half used for MALDI-TOF mass spectrometry for detection of the photocleavable peptide mass tag. Both procedures are detailed below.

Bead-ELISA for Detection of the Human Recombinant p53 "Bait" on the Beads

Beads were manipulated with the aforementioned Filtration Devices unless otherwise noted. Beads were probed with 200 µL of a monoclonal anti-VSV-G horseradish peroxidase (BRP) conjugated antibody (Clone P5D4, Sigma-Aldrich, St. Louis, Mo.) to detect the bead-bound human recombinant p53 "bait" with contained this N-terminal epitope tag. For probing, the manufacturer supplied antibody (~1 mg/mL) was diluted 1/20,000 in Block Buffer (see Example 3 for buffer). Probing was performed for 30 min with gentle mixing. Beads were then washed briefly 4× 400 µL with TBS-T and 2× 400 µL with 0.1% BSA w/v in TBS. Each bead sample was then re-suspended in 100 µL of 0.1% BSA w/v in TBS and transferred to the wells of a 96-well opaque black flat bottom microtiter plate. Beads were allowed to settle by gravity for 5 min and the Alexa Fluor® 594 fluorescence read (bead normalization signal) in a TECAN SpetraFluor Plus plate reader (Tecan Group Ltd., Männedorf, Switzerland) using a 560 nm excitation filter and 612 nm emissions filter.

Next, the anti-VSV-G HRP antibody was detected to measure the bead-bound "bait", i.e. the recombinant human p53. Without further processing, to each well of the microtiter plate containing the beads, 100 µL of SuperSignal Pico Chemiluminescence ELISA substrate (Thermo-Fisher-Pierce, Rockford, Ill.) was added and mixed for 15 min on a plate shaker. Beads were again allowed to settle by gravity for 5 min and the signal read in the TECAN SpetraFluor Plus plate reader (Tecan Group Ltd., Männedorf, Switzerland) using the instrument's luminescence mode.

Mass Tag Photocleavage and MALDI-TOF Mass Spectrometry Analysis from Beads

To detect the bead-bound PC-Biotin bradykinin peptide mass tag, an aliquot of the same batch of beads that were loaded with the mass tag as well as the recombinant human p53 (see earlier in this Example) was analyzed by mass spectrometry. This aliquot of beads was further washed 3× 400 µL briefly with TBS-T, 3× 400 µL TBS and then 4× 400 µL with Mass Spectrometry Grade Water (MSG-Water) using the aforementioned Filtration Devices. The beads were suspended in a small volume of MSG-Water and photo-release of the bead-bound mass tag was achieved via illumination for 5 min with near-UV light (365 nm peak UV lamp, Blak-Ray Lamp, Model XX-15, UVP, Upland, Calif.) at a 5 cm distance. The power output under these conditions was approximately 2.6 mW/cm$^2$ at 360 nm, 1.0 mW/cm$^2$ at 310 ram and 0.16 mW/cm$^2$ at 250 nm. The supernatant was then mixed with the MALDI-TOF matrix and analyzed under standard conditions (note that single bead mass-imaging was not done here).

Figure 6A:
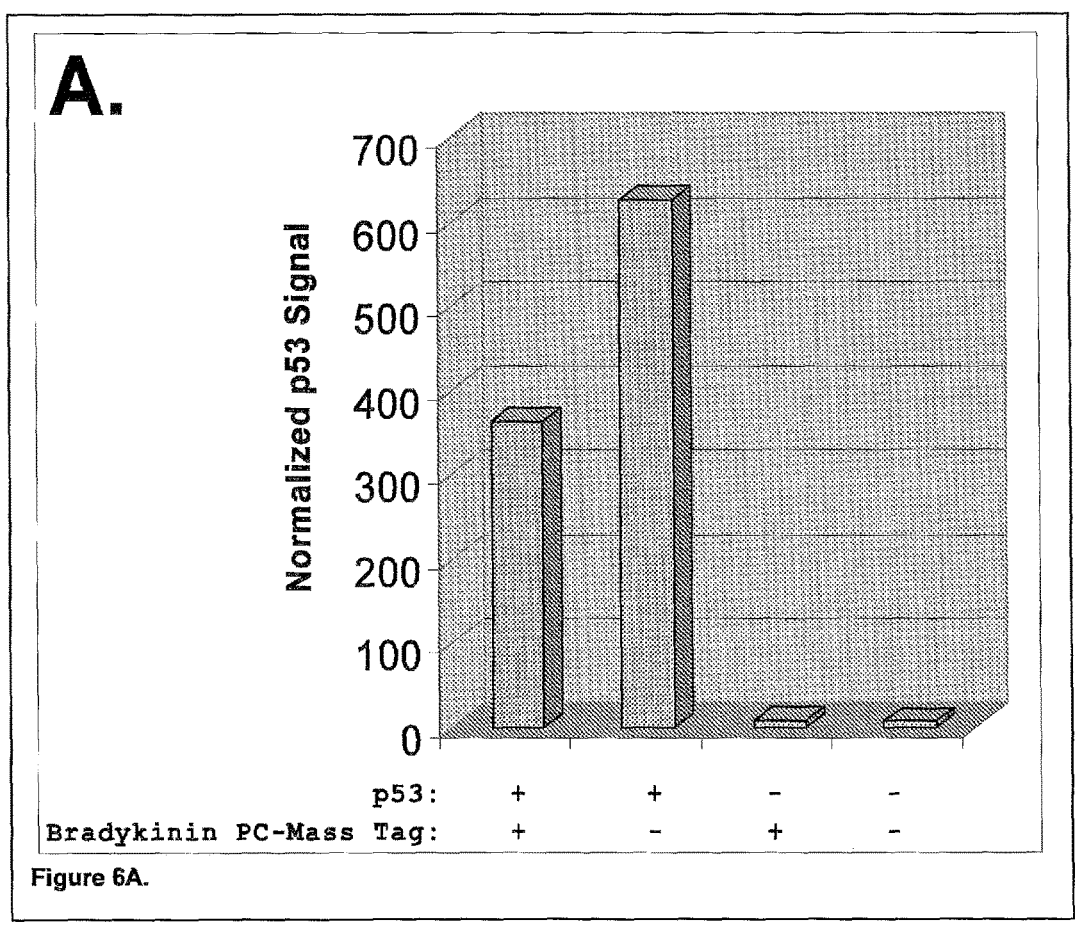

Results:

FIG. 6A shows the results of the Bead-ELISA used to detect the presence of the "bait" compound on the beads. In this case, human recombinant p53 protein was the "bait" and was detected by an HRP labeled antibody directed against its N-terminal VSV-G epitope tag. The Bead-ELISA signal readout was from an entire population of beads by way of enzymatic chemiluminescence signal generation. To normalize for the amount of beads present in each sample (due to bead pipetting variance), the beads also carried a directly-conjugated fluorescence label, which was also read from the entire bead population. The p53 signal (i.e. chemiluminescent anti-VSV HRP signal) in FIG. 6A was normalized to the fluorescence signal (relative bead amount). Results show the p53 was detected both with and without the PC-Biotin bradykinin peptide mass tag present on the beads. In this Example, the presence of the mass tag does reduce the binding capacity of the beads for p53 protein by approximately 50%. No p53 signal was observed when the p53 was absent from the beads, whether or not the mass tag was present. The signal-to-noise ratio for the p53 signal was 42:1 for the mass-tagged beads and 82:1 for the non mass-tagged beads.

Figure 6B:
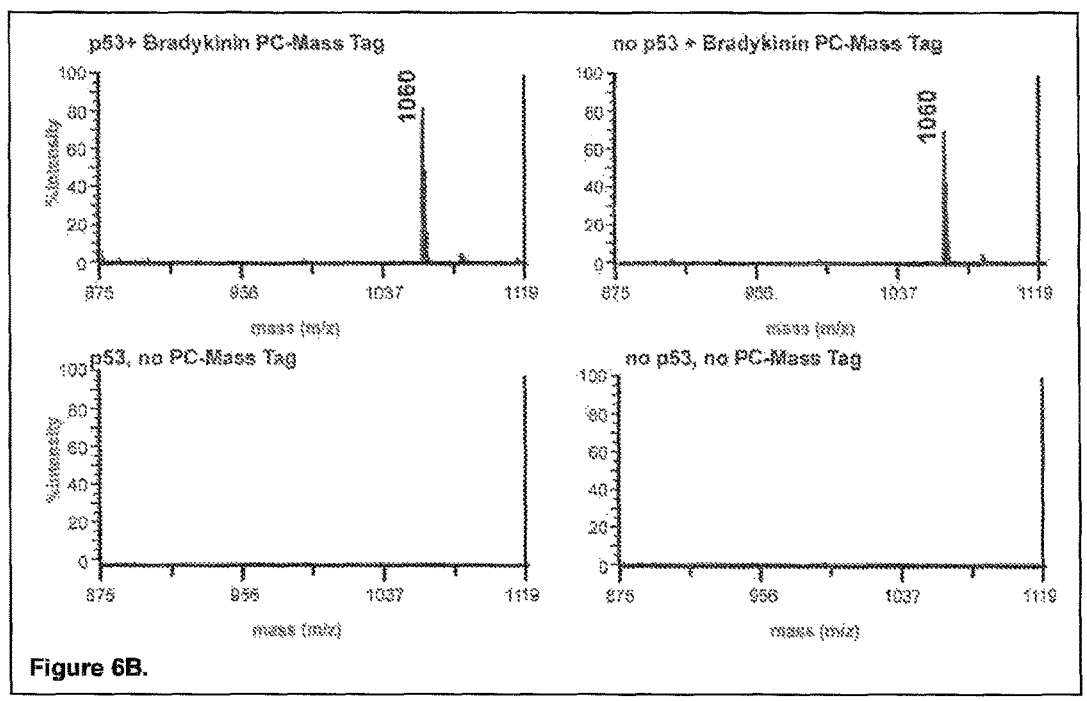

An aliquot of the same batch of beads containing the bound PC-Biotin bradykinin peptide mass tag and bound recombinant p53 "bait" protein was also analyzed by MALDI-TOF mass spectrometry, following photocleavage of the mass tag from the beads. In this Example, the photo-released mass tag from an entire population of beads was measured in bulk by conventional MALDI-TOF mass spectrometry, but other embodiments envisioned would involve mass-imaging of individually resolved beads similar to as done in Examples 5 and 7. Results in FIG. 6B show that the photocleaved bradykinin peptide mass tag was observed at its correct mass (1,060 Da), and was detected on beads with or without bound p53. No mass tag was observed on beads with our without the bound p53 in cases where the mass tag was not added to the beads.

Example 7. Photocleavable Mass-Tagged Probes for Mass Spectrometry Readout and Mass-Imaging from Individually Resolved Beads: Autoantibody Detection in Autoimmune Disease In this Example, specific probes were mass tagged with peptides and used to detect analytes bound to "bait" molecules present on beads. Detection was by using MALDI-TOF mass spectrometry mass-imaging, More specifically, the "bait" molecule on the beads in this Example is a recombinant human protein, acting as an autoantigen (i.e. self antigens targeted by serum autoantibodies in autoimmune disorders). The analyte in this Example is an autoantibody (specific human IgG) present in the serum of a patient having an autoimmune disorder (Primary Biliary Cirrhosis or PBC in this case); whereby the autoantibody is detected with a mass-tagged anti-[human IgG] secondary antibody probe.

Binding of Recombinant Protein Autoantigen to Anti-HSV Agarose Affinity Beads

Performed exactly as in Example 3. First, to create beads containing the "bait" (nascent recombinant protein autoantigen in this Example), 34 micron agarose beads coated with the anti-HSV tag antibody were loaded with cell-free expressed recombinant human KLHL12 protein (PBC autoantigen; see US provisional filling at USPTO application number 61248768). The KLHL12 contained the HSV epitope tag for binding to the beads. Also as in Example 3, a parallel set of blank beads was prepared in the same manner except only the expression DNA was omitted from the cell-free reaction used to synthesize the recombinant protein. After loading the protein to the beads, washing was also performed as in Example 3.

Preparation of the VSV-G PC-Biotin Labeled Peptide Mass Tag

Performed exactly as in Example 5.

Preparation of Fluorescent Tetrameric NeutrAvidin Protein as a Bridge from Probe to Mass Tag A 5 mg/mL stock of tetrameric NeutrAvidin biotin binding protein (Invitrogen, Carlsbad, Calif.) was prepared in PBS (50 mM sodium phosphate, pH 7.5, 100 mM NaCl). The stock was then mixed with equal volume of 200 mM sodium bicarbonate 200 mM NaCl (no pH adjustment). 500 µL of this solution was labeled with the Cy3-NHS ester reagent (GE Healthcare Life Sciences, Piscataway, N.J.) added from a 25 mM stock (stock in anhydrous DMSO) to yield a 10-fold molar excess of labeling reagent versus the NeutrAvidin. The reaction was carried out for 30 min with gentle mixing and protected from light. Un-reacted labeling reagent was removed by passing the solution through an Illustra NAP-5 G-25 sepharose desalting column according to the manufacturer's instructions (GE Healthcare Life Sciences, Piscataway, N.J.) versus a TBS buffer. Concentration of the purified and labeled NeutrAvidin was determined by measuring absorbance at 280 nm.

Treatment of Autoantigen Beads with Human Autoimmune Serum and Subsequent Probing The aforementioned beads, prepared with and without the KLHL12 autoantigen and washed as described above, were then treated with either a known KLHL12 autoantibody-positive PBC autoimmune serum or with a known autoantibody-negative normal patient serum ProMedDx, LLC (Norton, Mass.). Both sera were previously confirmed KLHL12 autoantibody-positive or negative by analysis on commercial human proteome microarrays performed according the manufacturer's instructions (Human ProtoArray® 4.0, Invitrogen, Carlsbad, Calif.). Serum treatment, probing and bead washing steps were all performed in the aforementioned Filtration Devices (see Example 3) unless otherwise noted. Sera were diluted 1/1,000 in Block Buffer (see Example 3 for buffers unless otherwise noted) and 200 µL was used to treat 1 µL packed bead volume (~30,000 beads) for each sample. Treatment was performed for 30 min with gentle mixing and the beads then washed 4× 400 µL briefly with TBS-T. Beads were then probed with 200 µL of a non-cleavable biotin labeled mouse anti-[Human IgG] secondary antibody (Jackson ImmunoResearch Laboratories, Inc., West Grove, Pa.) diluted to 10 µg/mL (~65 nM) in Block Buffer. Treatment was performed for 30 min with gentle mixing and the beads then washed 4× 400 µL briefly with TBS-T. Beads were then probed with 200 µL of the aforementioned Cy3 labeled NeutrAvidin diluted to 4 µg/mL (~65 nM) in Block Buffer. Treatment was performed for 30 min with gentle mixing and the beads then washed 4× 400 µL briefly with TBS-T. Lastly, beads were then probed with 200 µL of the aforementioned PC-Biotin labeled VSV-G peptide mass tag diluted to 65 nM in Block Buffer. Treatment was performed for 30 min with gentle mixing and the beads were then washed 3× 400 µL briefly with TBS-T, 3× 400 µL TBS and then 4× 400 µL with Mass Spectrometry Grade Water (MSG-Water).

Mass Tag Photocleavage and MALDI-TOF Mass Spectrometry Imaging of Beads

Next, this same batch of beads was then split and deposited into two separate pico-well plates (see Example 3 for plates) by brief centrifugation. One plate was used for MALDI-TOF mass spectrometry mass-imaging of individually resolved beads. Photocleavage of the PC-Biotin labeled VSV-G peptide mass tag from the beads in the plates and mass-imaging were performed as in Example 5, in order to detect bound autoantibody by virtue of the mass tag. The other plate was imaged fluorescently in a GenePix 4200 laser based microarray scanner (Molecular Devices, Sunnyvale, Calif.) to detect bound autoantibody by virtue of the fluorescently labeled NeutrAvidin.

Figure 7:
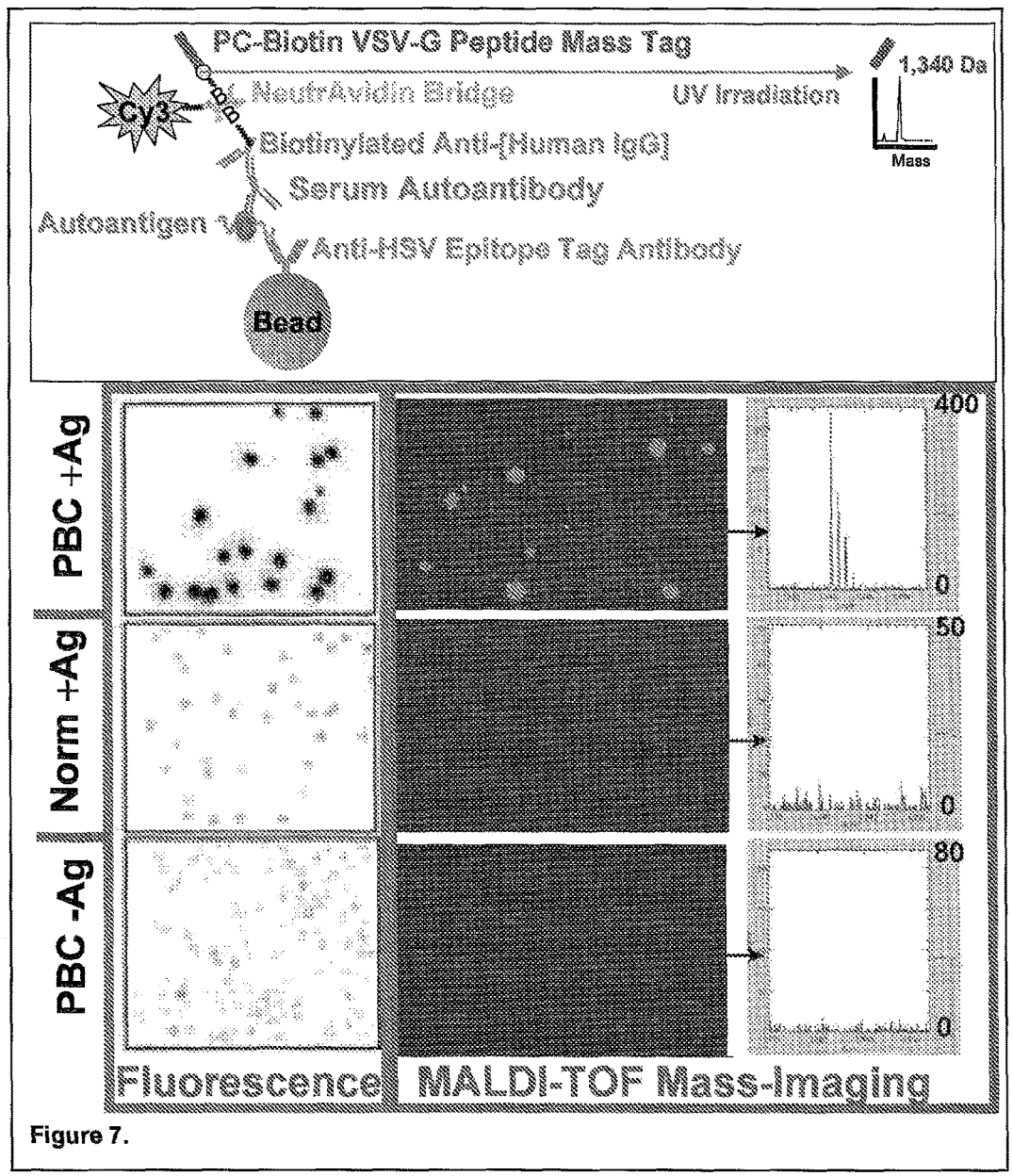

Results:

The top panel of FIG. 7 illustrates the design of the experiment. KLHL12 (autoantigen) beads and blank beads (minus antigen) were prepared and probed with the PBC autoimmune serum. A set of auto antigen beads was also probed with a normal serum as a negative control. The different bead samples were kept separate in this Example. In this experiment, bead-bound autoantibody was probed with a biotinylated (non-cleavable) anti-[human IgG] secondary antibody, followed by tetrameric NeutrAvidin as a bridge, and finally, the photocleavable (PC) biotin labeled VSV-G peptide mass tag. To enable fluorescence detection of the bead-bound autoantibody, the NeutrAvidin bridge was labeled with Cy3.

The results in FIG. 7 (bottom panel) confirm that autoantibodies against the autoantigen can be detected both by fluorescence probing as well as MALDI-TOF mass spectrometry imaging of mass-tags from individually resolved beads, with high sensitivity and specificity. In both cases, strong positive signal is observed only on beads containing the autoantigen that were probed with the PBC autoimmune serum. No significant signal is observed when autoantigen beads are probed with a normal serum or when blank beads are probed with the PBC autoimmune serum. Fluorescence signal-to-noise ratio was 30 to 60:1, which is equal or greater than the highest signal-to-noise ratio observed on the aforementioned commercial ProtoArrays® for this serum-autoantigen pair. The MALDI-TOF mass spectrometry signal-to-noise ratio for the peak due to the photocleaved PC-Biotin VSV-G peptide mass tag, in the case of positive sample, was 50:1 to 150:1, while for the two negative controls, the peak was indistinguishable from the noise (signal-to-noise ratio <2).

Figure 8:
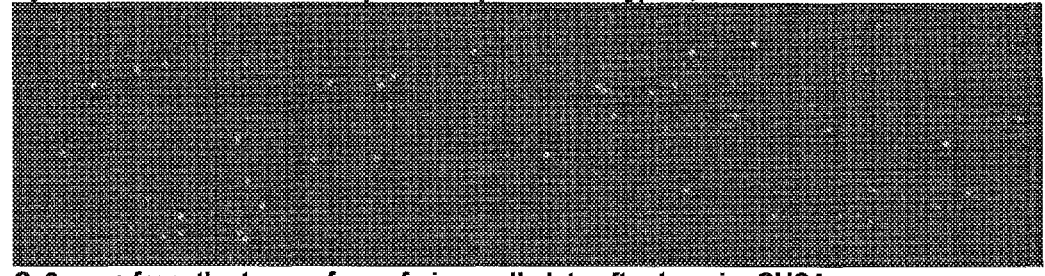
Figure 8:
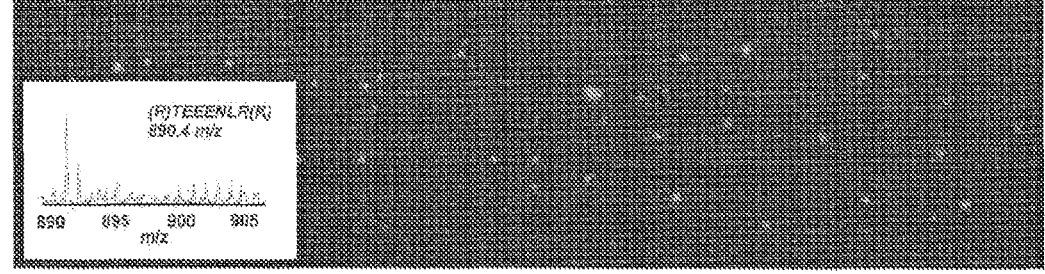

Example 8. Application of the Protease Enzyme to the Bead Library Deposited on the Pico-Well Plates: Efficient Protein Digestion without the Loss of Spatial Resolution in MALDI-TOF Mass Spectrometry Mass-Imaging In this Example, a specific protein (recombinant human p53) bound to the beads, which were deposited inside wells of a pico-well glass slide, was detected using both MALDI-TOF mass spectrometry imaging (MSI) and fluorescent scanning. The Example shows the ability to apply both the enzyme-containing solution and the MALDI matrix required for MALDI imaging in a manner that preserves the single-bead resolution of the array.
Construction of the Probe Complex
The 34 micron agarose beads were coated with the anti-HSV tag antibody. Cell-free produced recombinant human p53 protein containing an N-terminal VSV tag and a C-terminal HSV tag was purified on beads as described in Example 3. Subsequently, the protein was probed with a biotinylated anti-VSV antibody followed by incubation with a Cy3-labeled tetrameric NeutrAvidin and extensive wash to remove unbound fluorescent label.
Trypsin Digest of the Protein
The 34 micron beads containing the p53 probe complex were deposited inside wells of the pico-well glass slide. The bead density was approximately 1 bead per 20 wells. A dilute (25 μg/mL) aqueous solution of mass-spectrometry grade trypsin was applied to the surface of the slide in the form of a fine mist using a Pari (Midlothian, Va.) LC® Sprint reusable nebulizer. Following trypsin application, the slide was incubated for 1 hr at 37° C. to allow the digestion.
Application of the MALDI Matrix
For the purpose of MALDI imaging, the slides were coated with a thin layer of α-hydroxy cinnamic acid (CHCA) MALDI matrix. A 16 mg/mL solution of MS-grade CHCA in 60% of pure acetonitrile and 40% of 0.1% trifluoroacetic acid (v/v) was delivered to the surface of the slide in the form of a fine mist using a Pari (Midlothian, Va.) LC® Sprint reusable nebulizer.
Fluorescence Scanning of the Bead Library Following the Trypsin Digestion and MALDI Matrix Application
The slides were scanned using a GenePix 4200 laser based microarray scanner (Molecular Devices, Sunnyvale, Calif.) at the 532 nm wavelength corresponding to the fluorescent signal of Cy3 (FIG. 8). First, the slides were scanned in the manufacturer's suggested orientation, with signal detection from the bottom of the microwells through the fiberoptic channels. Afterward, the slides were turned upside down and the same scan was performed with signal detection from the top of the slide. In the former configuration, the image reflects the analyte, which remains inside individual microwells since the scan is performed through individual channels. In the latter configuration, the image reflects analyte located on the surface or near the surface of the slide, which was achieved by selecting the appropriate focus distance. Both images are very similar and show that the analyte, when measured by fluorescence, remains concentrated in the specific areas on the slide corresponding to the locations of microwells. Note that the Cy3 fluorescent label no longer remains bound to the protein-bead complex after the trypsin digestion.
Mass-Spectrometry Readout of the Protein Digest
MALDI MSI scanning of the surface of the same fluorescently imaged pico-well slide showed a series of peaks in the 600-3,200 Da mass range that can be assigned to proteolytic fragments of p53 produced by digestion of intact protein using trypsin. For example, the 890.4 Da peak (FIG. 8, inset) corresponds to the fragment TEEENLR (amino acids 308-314 in the recombinant protein sequence). The data shows that the protein bound to the beads, which are deposited into the microwells, is efficiently digested and can be analyzed by MALDI mass spectrometry.

The above results demonstrate that digestion of protein on individual beads followed by application of MALDI matrix does not decrease the resolution of the bead array and individual beads can still be resolved even at 10 micron resolution of the fluorescence scanner. More generally, it is expected that application of other enzymes or compounds dissolved in either aqueous or organic solution to the bead array can be performed in a manner that preserves the resolution of the bead array.

Example 9. Measurement of Changes in the Protein Concentration Using a Combination of Protein Isotope Labeling, Proteolytic Digestion and MALDI-TOF Mass Spectrometry Mass-Imaging Analysis of Bead Microarrays This Example shows the ability to measure changes in the concentration of a specific protein (recombinant p53) obtained from two different sources using MALDI bead microarrays. This is useful, for example, when changes in the protein expression between two different cell types need to be measured for multiple proteins. The approach involves: (1) expressing proteins separately in the non-labeled and isotope-labeled medium that result in incorporation of the isotope label into the synthesized proteins; (2) combining the two samples and purifying the aforementioned proteins on affinity beads such as antibody beads; (3) arranging beads into the microarray; (4) performing on-bead proteolytic digestion and (5) measuring ratio of non-labeled versus isotope-labeled proteolytic fragments, which is indicative of the ratio of proteins in the starting mixture.
Protein Isotope Labeling
Recombinant human p53 was expressed in a cell-free translation reaction supplemented with non-labeled (natural abundance) amino acid mix. Separately, p53 was expressed in a reaction supplemented with $^{13}C_6$-Leu amino acid mix. Incorporation of an isotope labeled Leucine into the protein chain results in a mass shift of +6 Da per each Leucine residue.

Affinity Purification

After the cell-free translation, the protein mixtures were separately purified on anti-HSV antibody-coated 34 micron agarose beads. In a separate experiment, the protein mixtures were mixed in a 5:1 ratio (non-labeled vs labeled) before purification and subsequently purified on anti-HSV antibody-coated 34 micron agarose beads.

Trypsin Digestion

The bead mixtures were deposited on the MALDI plate and subject to trypsin digestion. In a separate experiment, the beads were deposited into the pico-well glass slides and treated with trypsin.

MALDI-TOF Mass Spectra

The trypsin digest spectra acquired from beads, each carrying a homogenous population of p53 protein (either labeled or non-labeled), reveal a series of peaks shifted by either +6 or +12 Da. For example (FIG. 9A), the 1006 Da peak in the non-labeled protein is shifted to 1018 Da in the labeled protein spectra. The mass-shifted peaks can be assigned to proteolytic segments of p53 containing one (+6 Da) or two (+12 Da) Leu residues.

Protein Quantification Using Isotope Labeling and MALDI MS Detection

Next, p53 was expressed in non-labeled and isotope labeled media and the translation reactions were mixed in a 5:1 ratio prior to binding to the beads to mimic different levels of protein expression. Trypsin digestion and MS analysis were performed as described previously. The mass spectra (FIG. 9B) show that the ratio of 1006 to 1018 Da peaks is very close to 5:1, matching the differences in protein amount.

Detection of Isotope-Shifted Peaks on Bead Microarrays

In this example, the mixture of beads carrying either pure non-labeled or pure isotope-labeled p53 proteins was deposited on the pico-well slides, so that each well contains no more than one bead. The on-bead trypsin digestion and MALDI matrix deposition were performed as described in Example 8. The slide was scanned using MALDI MSI and signals at 1,006 and 1,018 Da corresponding to the isotope-shifted p53 proteolytic fragments were detected. As seen in FIG. 9C, two distinct non-overlapping populations of beads were detected on the slide that correspond to the two populations of p53 beads.

Example 10. Photocleavable DNA Tags and Bead Decoding by Massively Parallel RT-PCR Chips One embodiment of this invention involves use of PC-DNA tags to code and decode beads. As an example, solid-phase (bead) PCR with universal photocleavably attached primers, was used to separately amplify various human open reading frame (ORF) plasmid inserts on a 34 micron agarose beads; thus creating photocleavably tethered DNA amplicons (pure species on each bead). Several different DNA-bead species were then pooled at various ratios and then photocleaved.

The photo-released DNA can be analyzed on a suitable instrument which can detect the DNA tags, such as a standard DNA hybridization chip (e.g. DNA microarray), a massively parallel DNA sequencer or an RT-PCR device. In the case of DNA hybridization chips, many chips are available such as from AffyMetrix (Santa Clara, Calif.) which have probes for thousands of genes that can be used to detect the release of specific DNA sequences photo-released from the beads. In this Example, a commercial prototype massively parallel RT-PCR chip from WaferGen BioSystems Inc. (Fremont, Calif.) was used that can simultaneously analyze large numbers of such PC-DNA tags. In this Example, WaferGen's 5,000-member prototype RT-PCR chip was used containing probes to all members of the test bead library evaluated. As shown in FIG. 10, gene ORFs were positively identified when photocleaved from as little as a single bead, with Cycle Threshold (Ct) values approximately following the bead numbers.

Example 11. Physical Pre-Selection of Beads for Decoding Using a Fluorescence Activated Cell-Sorting (FACS) Instrument We evaluated in the feasibility of pre-isolating 34 micron agarose beads using fluorescence activated cell-sorting (FACS). Pre-isolation of only the positive beads of interest (e.g. by virtue of bound fluorescent probes) greatly reduces the number of beads required to be decoded by MALDI-TOF mass spectrometry mass-imaging for example. Importantly, FACS is high throughput (can process millions of beads in a few minutes) and has the ability for greater reproducibility and specificity than magnetic particle based affinity isolation methods, since beads can be analyzed by multiple parameters on a bead-by-bead basis. In this Example, blank protein beads and beads containing a recombinant protein autoantigen for the autoimmune disease primary biliary cirrhosis (PBC) were separately prepared and probed with an appropriate autoantibody-positive human serum as detailed in Example 7. Bound autoantibody was detected with a fluorescently labeled secondary anti-[human IgG] antibody (fluorescein). Beads were then analyzed using a fluorescence activated cell sorting (FACS) instrument using a commercial service (BD FACS Vantage Cell Sorter; Cytometry Research LLC, San Diego, Calif.). As seen in FIG. 11, using the same cutoffs, 93% of the control beads (blank) were scored negative while 96% of the autoantigen beads were scored positive. Specificity of the fluorescence signal is verified by analysis using a second fluorescence channel (Cy3), showing no significant signal.

Example 12. Photocleavable Mass Tags for Bead Identification and Probe Readout in an Immune Response Profiling Scenario: MALDI-TOF Mass-Imaging of Individually Resolved Beads in an Array One embodiment of mass spectrometry mass-imaging of beads or particles is to load onto the beads both a mass tag for bead identification ("bead identification tag") and "bait" molecules or compounds for use in multiplex bioassays. Furthermore, a probe ("prey") used to treat (query) the beads can carry a different photocleavable mass tag for assay readout ("probe tag"). In this scenario, mass-imaging of the beads results in two mass tag signals from those beads on which the bait has bound its cognate probe, one mass tag for the bead identification tag and one for the probe tag. In this Example, human recombinant proteins act as the "bait" compounds. An immune response profiling application is shown here as an example, whereby one of the bait proteins is a known autoantigen and the other bait protein is a negative control (non-autoantigen). The beads are then treated with a human serum from an autoimmune patient known to have autoantibodies against said autoantigen. To detect bound autoantibody, the beads are then probed with an anti-[human IgG] secondary antibody which is ultimately detected with a unique photocleavable mass tag reporter (probe tag).

Preparation of Dual Affinity Beads Coated with Both NeutrAvidin and the Anti-HSV Tag Capture Antibody Performed as in Example 6 (34 micron agarose beads).

Preparation of Photocleavable (PC) Biotin Labeled Peptide Mass Tags

Performed as in Example 5 except that the following peptides were labeled: Bradykinin (RPPGFSPFR) (Sigma-Aldrich, St. Louis, Mo.) was labeled for use as the probe tag and two custom peptides, obtained commercially from Sigma-Genosys (The Woodlands, Tex.), were labeled for use as the bead identification tags (Tag-3.1=MIGGAGGRIR and Tag-3.7=MIGGTGGRIR).

Binding of PC-Biotin Peptide Mass Tags to Dual Affinity Beads

Performed as in Example 6 except that 200 µL of PC-Biotin peptide mass tag solution at a concentration of 0.75 pmoles/µL (150 pmoles) was added to a 1 µL bead pellet volume (30,000 beads); for a final added amount of PC-Biotin peptide mass tag of 5 fmoles per bead. As in Example 6, this step is to capture the PC-Biotin peptide mass tags on the dual affinity beads by way of the NeutrAvidin coating on the beads (peptide capture efficiency not measured). In this Example, separate batches of beads were prepared that were loaded with either the Tag-3.1 or the Tag-3.7 mass tag, creating two pure populations of mass tag encoded beads. After capture of the PC-Biotin peptide mass tags on beads and washing as in Example 6, the beads were quenched with 1 mM d-biotin in TBS-T (200 µL per 1 µL bead pellet) (see Example 3 for buffer compositions). Quenching was performed for 30 min with mixing in the upper chamber of the Filtration Devices (see Example 3 for Filtration Devices and their usage). The 1 µL bead pellets were then washed (in the Filtration Device) 4× 400 µL briefly with TBS-T.

Binding of Recombinant Protein as "Bait" to Dual Affinity Beads

Performed essentially as in Example 6 with the following exceptions: Beads with the Tag-3.1 identification tag were loaded with cell-free expressed recombinant human Smith protein, a well known autoantigen biomarker for systemic lupus erythematosus (SLE) [Mahler, Stinton and Fritzler (2005) Clin Diagn Lab Immunol 12: 107-13]. Here, the B isoform of Smith was used (SmB). Beads with the Tag-3.7 identification tag were loaded with cell-free expressed recombinant human GST A2 protein as a negative control (not a known autoantigen for SLE) (see Example 3 for cell-free protein expression). Treatment of the beads with the cell-free expression reactions for recombinant protein capture was performed as in Example 6, except that immediately following completion of the expression reactions (prior to mixing with beads), protease inhibitor was additionally added to the expression reactions to reduce the possibility of subsequent proteolytic degradation of the peptide mass tags on the beads ("Complete Mini Protease Inhibitor Cocktail Tablets" form Roche Applied Science, Indianapolis, Ind., Catalog Number 11836153001; Stock Solution=1 mini-tablet in 1 mL of purified water; add 1/10 volume of Stock Solution to completed cell-free protein expression reactions). As in Example 6, the mechanism of capture of the cell-free expressed recombinant proteins on the dual affinity beads is by way of the anti-HSV antibody coating on the beads and the common C-terminal HSV epitope tag present in all expressed proteins.

Finally, after loading the recombinant proteins onto the beads, washing was 4× 400 µL briefly with TBS-T and 2× 400 µL briefly with Block Buffer (see Example 3 for buffer compositions).

Immune Response Profiling Using the PC-Mass-Tagged and Recombinant Protein Loaded Beads The two bead populations (separate), were each sequentially treated as follows: All bead manipulations and washes were performed in the Filtration Devices unless otherwise noted (see Example 3 for the Filtration Devices and their usage). See Example 3 for buffer compositions. Beads (1 µL pellet volumes) were first probed with a known SmB positive human serum from an SLE patient. Serum was diluted 1/1,000 in 5% BSA (w/v) in TBS-T and 100 µL used to treat the beads for 30 min with mixing. Beads were then washed 5× 400 µL briefly with TBS-T. Beads were then probed with 200 µL of a non-cleavable biotin labeled mouse anti-[Human IgG] secondary antibody (Jackson ImnmunoResearch Laboratories, Inc., West Grove, Pa.) diluted to 10 µg/mL (~65 nM) in 5% BSA/TBS-T supplemented with 1 mM d-biotin. Treatment was performed for 30 min with gentle mixing and the beads then washed 4× 400 µL briefly and 2× 400 µL for 5 min each with TBS-T. Beads were further washed 4× 400 µL briefly with 5% BSA/TBS-T. Beads were then probed with 200 µL of Cy3 labeled NeutrAvidin (see Example 7) diluted to 4 µg/mL (~65 nM) in 5% BSA/TBS-T. Treatment was performed for 30 min with gentle mixing and the beads then washed 4× 400 µL briefly with TBS-T. Lastly, beads were then probed with 200 µL of the aforementioned PC-Biotin labeled Bradykinin peptide mass tag (probe tag) diluted to 65 nM in 5% BSA/TBS-T. Treatment was performed for 30 min with gentle mixing and the beads were then washed 4× 400 µL briefly with TBS-T, 4× 400 µL TBS and then 4× 400 µL with Mass Spectrometry Grade Water (MSG-Water).

Mass Tag Photocleavage and MALDI-TOF Mass Spectrometry Imaging of Beads

Performed in the pico-well plates as in Examples 5 & 7. Note that the two populations of bead species (SmB and GST) were pooled prior to deposition into the pico-well plates. In this Example, no florescence imaging was used.

Confirmation of Mass-Imaging Results Using ELISA

Results of autoantibody detection on beads with the mass-imaging approach were confirmed by testing the same SLE serum against the same cell-free expressed recombinant proteins using a 96-well microtiter plate based ELISA. For this, AmberGen's T$^2$-ELISA™ was used (see Description of Invention for overview of T$^2$-ELISA™). The procedures were as follows:

Cell-Free Protein Expression for ELISA

See Example 3 for cell-free protein expression. Protein expression reactions contained the cognate plasmid DNA while blank expression reactions lacked only the plasmid DNA. Expression reactions were stopped by diluting 1/20 in TDB [1% BSA (w/v) and 0.1% (v/v) Triton X-100 in TBS-T (50 mM Tris, pH 7.5, 200 mM NaCl, 0.05% (v/v) Tween-20)].

Enzyme-Linked Immunosorbent Assay (ELISA) for Autoantibody Detection

Nunc Brand 96-well Polysorp™ Microwell™ white opaque, flat bottom, untreated polystyrene microtiter plates (Nunc Brand from Thermo-Fisher Scientific, Rochester, N.Y.) were used for a sandwich type Enzyme-Linked Immunosorbent Assay (ELISA). Plates were coated with 0.5 µg/mL of a mouse monoclonal anti-HSV® tag capture antibody (EMD Biosciences, Inc., San Diego, Calif.) in sodium carbonate/bicarbonate pH 9.3 for 30 min with shaking (50 µL/well). Plates were then washed 6× in TBS-T (wells filled to maximum) on an ELx405 Select Robotic Plate Washer (BioTek, Winooski, Vt.). See Example 3 for TBS-T buffer composition. All plate washes were performed in this manner unless noted otherwise. Plates were then blocked for 30 min at 300 µL/well in 1% BSA (w/v) in TBS-T. The solution was removed from the plates and the aforementioned stopped (i.e. diluted) cell-free expression reactions (protein and blank reactions) were then added at 100 µL/well and shaken for 30 min to allow the nascent proteins to be captured by their common C-terminal HSV epitope tags. Plates were washed and the same SLE serum sample used for the bead assays earlier in this Example (diluted at 1/1,000 in 1% BSA (w/v) in TBS-T) was added at 100 µL/well and shaken for 30 min. The serum sample was run against wells of the proteins and wells of the cell-free expression blank. Additionally, one set of wells of protein and one set of wells of the cell-free expression blank were designated for VSV-G epitope tag detection (common N-terminal tag in all expressed proteins), and therefore received plain 1% BSA (w/v) in TBS-T instead of diluted serum at this stage. To avoid contamination of the robotic plate washer with human serum, plates were subsequently washed 4× by manual addition of TBS-T (wells filled to maximum) followed by vacuum aspiration and then washed 6× in the robotic plate washer as described earlier in this Example. Wells designated for detection of the VSV-G epitope tag then received an anti-VSV-G horseradish peroxidase (HRP) labeled monoclonal antibody (Clone P5D4, Roche Applied Science, Indianapolis, Ind.) diluted 1/20,000 in 1% BSA/TBS-T. Wells designated for detection of serum autoantibody received a mouse anti-[human IgG] HRP labeled monoclonal secondary antibody (minimum cross-reactivity with mouse immunoglobulin; Jackson ImmunoResearch Laboratories, Inc, West Grove, Pa.) diluted 1/20,000 in 1% BSA/TBS-T. Plates were shaken for 30 min. The solutions were then manually dumped from the plates by inversion followed by vigorous patting of the plates inverted on a dry paper towel to remove residual fluid. Plates were then washed in the robotic plate washer as described earlier in this Example. Chemiluminescence signal was generated by the addition of 50 µL/well of SuperSignal ELISA Pico Chemiluminesence Substrate (Pierce Brand from Thermo Fisher Scientific, Rockford, Ill.). Plates were developed by shaking for 15 min and then read on a LumiCount luminescence plate reader (1s exposure, PMT of 650V, gain 1) (Packard/PerkinElmer Life and Analytical Sciences, Inc., Boston, Mass.).

Figure 12A:
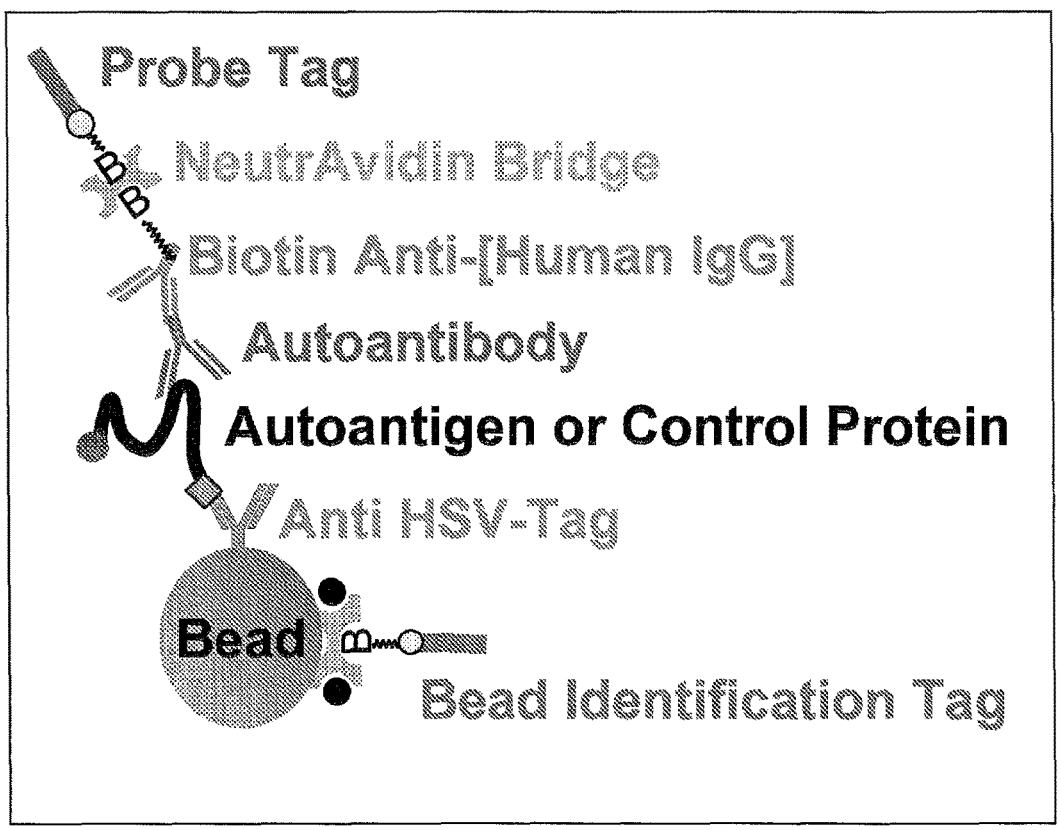
Figure 12B:
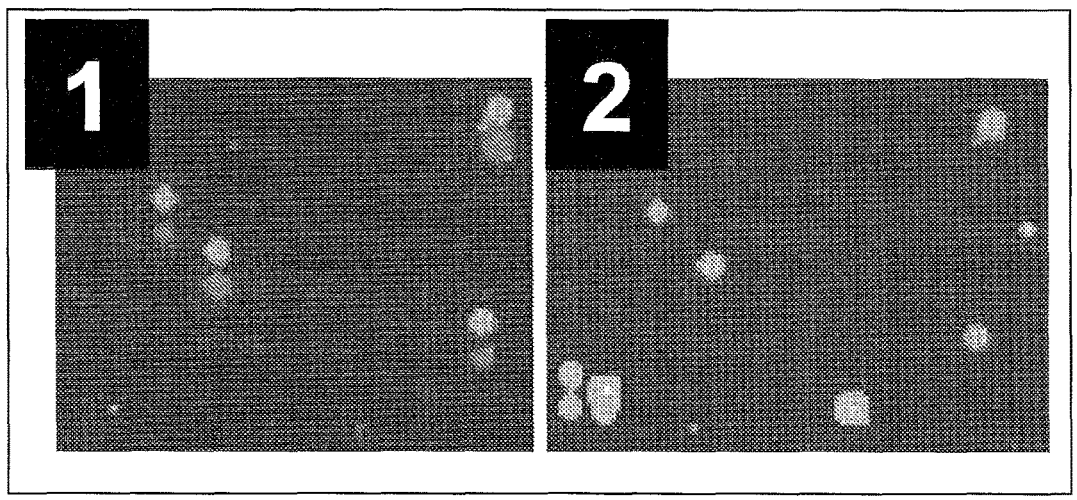
Figure 12C:
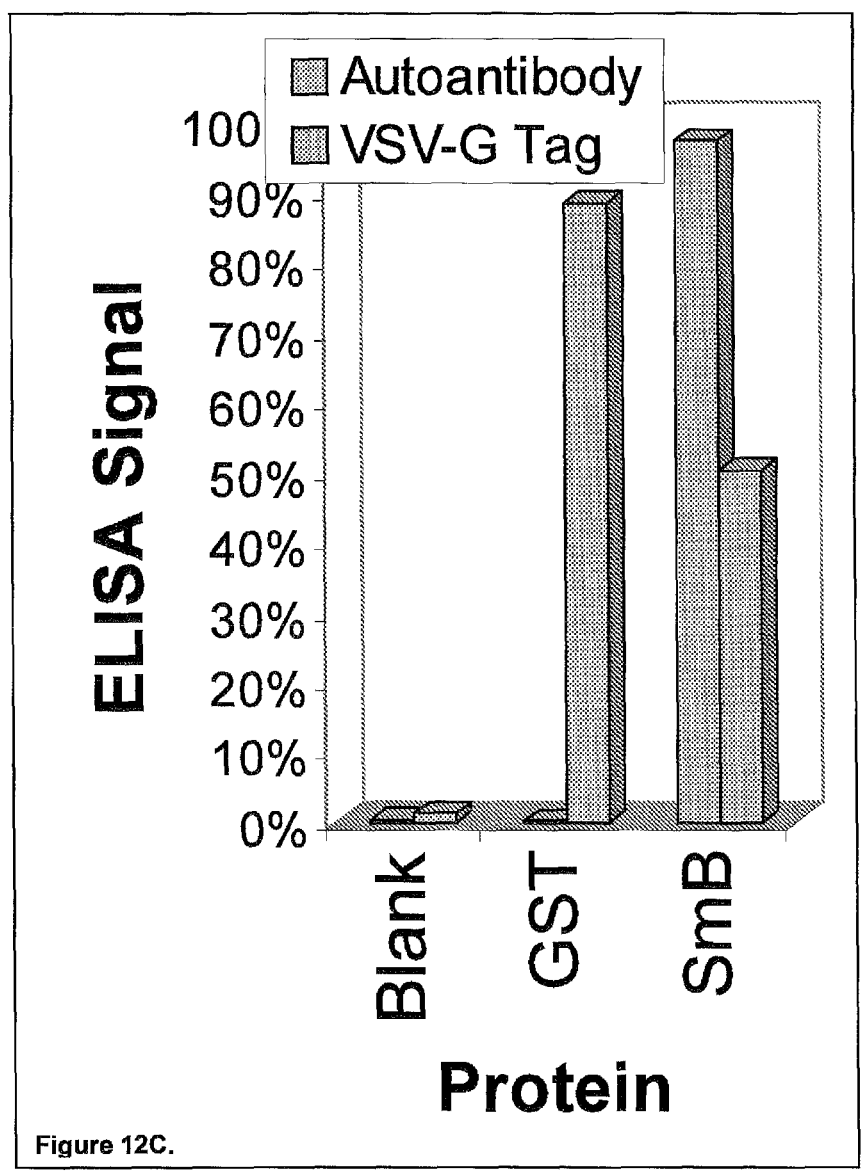

Results:

FIGS. 12A-C show the design and results of autoantibody profiling on the beads using a fully PC-Mass-Tag based configuration. FIG. 12A illustrates the basic experimental design. For this experiment, beads were coated with both NeutrAvidin and the anti-HSV antibody. PC-Biotin labeled peptide Mass-Tags ("Bead Identification Tags") were used to encode the two bead populations and the unoccupied biotin binding sites on the NeutrAvidin were permanently quenched with soluble d-biotin (black circles in FIG. 12A). Beads were then loaded with cell-free expressed proteins (rabbit reticulocyte expression system). Either human GST A2 (negative control) or SmB (SLE autoantigen) were loaded to the beads by direct in situ capture through their common C-terminal HSV tag. Beads were then sequentially probed with a known SmB positive SLE serum, biotinylated anti-[Human IgG] secondary antibody, tetrameric NeutrAvidin as a bridge and a single species of PC-Biotin labeled Mass-Tag ("Probe Tag"). Note that although not done in this Example, in another embodiment, the NeutrAvidin bridge can be fluorescently labeled for both fluorescence and mass-tag readout of bound autoantibody.

MALDI-TOF mass-imaging of the pooled beads following their deposition into the pico-well plates was performed. Results in FIG. 12B (image 1) show excellent concordance between the Probe Tag (red) and only the SmB beads as revealed by their Bead Identification Tag (green; offset in image 1 of FIG. 12B). The negative control GST beads, revealed by their specific Bead Identification Tag (white/gray; overlaid in image 2 of FIG. 12B), show no signal from the Probe-Tag as expected. In image 2 of FIG. 12B, the SmB beads show as yellow spots in the direct image overlay (composite of red and green mass-tag signals from their Probe Tag and Bead Identification Tag respectively).

To validate these results, we used a conventional 96-well microtiter plate ELISA assay ($T^2$-ELISA™) formatted in analogy to the bead assay. Cell-free expressed proteins were immobilized on the ELISA well surface by anti-HSV antibody-mediated capture. Following serum treatment, wells were probed with an enzyme-labeled (HRP) anti-[Human IgG] secondary antibody to detect bound autoantibody. As an additional control, the amount of captured protein was detected in separate wells with a reporter-labeled antibody to the common N-terminal VSV-G epitope tag in all expressed proteins. Results are shown in FIG. 12C. VSV-G epitope tag signal reveals that both GST and SmB were expressed and captured at similar levels, while the expression blank shows no significant signal (expression reaction without DNA). However, the autoantibody readout shows the SLE serum (same as in bead assay) reacts only with SmB as expected.

Example 13. MALDI-TOF Mass-Imaging of 10 Unique Photocleavable Mass-Tag Encoded Bead Species in an Array: Mass-Imaging for Identification in Conjunction with Antibody Detection of a Bead-Bound Bait Protein In this Example, 10 distinct species of beads, each carrying unique photocleavable peptide mass tags, and 1 additionally containing a recombinant protein, were prepared and arrayed in the pico-well plates. The array of all 10 bead species, randomly distributed, was then mass-imaged using MALDI-TOF.

All beads in this Example carried both a unique peptide mass tag for identification as well as a common capture antibody. The antibody serves to bind recombinant proteins that contain a common epitope tag. The captured recombinant proteins act as "bait" for specific probes ("prey"), such as a fluorescently labeled detector antibody. In this Example, 1 of the 10 bead species carried cell-free expressed recombinant p53 protein (captured by antibody) in addition to the peptide mass tag. The p53 beads were additionally detected using a fluorescent antibody directed against an epitope tag in the p53 protein.

Preparation of Dual Affinity Beads Coated with Both NeutrAvidin and the Anti-HSV Tag Capture Antibody Performed as in Example 6 (34 micron agarose beads).

Preparation of Photocleavable (PC) Biotin Labeled Peptide Mass Tags

Performed as in Example 5 except that the following custom peptides obtained commercially from Sigma-Genosys (The Woodlands, Tex.) were used for labeling (peptide sequence in brackets):

| | | |
|---|---|---|
| 1. | Tag-1.1 | [QRPDVTR] |
| 2. | Tag-2.3 | [DIEHNR] |
| 3. | Tag-2.8 | [DIERNR] |

-continued

| 4. | Tag-3.1 [MIGGAGGRIR] |
| 5. | Tag-3.2 [MIGGEGGRIR] |
| 6. | Tag-3.4 [MIGGIGGRIR] |
| 7. | Tag-3.5 [MIGGSGGRIR] |
| 8. | Tag-3.6 [MIGGPGGRIR] |
| 9. | Tag-3.7 [MIGGTGGRIR] |
| 10. | Tag-3.8 [MIGGRGGRIR] |

Binding of PC-Biotin Peptide Mass Tags to Dual Affinity Beads

Performed as in Example 6 except that 200 µL of PC-Biotin peptide mass tag solution at a concentration of 0.75 pmoles/µL (150 pmoles) was added to a 1 µL bead pellet volume (30,000 beads); for a final added amount of PC-Biotin peptide mass tag of 5 fmoles per bead. As in Example 6, this step is to capture the PC-Biotin peptide mass tags on the dual affinity beads by way of the NeutrAvidin coating on the beads (peptide capture efficiency not measured). In this Example, 10 separate batches of beads were prepared, each batch uniquely loaded with 1 of the 10 aforementioned peptides, creating 10 pure populations of unique mass tag encoded beads. After capture of the PC-Biotin peptide mass tags on beads and washing as in Example 6, the beads were quenched with 1 mM d-biotin in TBS-T (200 µL per 1 µL bead pellet) (see Example 3 for buffer compositions). Quenching was performed for 30 min with mixing in the upper chamber of the Filtration Devices (see Example 3 for Filtration Devices and their usage). The 1 µL bead pellets were then washed (in the Filtration Device) 4× 400 µL briefly with TBS-T.

Binding of Recombinant Protein as "Bait" to Dual Affinity Beads

Although in some embodiments all mass tagged bead species can additionally carry a "bait" molecule such as a protein, in this Example, with the exception of the Tag-3.7 beads, the other 9 mass tagged bead species were not loaded with cell-flee expressed recombinant protein and thus not subjected to this portion of the procedure:

Beads with the Tag-3.7 identification tag were loaded with cell-free expressed recombinant human p53 protein essentially as in Example 6 with the following exceptions: Treatment of the beads with the cell-free expression reaction for recombinant p53 protein capture was performed as in Example 6, except that immediately following completion of the expression reaction (prior to mixing with beads), protease inhibitor was additionally added to the expression reaction to reduce the possibility of subsequent proteolytic degradation of the peptide mass tags on the beads ("Complete Mini Protease Inhibitor Cocktail Tablets" form Roche Applied Science, Indianapolis, Ind., Catalog Number 11836153001; Stock Solution=1 mini-tablet in 1 mL of purified water; add 1/10 volume of Stock Solution to completed cell-free protein expression reactions). As in Example 6, the mechanism of capture of the cell-free expressed recombinant p53 protein on the dual affinity beads is by way of the anti-HSV antibody coating on the beads and the C-terminal HSV epitope tag present in the recombinant p53. Finally, after loading the recombinant p53 protein onto the Tag-3.7 encoded beads, washing was 4× 400 µL briefly with TBS-T and 2× 400 µL briefly with Block Buffer (see Example 3 for buffer compositions).

As a negative control, a separate "blank" bead sample was prepared, corresponding to beads treated with a cell-free expression reaction that was performed lacking only the p53 DNA.

Pooling Beads and Fluorescence Detection of p53 Beads

All 10 bead species were then pooled in equal numbers. As a control, an aliquot of the pure p53 beads was also set aside. This created 3 bead populations ("samples"): The 10-species pool, the p53 beads and the blank beads (see above). Each of the 3 bead samples was then probed with a fluorescently labeled anti-VSV-Cy3 antibody to specifically detect the p53 beads, by way of the VSV epitope tag present in the recombinant p53. After fluorescence probing, an aliquot of the 10-species pooled sample was set aside for MALDI-TOF mass-imaging (next section). All remaining portions of the 3 bead samples were embedded in a polyacrylamide film on a microscope slide and fluorescently imaged in a microarray scanner. The fluorescence antibody probing, embedding and fluorescence imaging was performed as in Example 3 in the section headed "Verification of Bound Recombinant Proteins".

Mass Tag Photocleavage and MALDI-TOF Mass Spectrometry Imaging of Beads

Figure 13A:
Figure 13B:
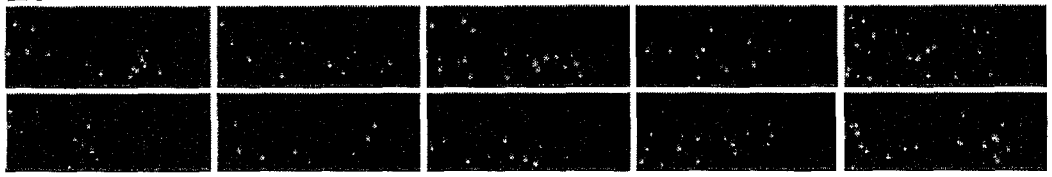

Performed in the pico-well plates as in Examples 5 & 7.
Results:

This Example successfully shows the ability to mass-image 10 distinct peptide-bead species (mass-tagged beads), using 34 micron beads arrayed in the pico-well plates (peptides affinity captured on beads with a photocleavable linker). FIG. 13A shows an overlaid mass-image, whereby all signals from all 10 peptide mass tag species are colored red (pixel intensity proportional to mass spectral intensity). Regions of overlap of any two or more peptide mass tag species are colored yellow. As seen, individual 34 micron beads can be imaged by virtue of the mass of the unique peptides originating from them. Negligible overlap between different peptide species in the mass image is observed (<5 beads in field of view), thus confirming the spatial resolution of single beads in the mass image. The panels in FIG. 13B show separate mass images for each the 10 peptide-bead species for the same region (grayscale only). As seen, beads corresponding to all 10 peptide mass tag species are equally represented in the mass-image.

Figure 13C:
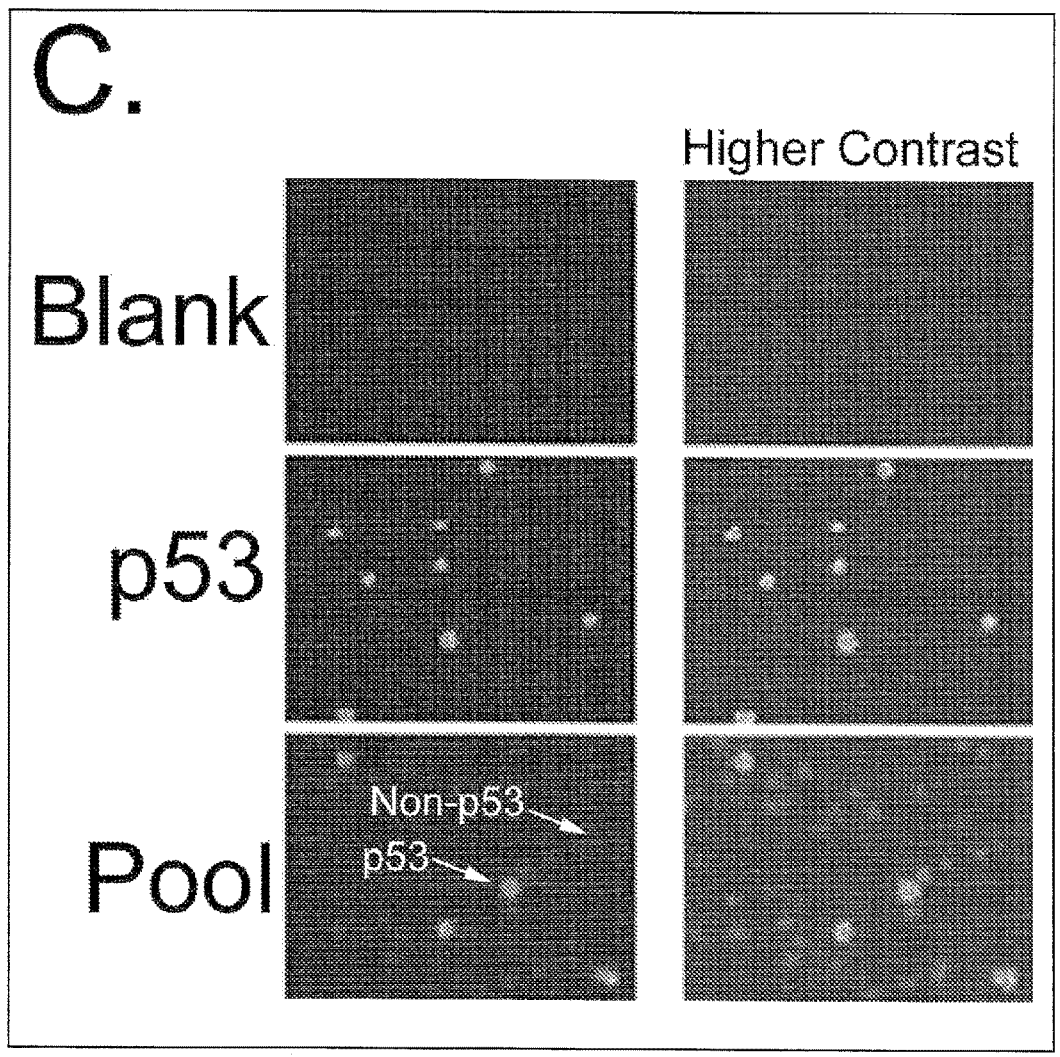

To confirm that peptide mass tag imaging of beads is compatible with the presence of "bait" molecules on the same beads, such as a recombinant protein, an aliquot of the same beads was subjected to fluorescence imaging on a microscope slide. Note: These beads had also been probed with a florescent antibody directed specifically against an epitope tag in the p53 protein. Results are shown in FIG. 13C. As can be seen, control beads corresponding to the pure population of p53 beads before pooling as well as the negative control (blank) beads, show that a p53 is specifically detected by fluorescence using a specific antibody probe ("prey"). In the "Higher Contrast" image, blank beads are slightly visible via their non-specific background fluorescence. Signal-to-noise for p53 detection was ~25:1. In the image of the pooled beads, p53 beads are distinguished by their strong fluorescence, while the other mass-tagged non-p53 beads are slightly visible again via their non-specific background fluorescence.

Figure 14A:
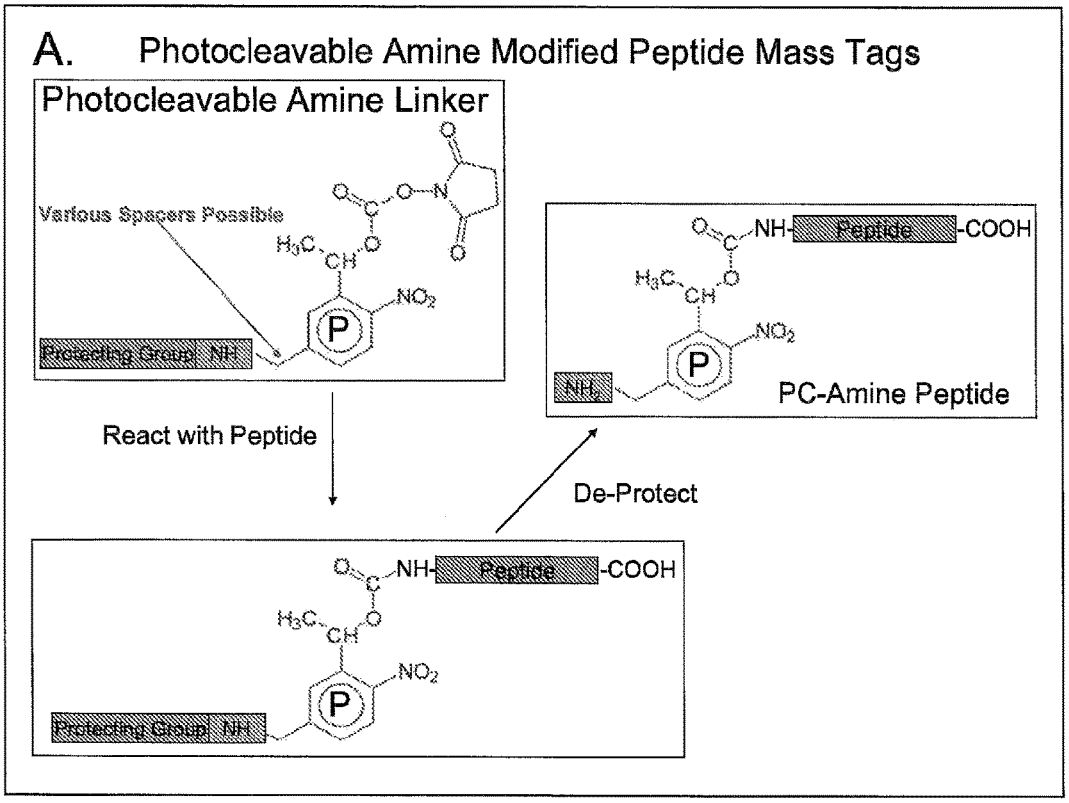

Example 14. Direct Chemical Linkage of Photocleavable Mass Tags to Bead Surfaces: Elimination of the Need for Affinity Based Linkages The previous Examples used affinity linkages to attach peptide mass tags to beads for MALDI-TOF mass-imaging and decoding, e.g. bead-bound antibodies used to capture epitope-containing peptide mass tags in Example 3, or bead-bound (strept)avidin used to capture photocleavable biotin labeled peptide mass tags in Example 13. However it is possible, and in fact desirable in some cases, to directly attach mass tags (peptides or otherwise) to beads using a direct chemical linker by way of a covalent bond, whereby the linker is photocleavable. This eliminates the need for an affinity capture agent (e.g. antibody or (strept)avidin)), which may interfere with some downstream applications. This Example will show one embodiment of this:

In this Example, the compound shown in FIG. 14A (upper left panel) will be synthesized ("Photocleavable Amine Linker"). This compound will consist of a protected amine moiety on one end, an activated amine-reactive NHS ester on the other end and a spacer arm and photocleavable nucleus in between. As shown in FIG. 14A, the NHS ester will be for attachment of the compound to an amine-bearing mass tag (e.g. peptide) and the protected amine in the compound will be for later attachment, following de-protection, of the modified mass tag to a surface, such as a bead, or to another molecule such as a probe ("prey"), for example an antibody probe. It is understood that this "Photocleavable Amine Linker" is one example compound of many possible compounds that can be used for direct covalent attachment of photocleavable mass tags to surfaces or to other molecules (e.g. probes). For instance, instead of an activated NHS ester, other activated or react-able moieties can be used, such as sulfhydryl-reactive maleimide moieties, or carboxyl or phosphate moieties which can be cross-linked to mass tags using carbodiimide chemistries. Likewise, the protected amine can be replaced by a different moiety (protected if necessary) to facilitate attachment of the modified photocleavable mass tag to a surface (e.g. bead) or to another molecule (e.g. probe). Finally, the while a hydrocarbon spacer arm is shown in the current compound, other spacers are possible, for example a 2,2'-(ethylenedioxy)-bis-(ethylamine) spacer could be used for better solubility in an aqueous environment [Pandori, Hobson, Olejnik, Krzymanska-Olejnik, Rothschild, Palmer, Phillips and Sano (2002) Chem Biol 9: 567-73].

In this Example, FIGS. 14A and B show one embodiment to be tested that will use the "Photocleavable Amine Linker" to modify a peptide mass tag. Following mass tag modification, the amine on the "Photocleavable Amine Linker" will be de-protected. The protecting group on the amine can be acid labile, such as a Boc protecting group, or base labile, for instance an Fmoc protecting group (or a protecting group cleavable by other means). In this case, a Boc protecting group will be used and trifluoroacetic acid (TFA) will be used for de-protection. Following de-protection, the modified peptide mass tag will be purified using a gel filtration column.

Figure 14B:
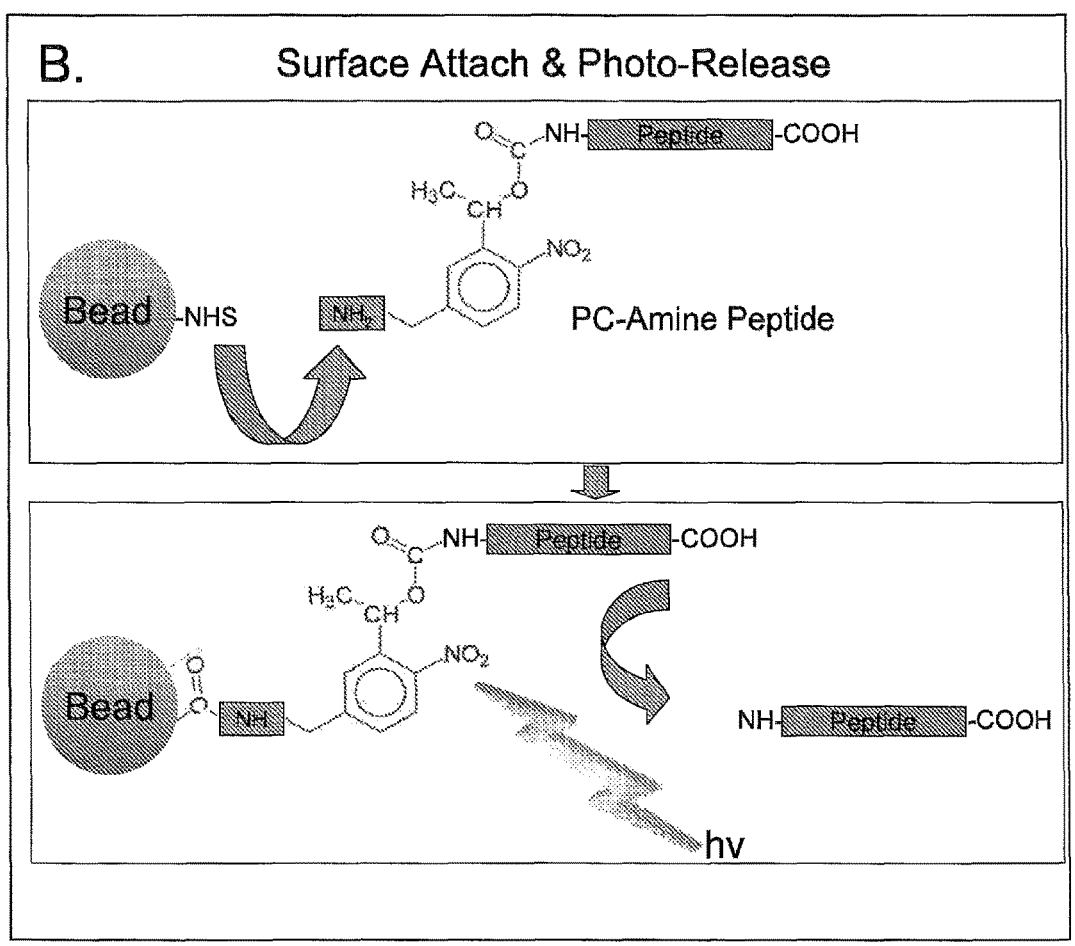

Following preparation of the photocleavable mass tags as described above, experiments will be performed similar to Example 13, except that instead of attachment of photocleavable biotin labeled peptide mass tags to NeutrAvidin coated beads, the photocleavable amine modified peptide mass tags synthesized here will be directly attached to the NHS-activated beads (FIG. 14B). This mass tag attachment will be done simultaneously with the attachment of the anti-HSV capture antibody to the NHS-activated beads, under the same buffer conditions (see Examples 6 & 13 for beads and anti-HSV antibody attachment). In this Example, unlike Example 13, there will be no NeutrAvidin or (strept) avidin attached to the beads, as it will net be needed. In this Example, upon illumination with the proper light, the directly and covalently attached mass tags will be photo-released from the beads (FIG. 14B). In this way, MALDI-TOF mass-imaging of mass tag encoded beads arrayed in the pico-well plates will be possible, analogous to experiments in Example 13.

One expected benefit will be less background noise in assay readout (e.g. probe detection) and generally less interference with downstream assays due to the lack of a NeutrAvidin or (strept)avidin coating on the beads (e.g. less interference with assays involving in situ, on-bead protease digestion of bead-bound proteins such as in Example 9).

In a related embodiment that will be evaluated, a compound similar to the "Photocleavable Amine Linker" shown in the upper left panel of FIG. 14A will be synthesized, except that the protected amine group in the (green and red boxes) will be replaced by a sulfhydryl-reactive maleimide group, to create a bi-functional photocleavable cross-linker. In this scenario, the NHS reactive portion of the compound will still be used to modify a mass-tag (e.g. peptide), such as discussed above in this Example and shown in FIG. 14A, however, instead of subsequently attaching the modified mass-tag to a bead surface (although still possible with this compound), it will subsequently be attached to a probe ("prey"), such as an antibody, which contains native or added sulfhydryl groups for modification. In this manner, the probe, which will now bear a photocleavable mass-tag, can be used query beads for example, such as done in Examples 7 and 12, to allow readout of the probe binding by MALDI-TOF mass-imaging of the beads. This will allow mass-tag coding of different probe ("prey") molecules, as well as mass-tag coding of entire bio-samples or heterogeneous mixtures (e.g. a blood serum sample), to facilitate multiplexing at the level of the probes or samples used to query beads.

Example 15. Mass Spectrometry Readout and Mass-Imaging from Individually Resolved 34 Micron Beads in Metal Coated Pico-Well Plates In this Example, fluorescence imaging and MALDI-TOF mass-imaging of beads in plain and gold-coated pico-well plates was evaluated. Conductive surfaces are typically more ideal for MALDI-TOF as they avoid charge buildup.
Pico-Well Plates Pico-well plates (Incom Inc., Charlton, Mass.) as described in Example 3 were either used as is, or coated with a thin layer of gold by the manufacturer (Incom Inc., Charlton, Mass.). Briefly, coating involves plasma cleaning of the plates, then sputtering on a thin coat of titanium to promote adhesion of gold to the glass, and then applying a 5 nm layer of gold on top of that. SEM (scanning electron microscopy), EDX (energy dispersive X-ray analysis) and AFM (atomic force microscopy) were used by the manufacturer to verify uniform coating of the plates.
Preparation of Dual Affinity Beads Coated with Both NeutrAvidin and the Anti-HSV Tag Capture Antibody Performed as in Example 6
Preparation of Photocleavable (PC) Biotin Labeled Peptide Mass Tags Performed in the same manner as in Example 5 except that the bradykinin peptide (Sigma-Aldrich, St. Louis, Mo.) (RPPGFSPFR) was used instead of the VSV-G peptide in Example 5.
Binding of PC-Biotin Peptide Mass Tags to Dual Affinity Beads Performed as in Example 6 except that 200 µL of PC-Biotin peptide mass tag solution at a concentration of 0.75 pmoles/µL (150 pmoles) was added to a 1 µL bead pellet volume (30,000 beads); for a final added amount of PC- Biotin peptide mass tag of 5 fmoles per bead. As in Example 6, this step is to capture the PC-Biotin peptide mass tags on the dual affinity beads byway of the NeutrAvidin coating on the beads (peptide capture efficiency not measured).

Binding of Recombinant Protein as "Bait" to Dual Affinity Beads

Beads with the bradykinin mass-tag were loaded with cell-free expressed recombinant human p53 protein essentially as in Example 6 with the following exceptions: Treatment of the beads with the cell-free expression reaction for recombinant p53 protein capture was performed as in Example 6, except that immediately following completion of the expression reaction (prior to mixing with beads), protease inhibitor was additionally added to the expression reaction to reduce the possibility of subsequent proteolytic degradation of the peptide mass tags on the beads ("Complete Mini Protease Inhibitor Cocktail Tablets" form Roche Applied Science, Indianapolis, Ind., Catalog Number 11836153001; Stock Solution=1 mini-tablet in 1 mL of purified water; add 1/10 volume of Stock Solution to completed cell-free protein expression reactions). As in Example 6, the mechanism of capture of the cell-free expressed recombinant p53 protein on the dual affinity beads is by way of the anti-HSV antibody coating on the beads and the C-terminal HSV epitope tag present in the recombinant p53. Finally, after loading the recombinant p53 protein onto the bradykinin encoded beads, washing was 4× 400 μL briefly with TBS-T and 2× 400 μL briefly with Block Buffer (see Example 3 for buffer compositions).

Pooling Beads and Fluorescence Detection of p53 Beads

Beads were then probed with a fluorescently labeled anti-VSV-Cy3 antibody to specifically detect the p53 beads, by way of the VSV epitope tag present in the recombinant p53. The fluorescence antibody probing was performed as in Example 3 in the section headed "Verification of Bound Recombinant Proteins". For both the plain glass and gold-coated pico-well plates, imaging of fluorescence was performed through the bottom of the plates (i.e. thorough the fiber optics).

In Situ Trypsinization for Gold Versus Glass Comparison

In a second experiment, beads were created carrying recombinant proteins captured via the anti-HSV antibody similar to as earlier in this Example, but without any mass-tags and without any antibody probing steps. Beads were deposited into gold-coated and glass pico-well plates and in situ trypsin digestion was performed similar to as in Example 8, In this example human ACVR-2B was used as the recombinant protein.

Mass Tag Photocleavage and MALDI-TOF Mass Spectrometry Imaging of Beads

Performed in the plain glass and gold-coated pico-well plates as in Examples 5 & 7. Photocleavage was not used for in situ trypsin digested samples.

Figure 15A:
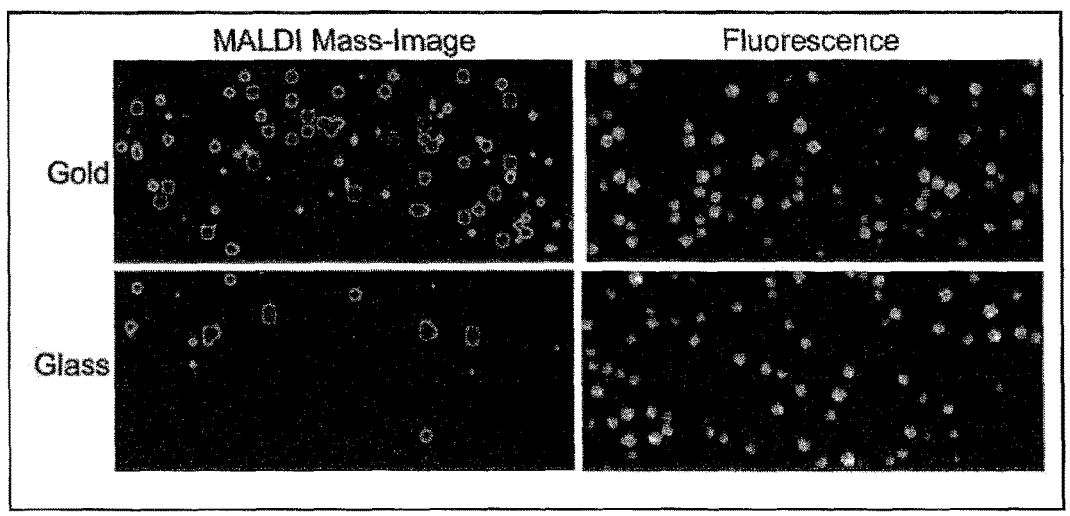

Results:

Results in FIG. 15A show MALDI-TOF mass-imaging of the photocleavable bradykinin mass-tag and fluorescence imaging of the anti-p53 antibody probe from the 34 micron beads in both the gold-coated and plain glass pico-well plates. Note that the fluorescence and MALDI-TOF images are of different regions of the plate in this Example. The data show that individually resolved beads can be imaged both by MALDI-TOF and by fluorescence in both the gold-coated and plain glass pico-well plates. Note that the contrast settings of the fluorescence images in FIG. 15A for the gold-coated and plain glass pico-well plates are not the same and thus cannot be directly compared in FIG. 15A. However, based on the actual raw fluorescence intensity values, the gold-coated plates produced a weaker fluorescence signal by approximately 2-3 fold.

Figure 15B:
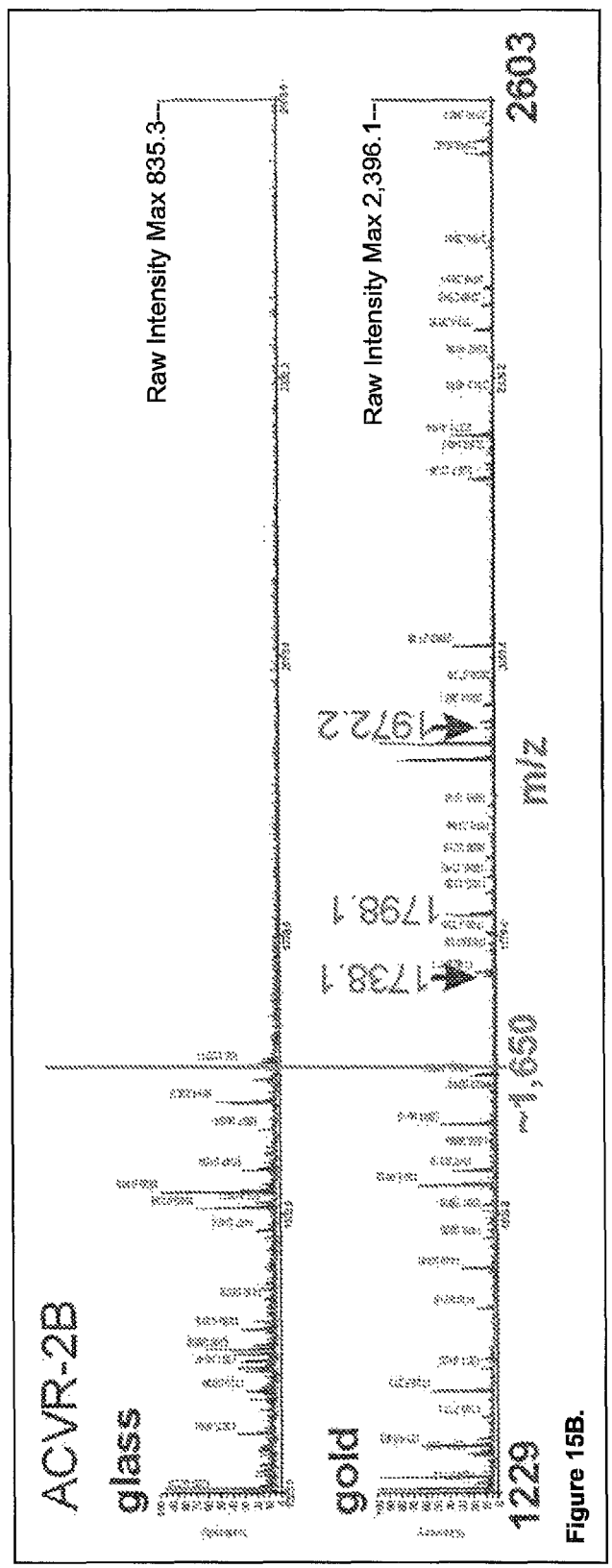

Results in FIG. 15B show direct comparison of MALDI-TOF spectra from beads in both the gold-coated and plain glass pico-well plates following in situ trypsin digestion of bead-bound human recombinant ACVR-2B. Various peptide peaks are visible in both types of pico-well plates, arising from proteolytic fragments of the ACVR-2B and capture antibody, as well as non-specifically bound peptides (e.g. from the expression lysate). However, the gold-coated plates produce more detectible fragments and an overall signal increase of roughly 2-fold (see "Raw Intensity Max" scale on the right-hand y-axis for quantitative comparison). Furthermore, the gold-coated plates allow a greater range of mass coverage. While the plain glass pico-well plates show virtually no detectible peptides above 1,650 Da (see green markings in FIG. 15B), the gold-coated plates show a multitude of peptides >1,650 Da. Finally, in this Example, only the gold-coated plates yield peptide fragments which can be assigned to ACBR-2B protein sequence based on their mass (see red labels in FIG. 15B).

Example 16. MALDI-TOF Mass-Imaging of Multiple Unique Photocleavable Mass-Tag Encoded Bead Species in an Array: Synchronizing Mass-Image for Bead Identification with Fluorescence Antibody Detection of a Bead-Bound Bait Protein In this Example, 2 distinct species of beads, each carrying a unique photocleavable (PC) peptide mass tag, and 1 of the 2 additionally carrying bound recombinant p53 protein ("bait"), were prepared separately, pooled and then probed with a fluorescently labeled antibody ("prey") to detect the recombinant p53 protein. A 3rd bead species was then spiked in as "Marker Beads". These Marker Beads carried a unique photocleavable peptide mass tag for identification and the bead surface was covalently labeled with a fluorophore having different and distinguishable spectral properties than that used on the antibody probe. The pool of 3 bead species was randomly arrayed in the pico-well plates and then imaged by mass and by fluorescence.

Preparation of NeutrAvidin Coated Beads

NeutrAvidin coated 34 micron agarose beads were prepared as in Example 5. As described below, these NeutrAvidin beads were used to prepare both the "Dual Affinity Beads" and the "Marker Beads".

Preparation of Dual Affinity Beads Coated with NeutrAvidin Directly and Indirectly with the Anti-HSV Tag Capture Antibody The aforementioned NeutrAvidin beads were then loaded a biotin labeled anti-HSV tag polyclonal antibody as follows; Goat anti-HSV tag polyclonal antibody was purchased from Bethyl Laboratories (Montgomery, Tex.), provided at 1 mg/mL in PBS. 800 μL of this antibody solution (800 μg) was then mixed with $\frac{1}{9}^{th}$ volume of 1M sodium bicarbonate. The antibody was biotin labeled by adding a 10-fold molar excess of EZ-Link-Sulfo-NHS-LC-Biotin (Thermo-Fisher-Pierce, Rockford, Ill.) and reacting for 30 min with gentle mixing. The reaction was quenched by adding $\frac{1}{9}^{th}$ volume of 1M glycine for 15 min with gentle mixing. The labeled antibody was then purified on a PD MidiTrap G-25 desalting column against TBS (see Example 3 for buffer) and according to the manufacturer's instructions (GE Healthcare Life Sciences, Piscataway, N.J.). The purified and biotin-labeled antibody was then diluted to 0.15 μg/L in TBS-T (see Example 3 for buffer). Using this solution, the NeutrAvidin beads were coated at a ratio of 12 µg of the biotin labeled anti-HSV tag antibody per each 1 µL of actual bead pellet volume for 30 min with gentle mixing. Beads were then washed 4× briefly with an excess of TBS-T using the aforementioned Filtration Devices (see Example 3 for devices). Beads were stored as a 20% (v/v) suspension at +4° C.

Note that because the antibody does not saturate all the biotin binding sites on the NeutrAvidin beads, it was therefore possible to additionally load PC-Biotin labeled peptide mass tags onto the beads (see later steps in this Example).

Preparation of "Marker Beads" Coated with NeutrAvidin Directly and Labeled with Fluorescence Performed as in Example 6 except that the aforementioned NeutrAvidin beads (no bound antibody) were used for fluorescence labeling and the Cy5-NHS activated (primary amine reactive) fluorescent dye labeling reagent was used (GE Healthcare Life Sciences, Piscataway, N.J.).

Preparation of Photocleavable (PC) Biotin Labeled Peptide Mass Tags

Performed as in Example 5 except that the following commercially available peptides were used for labeling with PC-Biotin (peptide sequence in brackets) (all peptides purchased for labeling were from AnaSpec, Fremont, Calif., except for Bradykinin which was from Sigma-Aldrich, St. Louis, Mo.):

1. Heparin-Binding Peptide V [Trp-Gln-Pro-Pro-Arg-Ala-Arg-Ile]; 1023 Da
2. [D-Phe7]-Bradykinin [Arg-Pro-Pro-Gly-Phe-Ser-D-Phe-Phe-Arg]; 1111 Da
3. Bradykinin [Arg-Pro-Pro-Gly-Phe-Ser-Pro-Phe-Arg]; 1060 Da Binding of PC-Biotin Peptide Mass Tags to Dual Affinity Beads Performed as in Example 6 except that 150 µL of PC-Biotin peptide mass tag solution, at a concentration of 5 pmoles/µL (750 pmoles peptide mass tag), was added to a 1 µL bead pellet volume (30,000 beads); for a final added amount of biotin-labeled peptide mass tag of 25 fmoles per bead. As in Example 6, this step is to capture the PC-Biotin labeled peptide mass tags on the beads by way of the NeutrAvidin coating on the beads (peptide capture efficiency not measured). In this Example, 3 separate batches of beads were prepared, each batch uniquely loaded with 1 of the 3 aforementioned peptide species, creating 3 pure populations of unique mass tag encoded beads. The Bradykinin mass tag was loaded onto the aforementioned "Marker Beads" (NeutrAvidin beads with direct fluorescent label attached to beads) while all other mass tags were loaded onto the aforementioned "Dual Affinity Beads" (NeutrAvidin beads additionally containing a common capture antibody for tagged recombinant proteins).

Binding of Recombinant Protein as "Bait" to Dual Affinity Beads

The following was performed on all bead species (kept separate) except the "Marker Beads" which were not subjected to the procedures in the paragraph below:

Beads with the "Heparin-Binding Peptide V" identification tag were loaded with cell-free expressed recombinant human p53 protein essentially as in Example 6 with the following exceptions: Treatment of the beads with the cell-free expression reaction for recombinant p53 protein capture was performed as in Example 6, except that immediately following completion of the expression reaction (prior to mixing with beads), protease inhibitor was additionally added to the expression reaction to reduce the possibility of subsequent proteolytic degradation of the peptide mass tags on the beads ("Complete Mini Protease Inhibitor Cocktail Tablets" form Roche Applied Science, Indianapolis, Ind., Catalog Number 11836153001; Stock Solution=1 mini-tablet in 1 mL of purified water; add ¹/₁₀ volume of Stock Solution to completed cell-free protein expression reactions). As in Example 6, the mechanism of capture of the cell-free expressed recombinant p53 protein on the Dual Affinity Beads is by way of the anti-HSV antibody coating on the beads and the C-terminal HSV epitope tag present in the recombinant p53. Finally, after loading the recombinant p53 protein onto the "Heparin-Binding Peptide V" encoded beads, washing was 4× 400 µL briefly with TBS-T. Beads with the "[D-Phe7]-Bradykinin" identification tag were also subjected to the same above procedure, except that a blank cell-free expression reaction was used as a negative control instead of a p53 cell-free expression reaction. In this case, the cell-free expression reaction lacked the cognate expressible p53 DNA.

Pooling Beads and Fluorescence Detection of p53 Beads

All bead species, except "Marker Beads" which were added later, were then pooled in equal numbers (2 species). The pooled beads were then probed with a fluorescently labeled anti-p53 antibody to specifically detect the p53 containing beads. The fluorescently labeled anti-p53 antibody was prepared in the same manner as the fluorescently labeled NeutrAvidin described in Example 7, except that the anti-p53 antibody (clone BP53-12, Santa Cruz Biotechnology, Santa Cruz, Calif.) was used at 0.2 mg/mL in PBS and the Alexa Fluor® 594 SSE labeling reagent (Invitrogen, Carlsbad, Calif.) was used. The anti-p53 fluorescence antibody probing was performed similar to as in Example 3 in the section headed "Verification of Bound Recombinant Proteins". After fluorescence probing, "Marker Beads" were spiked in at an approximate equal ratio to the other bead species.

Mass Tag Photocleavage and MALDI-TOF Mass Spectrometry Imaging of Beads

Performed in the pico-well plates as in Examples 5 & 7.

Fluorescence Imaging of Pico-Well Plates

After MALDI-TOF mass-imaging, the pico-well plates were fluorescently imaged using a GenePix 4200 laser based microarray scanner (Molecular Devices, Sunnyvale, Calif.). This is possible because the fluorescent antibody probe is not significantly depleted during the MALDI-TOF process. However, fluorescence imaging could be achieved either before or after MALDI-TOF mass-imaging with comparable results. Furthermore, pico-well plates could be imaged from the bottom (through fiber optics) or from the top, with comparable results, despite the presence of MALDI matrix crystals on the top surface of the plate. Finally, fluorescence imaging before matrix application and before MALDI-TOF was also possible, again with similar results.

Figure 16A:
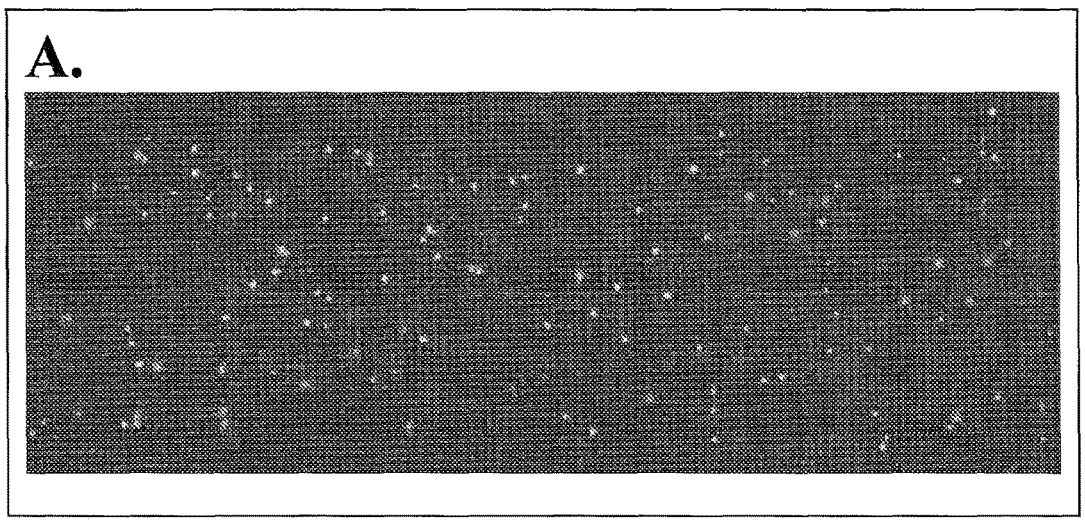
Figure 16B:
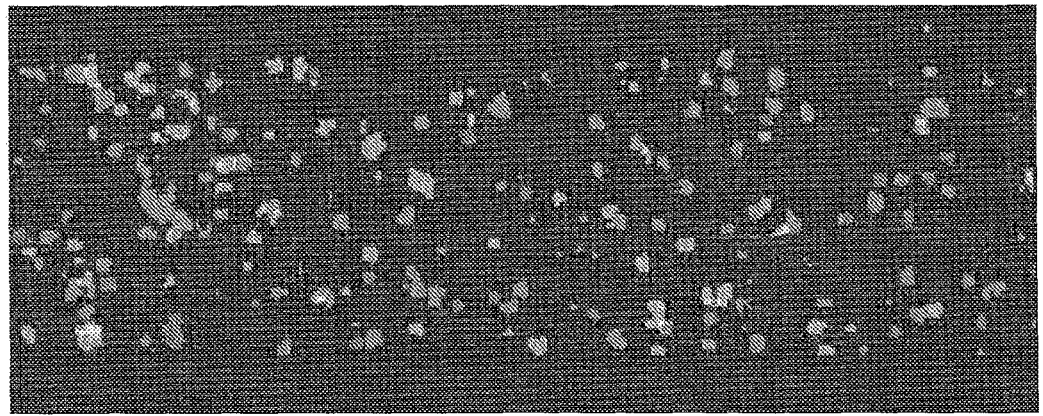

Results:

The same region of the pico-well plate was imaged by both MALDI-TOF and fluorescence. Results are shown in FIG. 16A-B. In FIG. 16A, a 2-color fluorescence image is shown. Red spots are the "Marker Beads" and yellow spots are the p53 positive beads as detected with the anti-p53 antibody probe. Negative control blank beads are not visible in this image (separate fluorescence images of p53 positive and negative beads show a signal-to-noise ratio of >100:1; negative beads are visualized at very high image contrast settings, by way of weak non-specific fluorescence and auto-fluorescence background; image not shown). FIG. 16B is a color-coded MALDI-TOF mass image of the same region, showing the localization of the 3 different photocleavable mass tags in the array (based on their respective m/z). In FIG. 16B, blue is the "Bradykinin" mass tag which encodes the "Marker Beads", green is the "Heparin-Binding Peptide V" mass tag which encodes the p53 beads and red the "[D-Phe7]-Bradykinin" mass tag which encodes the negative control blank beads. This data shows distinct spots corresponding to beads carrying unique photocleavable mass tags, and little spatial overlap between the 3 different mass tags in this experiment.

Figure 16C:
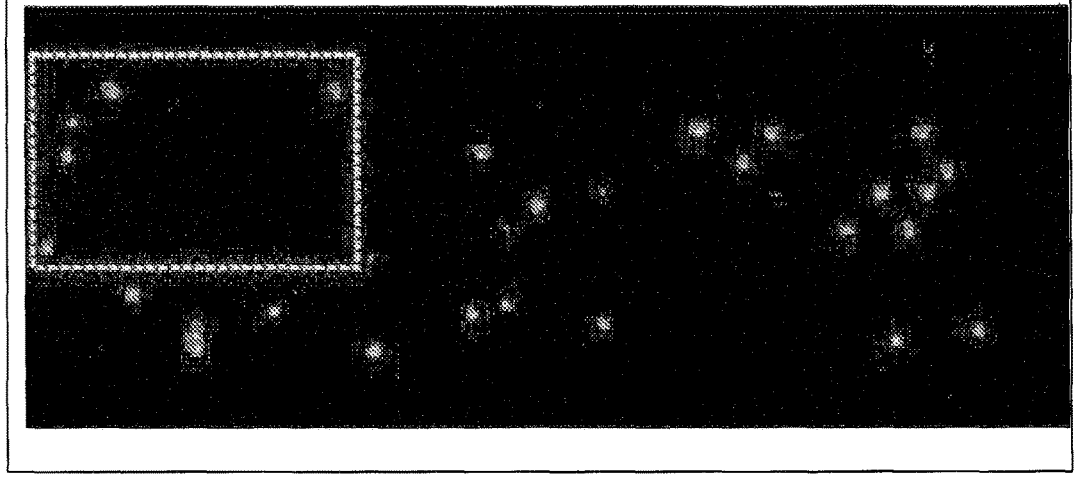
Figure 16D:
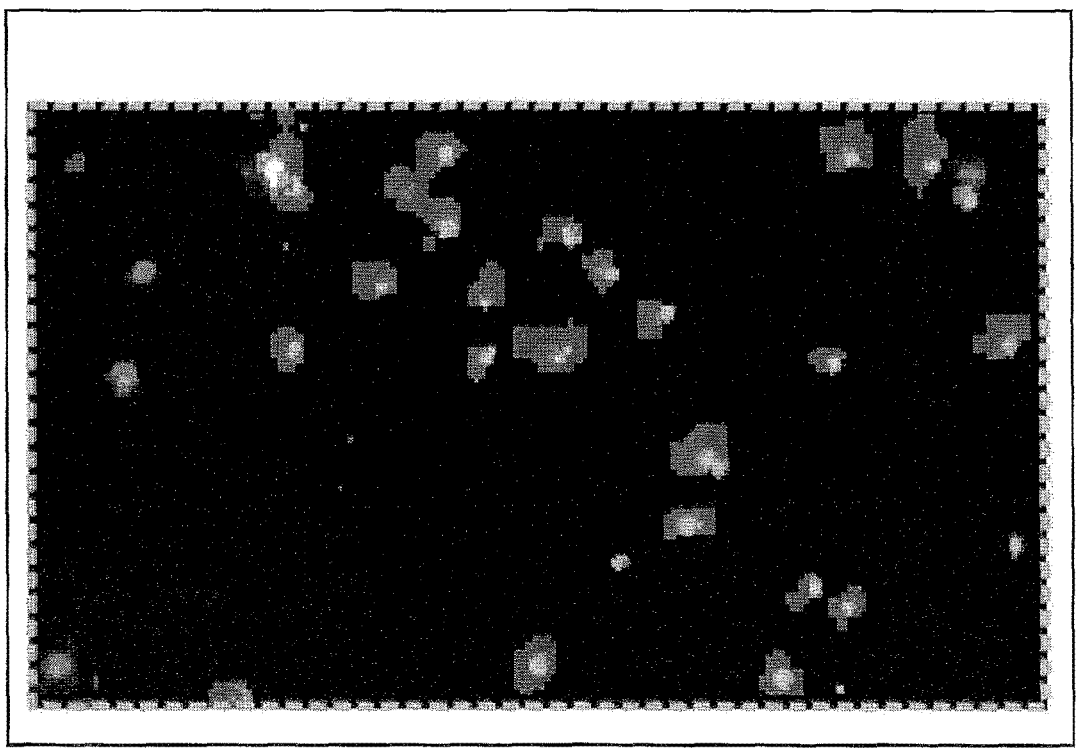
Figure 16E:
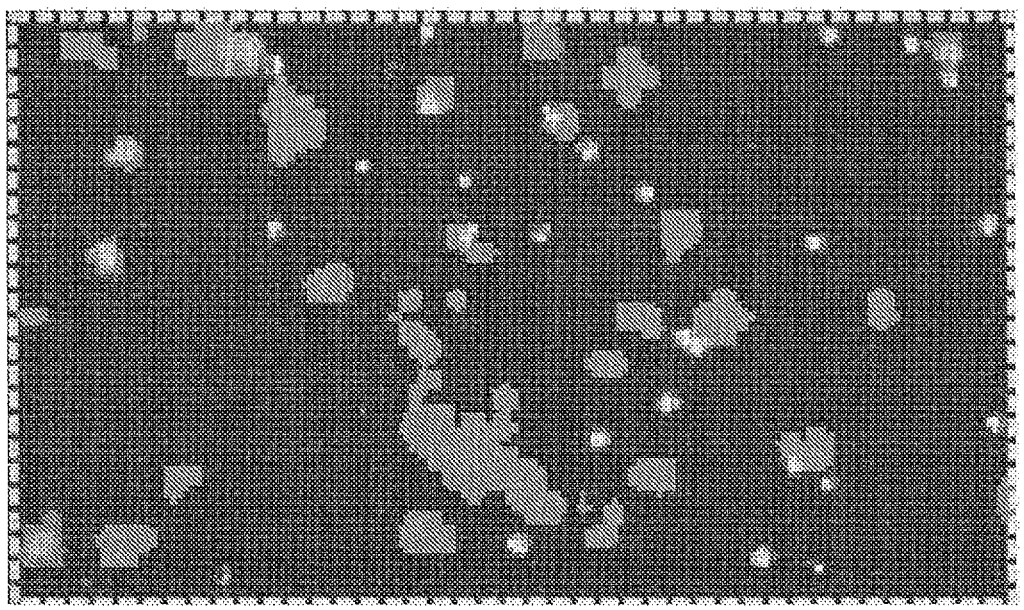

FIGS. 16C-E are direct (i.e. not offset) overlays of fluorescence images and MALDI-TOF mass images. Alignment of MALDI-TOF and fluorescence images was always based on the fluorescence and mass signals arising from the "Marker Beads". FIG. 16C is an overlay of the fluorescence from the "Marker Beads" (red) and the mass tag encoding those beads (blue). As seen, there is near 100% concordance between the fluorescence and MALDI-TOF images of the beads (overlapping colors appear as pink spots). FIG. 16D shows a sub-region (yellow boxed region from FIG. 16C) and corresponds to overlaid fluorescence and MALDI-TOF images from both the "Marker Beads" and the p53 beads. Fluorescence arising from "Marker Beads" is again shown in red, and the mass tag encoding those beads is shown in blue (overlap again observed as pink). Fluorescence arising from the anti-p53 antibody probe (p53 positive beads) is again shown in yellow and the mass tag encoding those beads shown in green. In this image, 100% correlation between the "Marker Bead" fluorescence and the corresponding mass tag encoding those beads is again observed. Likewise, excellent concordance is observed between the p53 positive beads as detected by florescence (yellow) and the corresponding mass tag encoding those beads (green). Of approximately 30 distinguishable p53 beads in this field of view, only a 3-4 false negative beads are observed, that were detected by fluorescence but not by MALDI-TOF mass imaging. Note that in some cases the green color (mass tag) masks the yellow (fluorescence) in the presented image, and that there are no false positive p53 beads, that is, beads detected with the mass tag but not fluorescence. In FIG. 16E, overlaid fluorescence and MALDI-TOF images are shown for the anti-p53 fluorescent antibody probe (yellow) and the mass tag encoding the negative control blank beads (red), for the same sub-region as in FIG. 16D ("Marker Beads" again shown as pink due to their respective overlapping colors). As expected, while the "Marker Bead" images correlate as before, there is poor overlap between the anti-p53 fluorescence (yellow) and the mass tag encoding the negative control blank beads (red) which lack recombinant p53.

Taken together, these data show strong concordance between the mass tag encoding the p53 beads in the MALDI-TOF mass image and the fluorescence image of the anti-p53 antibody probe, and that this concordance is non-random (due to lack of overlap from "Marker Beads" and negative control blank beads).

Example 17. MALDI-TOF Mass-Imaging of Multiple Unique Photocleavable and Non-Cleavable Mass-Tag Encoded Bead Species in an Array: Synchronizing Mass-Image for Bead Identification with Fluorescence Antibody Detection of a Bead-Bound Bait Protein In this Example, 10 distinct species of beads, each carrying a unique peptide mass tag, and 1 of the 10 additionally carrying bound recombinant p53 protein ("bait"), were prepared separately, pooled and then probed with a fluorescently labeled antibody ("prey") to detect the recombinant p53 protein. An 11$^{th}$ bead species was then spiked in as "Marker Beads". These Marker Beads carried a unique peptide mass tag for identification and the bead surface was covalently labeled with a fluorophore having different and distinguishable spectral properties than that used on the antibody probe. The pool of 11 bead species was randomly arrayed in the pico-well plates and then imaged by mass and by fluorescence.

Finally, it should be noted that 10 of the 11 peptide mass-tags used were attached to the beads by a photocleavable biotin (including on p53 beads and Marker Beads), while the 11$^{th}$ was attached via a modified reduced-affinity non-cleavable biotin, in order to additionally demonstrate the possibility of using non-cleavable affinity-bound mass tags.

Preparation of NeutrAvidin Coated Beads

NeutrAvidin coated 34 micron agarose beads were prepared as in Example 5. As described below, these NeutrAvidin beads were used to prepare both the "Dual Affinity Beads" and the "Marker Beads".

Preparation of Dual Affinity Beads Coated with NeutrAvidin Directly and Indirectly with the Anti-HSV Tag Capture Antibody The aforementioned NeutrAvidin beads were then loaded a biotin labeled anti-HSV tag polyclonal antibody as follows: Goat anti-HSV tag polyclonal antibody was purchased from Bethyl Laboratories (Montgomery, Tex.), provided at 1 mg/mL in PBS. 800 µL of this antibody solution (800 µg) was then mixed with 1/9$^{th}$ volume of 1M sodium bicarbonate. The antibody was biotin labeled by adding a 10-fold molar excess of EZ-Link-Sulfo-NHS-LC-Biotin (Thermo-Fisher-Pierce, Rockford, Ill.) and reacting for 30 min with gentle mixing. The reaction was quenched by adding 1/9$^{th}$ volume of 1M glycine for 15 min with gentle mixing. The labeled antibody was then purified on a PD MidiTrap G-25 desalting column against TBS (see Example 3 for buffer) and according to the manufacturer's instructions (GE Healthcare Life Sciences, Piscataway, N.J.). The purified and biotin-labeled antibody was then diluted to 0.15 µg/µL in TBS-T (see Example 3 for buffer). Using this solution, the NeutrAvidin beads were coated at a ratio of 12 µg of the biotin labeled anti-HSV tag antibody per each 1 µL of actual bead pellet volume for 30 min with gentle mixing. Beads were then washed 4× briefly with an excess of TBS-T using the aforementioned Filtration Devices (see Example 3 for devices). Beads were stored as a 20% (v/v) suspension at +4° C.

Note that because the antibody does not saturate all the biotin binding sites on the NeutrAvidin beads, it was therefore possible to additionally load biotin labeled peptide mass tags onto the beads (see later steps in this Example).

Preparation of "Marker Beads" Coated with NeutrAvidin Directly and Labeled with Fluorescence Performed as in Example 6 except that the aforementioned NeutrAvidin beads (no bound antibody) were used for fluorescence labeling and the Cy5-NHS activated (primary amine reactive) fluorescent dye labeling reagent was used (GE Healthcare Life Sciences, Piscataway, N.J.).

Preparation of Photocleavable (PC) and Non-Cleavable Biotin Labeled Peptide Mass Tags Performed as in Example 5 except that the following commercially available peptides were used for labeling (peptide sequence in brackets) (all peptides purchased for labeling were from AnaSpec, Fremont, Calif., except for Bradykinin which was from Sigma-Aldrich, St. Louis, Mo.):

1. Heparin-Binding Peptide V [Trp-Gln-Pro-Pro-Arg-Ala-Arg-Ile]; 1023 Da
2. Alpha-Bag Cell Peptide (1-9) [Ala-Pro-Arg-Leu-Arg-Phe-Tyr-Ser-Leu]; 1122 Da
3. [D-Phe7]-Bradykinin [Arg-Pro-Pro-Gly-Phe-Ser-D-Phe-Phe-Arg]; 1111 Da
4. Antioxidant Peptide B [Thr-Arg-Asn-Tyr-Tyr-Val-Arg-Ala-Val-Leu]; 1254 Da
5. Beta-Casomorphin (1-6), Bovine [Tyr-Pro-Phe-Pro-Gly-Pro]; 676 Da
6. [Leu8, Des-Arg9]-Bradykinin [Arg-Pro-Pro-Gly-Phe-Ser-Pro-Leu]; 870 Da
7. [Ile-Ser]-Bradykinin (T-Kinin) [Ile-Ser-Arg-Pro-Pro-Gly-Phe-Ser-Pro-Phe-Arg], 1260 Da
8. [Des-Arg1]-Bradykinin [Pro-Pro-Gly-Phe-Ser-Pro-Phe-Arg]; 905 Da
9. LRRASLG [Leu-Arg-Arg-Ala-Ser-Leu-Gly]; 772 Da
10. Thrombin Receptor (42-48) Agonist, Human [Ser-Phe-Leu-Leu-Arg-Asn-Pro]; 846 Da
11. Bradykinin [Arg-Pro-Pro-Gly-Phe-Ser-Pro-Phe-Arg]; 1060 Da All above peptides were labeled on their N-terminus with the amine-reactive PC-Biotin-NHS reagent, as detailed in Example 5, except for "Alpha-Bag Cell Peptide (1-9)", which was labeled with the amine-reactive DSB-XTM Biotin SSE labeling reagent (Invitrogen, Carlsbad, Calif.) using the same protocol as in Example 5. DSB-XTM Biotin is a modified biotin derivative that has reduced affinity for (strept)avidin, believed to be several orders of magnitude weaker, and therefore can be dissociated from (strept)avidin under comparatively mild conditions [Hirsch, Eslamizar, Filanoski, Malekzadeh, Haugland and Beechem (2002) Anal Biochem 308: 343-57]. While the native biotin moiety (ring structure) of the PC-Biotin labeled peptide mass tags is poorly dissociated from NeutrAvidin beads by the MALDI-TOF process (see Example 5), it was expected that the lower affinity binding of DSB-XTM Biotin would allow efficient dissociation of the mass tags via the denaturing MALDI-TOF matrix solution and/or by the energy introduced by the MALDI laser.

Binding of PC-Biotin Peptide Mass Tags to Dual Affinity Beads

Performed as in Example 6 except that 150 µL of PC-Biotin or DSB-XTM Biotin peptide mass tag solution, at a concentration of 5 pmoles/µL (750 pmoles peptide mass tag), was added to a 1 µL bead pellet volume (30,000 beads); for a final added amount of biotin-labeled peptide mass tag of 25 fmoles per bead. As in Example 6, this step is to capture the biotin-labeled peptide mass tags on the beads by way of the NeutrAvidin coating on the beads (peptide capture efficiency not measured). In this Example, 11 separate batches of beads were prepared, each batch uniquely loaded with 1 of the 11 aforementioned peptide species, creating 11 pure populations of unique mass tag encoded beads. The Bradykinin mass tag was loaded onto the aforementioned "Marker Beads" (NeutrAvidin beads with direct fluorescent label attached to beads) while all other mass tags were loaded onto the aforementioned "Dual Affinity Beads" (NeutrAvidin beads additionally containing a common capture antibody for tagged recombinant proteins).

Binding of Recombinant Protein as "Bait" to Dual Affinity Beads

Although in some embodiments all mass tagged bead species can additionally carry a "bait" molecule such as a protein, in this Example, with the exception of the "Alpha-Bag Cell Peptide (1-9)" and "Heparin-Binding Peptide V" mass tag encoded beads, the other 10 mass tagged bead species were not loaded with cell-free expressed recombinant protein and thus not subjected to this portion of the procedure:

Beads with the "Alpha-Bag Cell Peptide (1-9)" identification tag were loaded with cell-free expressed recombinant human p53 protein essentially as in Example 6 with the following exceptions: Treatment of the beads with the cell-free expression reaction for recombinant p53 protein capture was performed as in Example 6, except that immediately following completion of the expression reaction (prior to mixing with beads), protease inhibitor was additionally added to the expression reaction to reduce the possibility of subsequent proteolytic degradation of the peptide mass tags on the beads ("Complete Mini Protease Inhibitor Cocktail Tablets" form Roche Applied Science, Indianapolis, Ind., Catalog Number 11836153001; Stock Solution=1 mini-tablet in 1 mL of purified water; add 1/10 volume of Stock Solution to completed cell-free protein expression reactions). As in Example 6, the mechanism of capture of the cell-free expressed recombinant p53 protein on the Dual Affinity Beads is by way of the anti-HSV antibody coating on the beads and the C-terminal HSV epitope tag present in the recombinant p53. Finally, after loading the recombinant p53 protein onto the "Alpha-Bag Cell Peptide (1-9)" encoded beads, washing was 4× 400 µL briefly with TBS-T, Beads with the "Heparin-Binding Peptide V" identification tag were also subjected to the same above procedure, except that a blank cell-free expression reaction was used as a negative control instead of a p53 cell-free expression reaction. In this case, the cell-free expression reaction lacked the cognate expressible p53 DNA.

Pooling Beads and Fluorescence Detection of p53 Beads

All bead species, except "Marker Beads" which were added later, were then pooled in equal numbers (10 species). The pooled beads were then probed with a fluorescently labeled anti-p53 antibody to specifically detect the p53 containing beads. The fluorescently labeled anti-p53 antibody was prepared in the same manner as the fluorescently labeled NeutrAvidin described in Example 7, except that the anti-p53 antibody (clone BP53-12, Santa Cruz Biotechnology, Santa Cruz, Calif.) was used at 0.2 mg/mL in PBS and the Alexa Fluor® 594 SSE labeling reagent (Invitrogen, Carlsbad, Calif.) was used. The anti-p53 fluorescence antibody probing was performed similar to as in Example 3 in the section headed "Verification of Bound Recombinant Proteins". After fluorescence probing, "Marker Beads" were spiked in at an approximate equal ratio to the other bead species.

Mass Tag Photocleavage and MALDI-TOF Mass Spectrometry Imaging of Beads

Performed in the pico-well plates as in Examples 5 & 7.

Fluorescence Imaging of Pico-Well Plates

After MALDI-TOF mass-imaging, the pico-well plates were fluorescently imaged using a GenePix 4200 laser based microarray scanner (Molecular Devices, Sunnyvale, Calif.). This is possible because the fluorescent antibody probe is not significantly depleted during the MALDI-TOF process. However, fluorescence imaging could be achieved either before or after MALD-TOF mass-imaging with comparable results. Furthermore, pico-well plates could be imaged from the bottom (through fiber optics) or from the top, with comparable results, despite the presence of MALDI matrix crystals on the top surface of the plate. Finally, fluorescence imaging before matrix application and before MALDI-TOF was also possible, again with similar results.

Figure 17A:
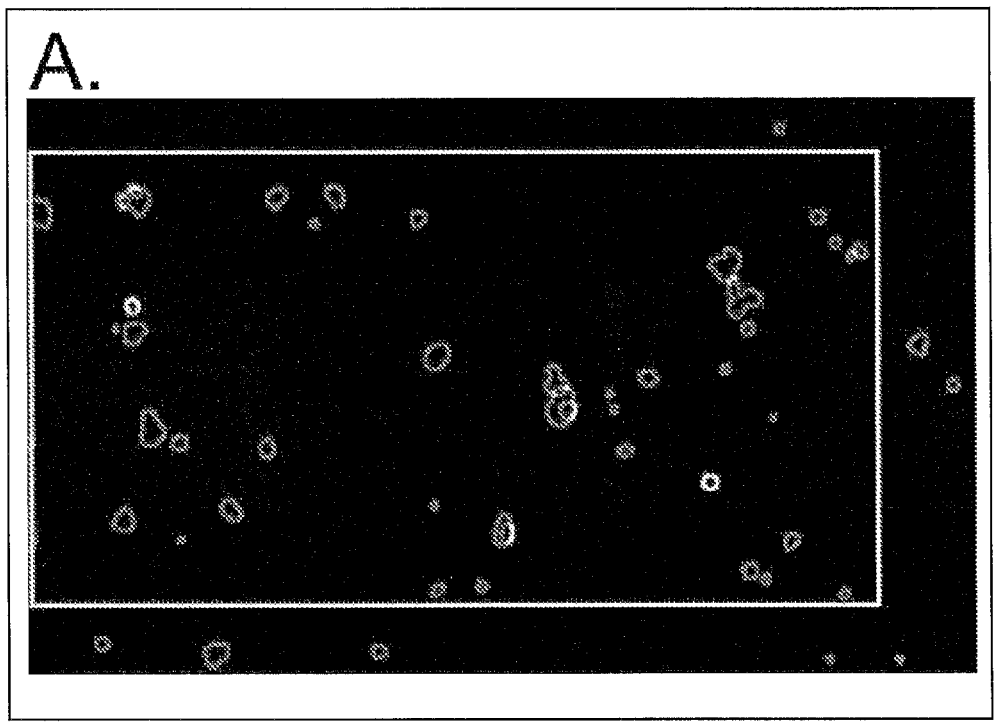
Figure 17B:

Results:

The same 4.8×2.8 mm region of the pico-well plate was imaged by both MALDI-TOF and fluorescence (13.44 mm$^2$; roughly 6,000 wells). Results are shown in FIG. 17A-B. In FIG. 17A, image processing was a follows: Separate grayscale mass-images, corresponding to the m/z for each of the mass tags, were processed using the public domain scientific imaging software ImageJ v1.42q [Rasband, W. S., ImageJ, U. S. National Institutes of Health, Bethesda, Md., USA, http://rsb.info.nih.gov/ij/, 1997-2009; Abramoff, M. D, Magelhaes, P. J., Ram, S. J. "Image Processing with ImageJ". Biophotonics International, volume 11, issue 7, pp. 36-42, 2004]. First, a 2 pixel median filter was applied for noise reduction and then the "Find Edges" algorithm was applied to trace the outlines of individually resolvable "features" (spots) in the images. The resultant images of the spot outlines for each mass tag were then overlaid. Overlapping (intersecting) spot outlines are shown in white in FIG. 17A. In the region scanned and shown in FIG. 17A, all mass tags except the "LRRASLG" peptide (not detected) are represented at least once as individually resolvable non-overlapping spots.

In FIG. 17B, a 5-color hybrid image was created by overlaying the colorized grayscale mass-images of 3 selected mass-tags with the fluorescence images of both the anti-p53 antibody probe and the "Marker Bead" label. Note that the fluorescence images were offset from the mass images to allow visualization of both mass tags and fluorescence arising from the same beads. Fluorescence and mass images were aligned based on the "Marker Beads".

Data in FIG. 17B show that p53 beads detected with the anti-p53 fluorescent antibody (yellow) show excellent concordance with the mass tag encoding the p53 beads (green). 4 of 5 spots are concordant (80%), with one false negative spot detected by fluorescence and not MALDI-TOF (marked with white "X" in FIG. 17B). Conversely, spots identified as the minus p53 negative control beads by virtue of their cognate mass tag (purple), show no concordance with the anti-p53 fluorescence (yellow), as expected. Taken together, these data show that the concordance between the anti-p53 fluorescent antibody probe and the mass tag encoding (identifying) the p53 beads, is not by random chance. Likewise, the fluorescence of the "Marker Beads" (red spots with white center) show 100% concordance with their cognate mass tag (light blue).

Finally, comparison of florescence spot sizes with the MALDI-TOF images of both the "Marker Beads" and p53 beads suggests that the spatial resolution of the MALDI-TOF imaging approaches that of the fluorescence imaging (fluorescence scanned at 10 micron/pixel resolution).

Example 18. Colorimetric Detection of Beads in Pico-Well Plates

In this Example, the ability to detect 34 micron diameter beads in the wells of pico-well plates is shown. In this case, the aforementioned 34 micron diameter agarose beads were coated with streptavidin-HRP and incubated in a precipitating chromogenic HRP substrate (TrueBlue Peroxidase Substrate; KPL Inc., Gaithersburg, Md.). The now opaquely colored beads were deposited into the wells of commercially obtained pico-well plates (PicoTiterm™ Plates designed for 454 Life Sciences GS FLX DNA Sequencer; Roche Applied Science, Indianapolis, Ind.). The PicoTiter™ Plates are similar to the pico-well plates used in previous Examples, except that the slide (plate) thickness is 2 mm instead of 1 mm. Opaquely colored beads were imaged in the wells of the PicoTiter™ Plates using a visible light based ArrayIt SpotWare™ Flatbed Colorimetric Microarray Scanner (TeleChem International, Inc. ArrayIt™ Division, Sunnyvale, Calif.). Results shown in FIG. 18 clearly demonstrate that the beads can be imaged colorimetrically using visible light based techniques (e.g. CCD based visible light imager). In the grayscale image in FIG. 18, wells containing the beads are identified by their dark color (dark spots), whereas empty wells are observed as clear (white spots).

In some embodiments of the technology described in this patent, colorimetric detection of the beads could be used to visualize probe or "prey" binding to "bait" molecules on the beads. Alternatively, colorimetrically detected beads could serve as "landmarks" to direct the MALDI-TOF instrument to specific wells or coordinates in the array.

FIGURES AND TABLES

Description of the Figures for Experimental Examples

FIG. 1. Affinity Purification of Peptides onto an Agarose Bead Resin Followed by Mass Spectrometry Detection from Single Beads. Single agarose beads approximately 75-150 microns in diameter carrying a test peptide immobilized by a bead-bound antibody directed against the peptide's N-terminal FLAG epitope tag were manually selected, deposited on a suitable substrate and scanned using the laser beam of a MALDI-TOF mass spectrometer. The labels in parenthesis correspond to the raw signal intensity of the expected target peak (arbitrary units). The asterisks indicate the minor matrix adduct of the target peak. Spectra from 3 different individual agarose beads are shown.

FIG. 2. Detection and Mass-Imaging of Different Populations of Peptides on Individual Beads Using Scanning MALDI-TOF Mass Spectrometry. Agarose beads approximately 75-150 microns in diameter, each bead carrying one of two possible test peptides immobilized by a bead-bound antibody directed against their common N-terminal FLAG epitope tag, were deposited on a suitable substrate and the substrate scanned using the laser beam of a MALDI-TOF mass spectrometer. The image (left) is a two-color overlay of the two mass-images of the beads, created using spectral intensity at the m/z (mass/charge) corresponding to the molecular weight of the test peptides. Sample spectra (right) are provided from single beads showing that the beads carry a homogeneous population of one peptide.

FIG. 3A-B. Single-Bead MALDI-TOF Mass Spectrometry Mass-Imaging of Unique Mass Tags on 34 Micron Agarose Beads Also Carrying Recombinant Proteins. (FIG. 3A) (top) Color-coded overlaid MALDI-TOF mass spectrometry mass-images of three unique HSV peptide mass tags on individual protein-beads (top panel). Beads are deposited in specialized pico-well plates (substrate), whose dimensions restrict loading to 1 bead/well, prior to MALDI-TOF mass spectrometry mass-imaging of the substrate. Blue="Blank" beads lacking recombinant protein but containing 1,368 Da version of HSV peptide mass tag; Green=human p53 recombinant protein beads containing 2,048 Da version of HSV peptide mass tag; Red=human KLHL recombinant protein beads containing 2,074 Da version of HSV peptide mass tag. Sample spectra (color-coded) are shown for two of the mass tags as detected from single beads (bottom). (FIG. 3B) Separately, fluorescence probing and imaging of an aliquot of beads was performed using a fluorescently labeled (Cy3) anti-VSV-G tag antibody to verify the recombinant proteins are indeed present, by virtue of this common N-terminal epitope tag in all recombinant proteins. "Blank" corresponds to beads processed in the same manner but lacking recombinant protein. Inset "High Contrast" box shows presence of beads in the "Blank" using high contrast image settings.

FIG. 4. Synchronization of Fluorescence Image and Mass Spectrometry Mass-Image of Individually Resolved 34 Micron Agarose Beads in Pico-Well Plates. Two-color overlay. Red=MALDI-TOF mass spectrometry mass-image of an HSV peptide mass tag on beads in a pico-well plate; Green=fluorescence image of peptide mass tag on same beads in same region of pico-well plate. The two images were intentionally offset to show spot concordance.

FIG. 5. MALDI-TOF Mass Spectrometry Mass-Imaging of Photocleavable Mass Tags on Individual 34 Micron Agarose Beads in Pico-Well Plates. [Top] Diagrammatic representation of the experimental design. [Lower Right] MALDI-TOF mass spectrometry mass-image of the photocleaved PC-Biotin VSV-G mass tag peptide from individual beads in the pico-well plate. The beads in the pico-well plate were pre-treated with near-UV light (+UV) to photo-release the mass tag peptide before MALDI-TOF imaging. A section of the plate was masked (−UV) as a negative control. The various experimental permutations performed included with and without the peptide mass tag on the beads ("+Mass Tag" and "−Mass Tag" respectively) and with and without light pre-treatment of the beads (+UV and −UV respectively). A mass-image for the "−Mass Tag+UV" experimental permutation is not shown. [Lower Left] Representative mass spectra are shown from individual beads for all three experimental permutations performed.

FIG. 6A-B. Photocleavable Mass Tags (for Bead Identification) Co-Loaded with "Bait" Molecules for Multiplex Bioassays: "Bait" Detection and Mass Spectrometry Readout from Beads. FIG. 6A. Bead-ELISA results for detection of bead-bound human recombinant p53 "bait" from an entire population of beads. Detection of bead-bound p53 was by virtue of an anti-VSV-G tag antibody conjugated to an enzymatic reporter (chemiluminescence readout); the anti-VSV-G tag antibody binds this epitope tag present in the p53 protein. The p53 signal (i.e. anti-VSV-G epitope tag antibody signal) was normalized to the relative bead amount in each sample ("Normalized p53 Signal") using a separate fluorescence tag conjugated to the bead surface. On the X-axis of the graph, the presence (+) or absence (−) of recombinant human p53 on the beads is indicated, as well as the presence or absence of the PC-Biotin conjugated bradykinin peptide mass tag ("Bradykinin PC-Mass Tag"). FIG. 6B. MALDI-TOF mass spectrometry measurement of the PC-Biotin conjugated bradykinin peptide mass tag ("Bradykinin PC-Mass Tag") (1,060 Da) following photo-release from an aliquot of the same batch of beads.

FIG. 7. Mass-Tagged Probes for MALDI-TOF Mass Spectrometry Mass-Imaging of Individually Resolved Beads: Detection of Serum Autoantibody Against a Bead-Bound Autoantigen by Fluorescence and MALDI-TOF Mass Spectrometry in Pico-Well Plates. The top panel is a diagrammatic representation of the experimental design and the bottom panel is the results. Both fluorescence and MALDI-TOF mass-imaging detect the bound autoantibody. Beads either contained (+) or lacked (−) the human recombinant autoantigen ("Ag.") and were treated with either an autoantibody-positive patient serum (PBC; Primary Biliary Cirrhosis autoimmune serum) or an autoantibody-negative normal patient serum ("Norm"). The fluorescence (Cy3) image (lower left) was intentionally set to a saturating contrast to show the presence of beads in all samples, including the negative controls (by weak non-specific fluorescence). MALDI-TOF mass spectrometry mass-imaging (lower right) was used to detect the photo-released PC-Biotin conjugated VSV-G peptide mass tag from the bound anti-[human IgG] secondary antibody probe on the beads, for autoantibody readout. Sample spectra from individual beads are shown in addition to the mass-image. Note that fluorescence images and mass-images are of different pico-well plates (same batch of beads) and hence not synchronized in this case.

FIG. 8. Application of the Protease Enzyme to the Bead Library Deposited on the Pico-Well Plates: Efficient Protein Digestion without the Loss of Spatial Resolution. Fluorescence scan of the fluorescent Cy3-labeled bead array following trypsin digestion and MALDI matrix deposition measured from the bottom of pico-wells (top image) and the slide surface (bottom image). Inset: region of the MALDI spectrum showing a peak arising from the trypsin digest fragment of p53.

FIG. 9A-C. Measurement of Changes in the Protein Concentration Using a Combination of Protein Isotope Labeling, Proteolytic Digestion and MALDI-TOF Mass Spectrometry Mass-Imaging Analysis of Bead Microarrays. Panel FIG. 9A. Overlay of two mass spectra of pure populations of beads carrying either non-labeled or $^{13}C_6$-Leu-labeled p53 after trypsin digestion showing a mass-shifted peak due to the Leucine incorporation. Panel FIG. 9B. a mass-spectrum in the same region as Panel FIG. 9A obtained after non-labeled and $^{13}C_6$-Leu-labeled p53 were mixed in a 5:1 ratio prior to the bead binding, Panel FIG. 9C. MALDI MSI scan of a bead array containing two populations of beads each carrying either non-labeled or $^{13}C_6$-Leu-labeled p53 after the trypsin digestion. Red spots are areas that exhibit a 1006 Da peak and green spots exhibit a 1018 Da peak. The dotted white line indicated the area of the slide where beads were deposited.

FIG. 10. Decoding of DNA Tags Photo-Released from Beads and Analyzed on a Massively Parallel RT-PCR Chip. DNA-Tags in this case were human gene ORFs. The red numbers above the bar indicate the equivalent number of beads analyzed by the RT-PCR chip.

FIG. 11. Physical Pre-Selection of Beads for Decoding using a Fluorescence Activated Cell-Sorting (FACS) Instrument. Blank beads (control) and autoantigen beads were probed with a positive autoimmune serum and autoantibody detected with a fluorescent (fluorescein) secondary antibody. Beads were the same 34 micron diameter agarose beads used extensively in previous Examples for MALDI-TOF mass spectrometry mass-imaging. The x-axes of the graphs are the channel for detection of autoantibody binding (fluorescein) and the y-axes a control (irrelevant) fluorescence channel.

FIGS. 12A-C. Immune Response Profiling on Beads: Photocleavable (PC) Mass-Tagging and MALDI-TOF Mass-Imaging of the Individually Resolved Beads in an Array. (FIG. 12A.) Schematic of basic experimental design. PC-Mass-Tag encoded beads ("Bead Identification Tag"), carrying either the SmB protein autoantigen or GST A2 as a negative control protein, were probed with a human SLE serum to detect autoantibody binding. The autoantibody probe ("Probe Tag") was also detected with a unique PC-Mass-Tag. (FIG. 12B.) MALDI-TOF mass-image of PC-Mass-Tags from individually resolved beads in an array: (1) Offset image of SmB Bead Identification Tag (green) as well as the autoantibody Probe Tag (red). (2) Same region of the array viewed as 3-color direct mass-image overlay, with the Bead Identification Tag for GST additionally shown in white/gray; co-localization of the green and red mass tag signals from SmB beads shows as yellow spots (not offset). (FIG. 12C.) ELISA analysis on the same SLE serum to validate the results from the bead-based mass-imaging assay. Detection is shown for the "Autoantibody" as well as the "VSV-G Tag" (common tag in both expressed proteins; SmB and GST).

FIGS. 13A-C. MALDI-TOF Mass-Imaging of 10 Distinct Peptide-Bead Species in an Array in Conjunction with Antibody Detection of "Bait" Molecules. (FIG. 13A.) Mass-image of bead array with all 10 peptide species colored red. Beads are 34 microns in diameter. Regions of overlap of any 2 peptide species are shown in yellow. (FIG. 13B.) Mass-image of same region of bead array with each panel showing an image of 1 of the 10 specific peptide species (each panel is different peptide species). (FIG. 13C.) Fluorescence bead image. An aliquot of the same beads was separately imaged by fluorescence to detect the bound antibody probe ("prey") directed against an epitope tag in the recombinant p53 protein ("bait"). Pure populations of "Blank" beads (beads loaded with a blank cell-free expression reaction) and "p53" beads (beads loaded with a p53 cell-free expression reaction) were included as controls. The pooled beads correspond to all 10 bead species including 1 species of uniquely mass-tagged p53 beads and 9 species of uniquely mass-tagged non-p53 beads (no recombinant protein). A "Higher Contrast Image" allows for better visualization of the non-p53 beads, detectible by weak non-specific background fluorescence.

FIGS. 14A-B. Methods of Direct Attachment of Photocleavable Mass Tags to Surfaces Such as Beads. (FIG. 14A) Example structure of an NHS-activated protected-amine linker used to modify the N-terminal of peptide mass tags. The compound ("Photocleavable Amine Linker") has an active NHS ester on one end and a protected amine on the other, with a "Spacer" arm and a photocleavable nucleus ("P") in the center. Note that while a hydrocarbon "Spacer" arm is shown, a multitude of possible structures and lengths can be used. Following peptide modification, the protecting group, e.g. an acid labile group, can be removed to "De-Protect" the amine on the linker. This generates a peptide modified to have a photocleavable primary amine group at its N-terminus ("PC-Amine Peptide"). (FIG. 14B) This photocleavable primary amine group on the peptide can be reacted with NHS activated beads for example (peptide would lack any other free primary amines), thus creating peptides photocleavably linked to the bead surface via a direct covalent attachment. Upon illumination with the proper light ("hv"), the peptide is photo-released from the bead for analysis by mass spectrometry.

FIGS. 15A-B. Mass Spectrometry Readout and Mass-Imaging from Individually Resolved 34 Micron Beads in Metal Coated Pico-Well Plates. (FIG. 15A) MALDI-TOF mass-image of bradykinin mass-tag and fluorescence image of anti-p53 antibody probe from beads in the two types of pico-well plates (plain glass and gold-coated). (FIG. 15B) Comparison of MALDI-TOF spectra from in situ trypsinized human recombinant ACVR-2B from beads in the plain glass and gold-coated pico-well plates. Red labels are peptide fragments that could be correctly assigned to ACVR-2B protein sequence based on mass. The light green line and label indicates the mass above which little to no detectible peptides are observed on the glass pico-well plates.

FIGS. 16A-E. MALDI-TOF Mass-Imaging of Multiple Unique Photocleavable Mass-Tag Encoded Bead Species in an Array: Synchronizing Mass-Image for Bead Identification with Fluorescence Antibody Detection of a Bead-Bound Bait Protein All images shown are direct (i.e. not offset) overlays. (FIG. 16A.) 2-color fluorescence image. Red spots are the "Marker Beads" and yellow spots are the p53 positive beads as detected with the anti-p53 antibody probe. Negative control blank beads are present but not visible in this image. (FIG. 16B.) Color-coded MALDI-TOF mass image of the same region, showing the localization of the 3 different photocleavable mass tags in the array (based on their respective m/z). Blue is the "Bradykinin" mass tag which encodes the "Marker Beads", green the "Heparin-Binding Peptide V" mass tag which encodes the p53 beads and red the "[D-Phe7]-Bradykinin" mass tag which encodes the negative control blank beads. (FIG. 16C-E) Direct (i.e. not offset) overlays of fluorescence images and MALDI-TOF mass images. Alignment of MALDI-TOF and fluorescence images was always based on the fluorescence and mass signals arising from the "Marker Beads". (FIG. 16C) Overlay of the fluorescence from the "Marker Beads" (red) and the mass tag encoding those beads (blue) for the same region of the array (overlapping colors appear as pink spots). (FIG. 16D) Sub-region of the array (yellow box region from panel FIG. 16C.) Corresponds to overlaid fluorescence and MALDI-TOF images from both the "Marker Beads" and the p53 beads. Fluorescence arising from "Marker Beads" is again shown in red, and the mass tag encoding those beads is shown in blue (overlap again observed as pink). Fluorescence arising from the anti-p53 antibody probe (p53 positive beads) is again shown in yellow and the mass tag encoding those beads shown in green. (FIG. 16E.) Overlaid fluorescence and MALDI-TOF images are shown for the anti-p53 fluorescent antibody probe (yellow) and the mass tag encoding the negative control blank beads (red), for the same sub-region as in panel FIG. 16D ("Marker Beads" again shown as pink due to their respective overlapping colors).

FIGS. 17A-B. MALDI-TOF Mass-Imaging of Multiple Unique Photocleavable and Non-Cleavable Mass-Tag Encoded Bead Species in an Array: Synchronizing Mass-Image for Bead Identification with Fluorescence Antibody Detection of a Bead-Bound Bait Protein (FIG. 17A) Overlay of spot (bead) outlines identified by mass-imaging of all mass tags in this experiment. Each individual "spot" (continuous shape) in the presented image corresponds to a single unique mass tag (10 of 11 mass tags detected as an individually resolved spot at least once; 1 mass tag not detected), Overlapping (intersecting) spot outlines are shown in white. (FIG. 17B.) 5-color hybrid image created by overlaying the colorized grayscale mass-images of 3 selected mass-tags with the fluorescence images of both the anti-p53 antibody probe and the "Marker Bead" label. The legend denotes the color-coding in the presented image. Yellow=fluorescence of anti-p53 antibody probe; Green=mass tag encoding p53 containing beads; Purple=mass tag encoding minus p53 negative control beads; Red (with white center)=fluorescence of "Marker Bead" label; Light Blue=mass tag encoding "Marker Beads".

Figure 18:
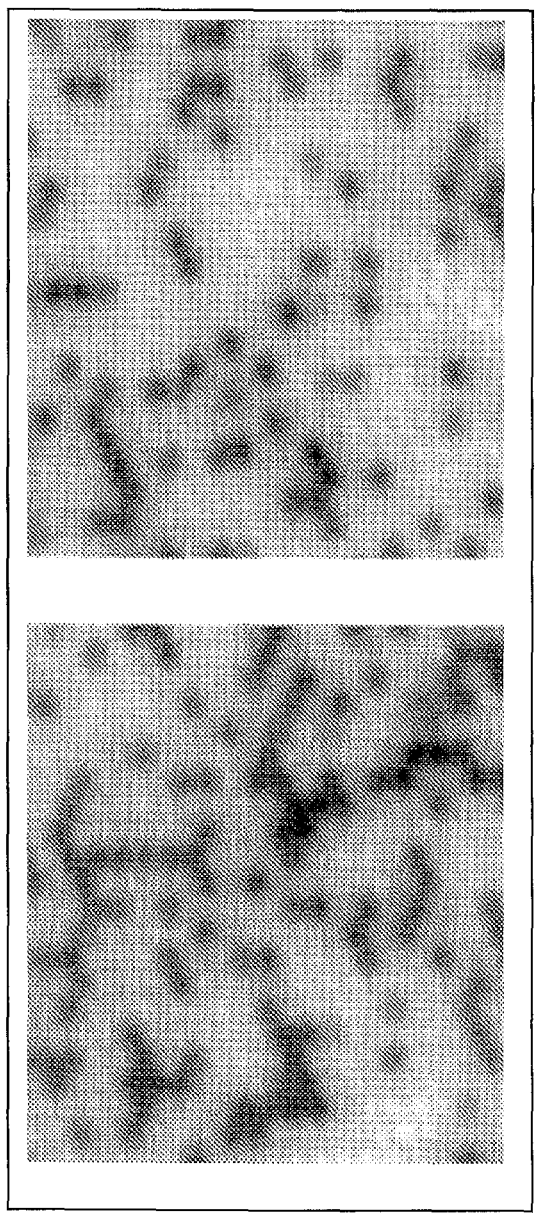

FIG. 18. Colorimetric Detection of Beads in Pico-Well Plates. Opaquely colored beads were deposited into the wells of pico-well plates and imaged using a visible light based colorimetric microarray scanner. In the presented grayscale image (2 fields of view shown), beads in the wells are identified by their dark color (dark spots), whereas empty wells appear as clear (white spots).

Description of the Figures for Specifications

Figure 19:
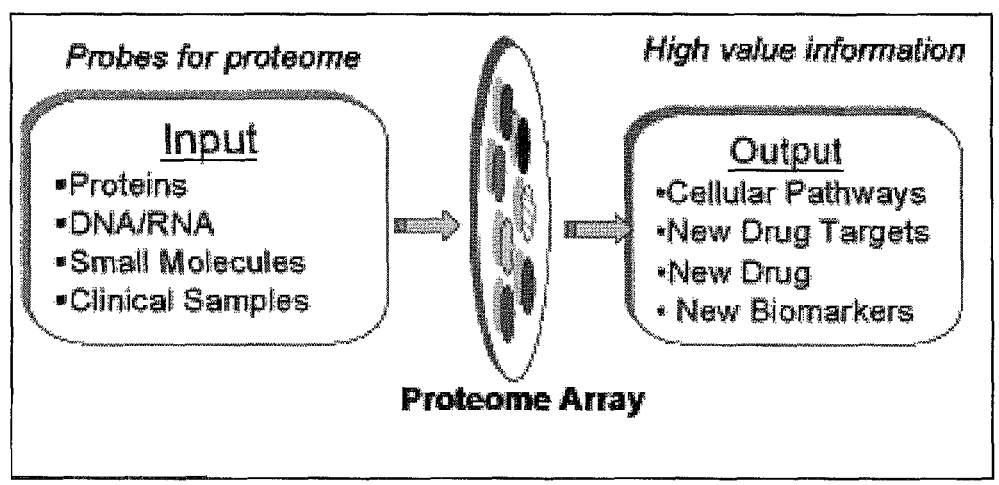

FIG. 19 Proteomic-Wide Screening. A global proteome array provides a powerful means to obtain information about how specific proteins in the proteome interact with a variety of "inputs" such as other proteins, small molecules or complex clinical samples.

FIG. 20 Schematic Showing Two Typical Protein Microarray Configurations. Top: An array of antibodies are deposited on biochip planar surface which selectively capture specific analytes occur, Bottom: Various proteins (e.g. autoantigens) are dried on biochip surface in order to probe molecular interactions such as specific antibody interaction. Typically, fluorescent labeling of captured or interacting species is used for detection (read-out). Adapted from http://www.elmat.lth.se/uploads/pics/Fig1.jpg.

Figure 21:
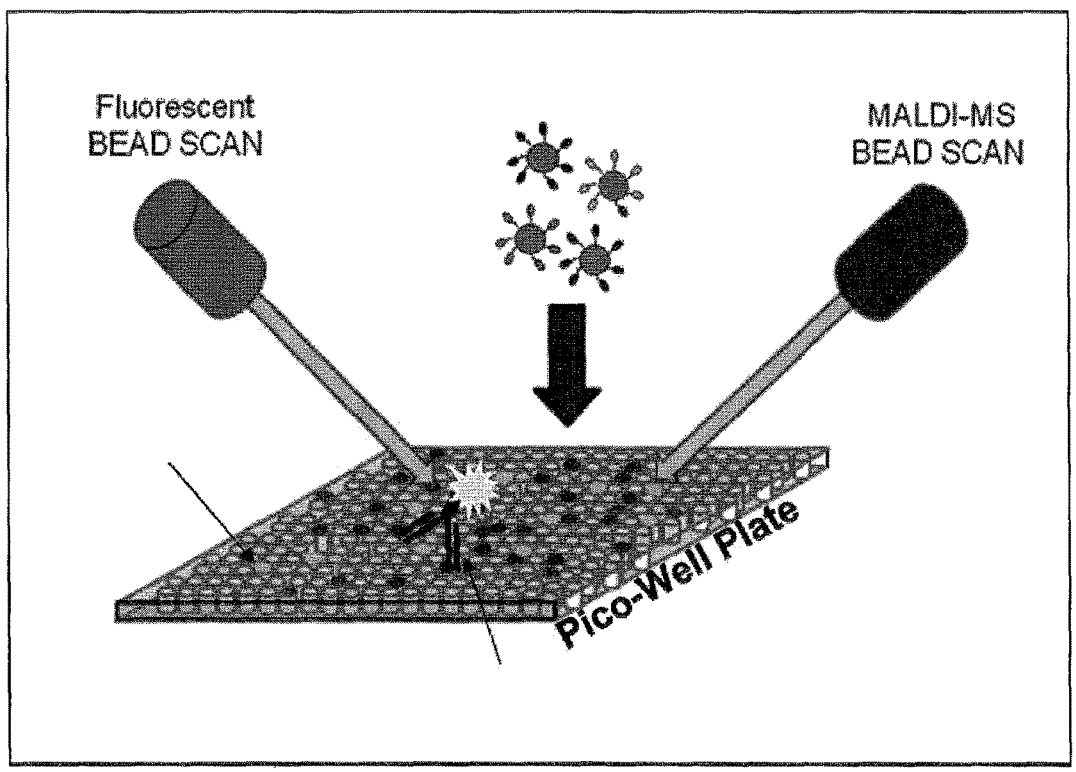

FIG. 21 Example of Bead-Based Global Proteomic Screening (Bead-GPS) with MALDI-TOF MS and Fluorescence Readout.

FIG. 22 Photo-Release of Mass-Tags from Beads. Green mass-tag codes for positive "hit" due to autoantibody interaction with protein bound to bead. Red mass-tag codes for protein identity on bead. Purple mass-tag code is common to all beads in a library used to screen a particular blood serum sample. Yellow oval represents photocleavable linker which is cleaved by near-UV light.

FIG. 23 Attachment of Photocleavable (PC) Mass-Tags to Beads. (1.) PC-Biotin (B) labeled mass-tag attached to (strept)avidin coating (green). (2.) PC-amine modified mass-tag covalently attached through NHS surface chemistry. Yellow circles are the photocleavable nuclei. Affinity capture elements for immobilization of "bait" molecules (e.g. recombinant proteins) are also attached by NHS surface chemistry (not shown).

FIG. 24, Activated Photocleavable (PC)-Mass Tag Reagents for Labeling Probes Used to Query a Bead Library. NHS-activated (amine-reactive) peptide mass tags containing a photocleavable (PC) linker (yellow) are directly conjugated (red arrow) to antibody probes (green). The peptide (purple) lacks any free primary amines (blocked or absent) to prevent self-reactivity.

FIG. 25 Individual steps involved in Bead-GPS.

FIG. 26 Expression Plasmids from the ORFeome. Plasmid constructs of the source ORFeome library (e.g. pDONR223) and conversion into the destination vector (pVSV-DEST) used for cell-free protein expression.

Figure 27:
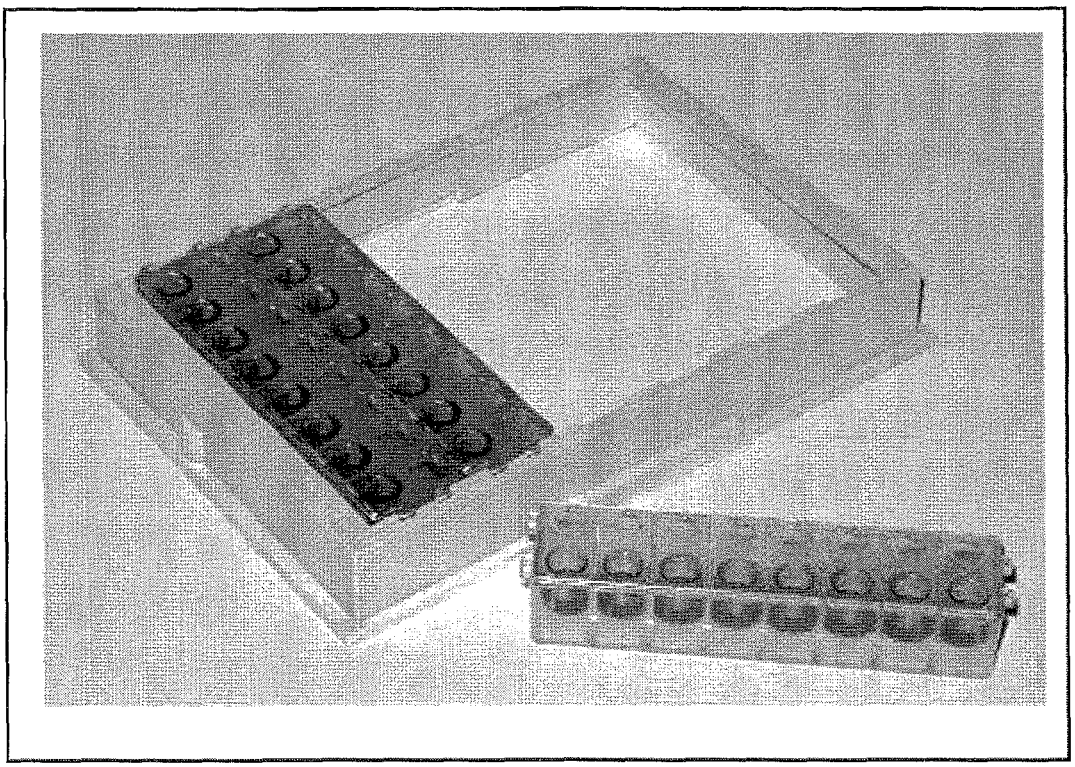

FIG. 27 Dual-Chambered Automation Compatible Devices for High Yield Wheat Germ CECF Expression. Devices use a 96-well frame and foot print for automation compatibility.

FIG. 28 Yield Comparison for Expression of snRNP C in Rabbit Reticulocyte and Wheat Germ Cell-Free Systems. Analysis was by T²-ELISA™. To avoid saturation of the ELISA plate, the amount of expression reaction input into the ELISA was varied.

FIG. 29 Basic Configurations of Beads Comprising BS-LIVE-PRO. Cell-Free expressed proteins (purple) are in situ captured/purified onto beads using an antibody against the C-terminal epitope tag ("C-Tag"). Bead-bound proteins are quantified by fluorescence ("F") antibody-mediated detection of the N-terminal epitope tag (N-Tag). In an alternative configurations, biotins ("B") and/or fluorophores ("F") are directly incorporated using tRNA-mediated co-translational labeling technology developed by AmberGen [Lim and Rothschild (2008) Anal Biochem 383: 103-115]. This affords direct capture onto (strept)avidin beads and/or detection by direct fluorescence.

FIG. 30. Normalization of Expressed Protein Level on Beads Based on T2-ELISA™. Based on estimates of expression yield by T²-ELISA™, the ratio of beads used for capture was modulated to normalize for yield differences of 5 proteins.

Figure 31:
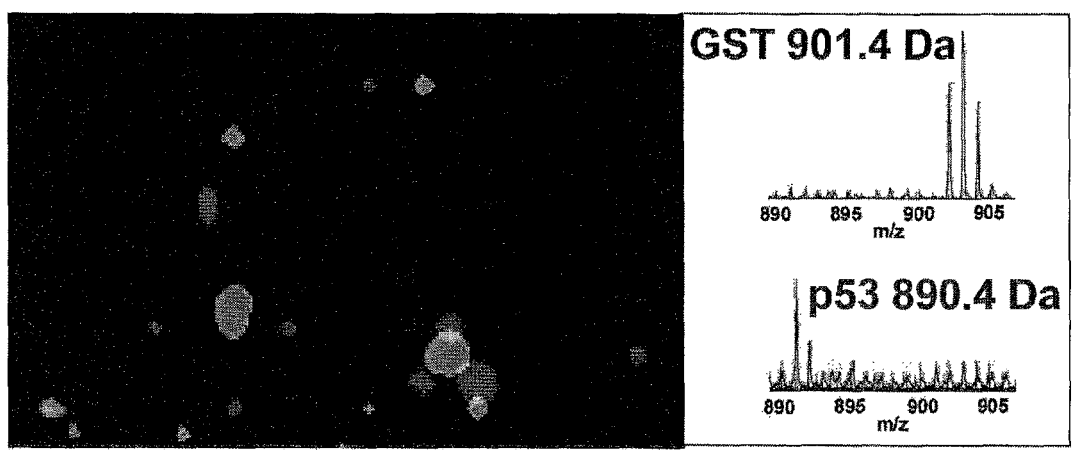

FIG. 31 In Situ Trypsinization Followed by MALDI-MS Imaging and Identification of Cell-Free Expressed Human p53 and GST A2 on Individual Beads.

What is claimed is:

1. A method of detecting the interaction of prey molecules with bait molecules on an array of beads, comprising:
    a. providing a mixture comprising first and second beads, said first beads comprising first bait molecules and said second beads comprising second bait molecules, wherein said first and second bait molecules are different;
    b. contacting said first and second beads with a solution comprising a population of prey molecules, wherein at least a portion of said prey molecules binds to at least one of said first and second beads to create a reacted bead;
    c. making an array with said beads; and
    d. subjecting said array directly to mass spectrometry analysis under conditions wherein said prey from said reacted bead is detected by said mass spectrometry, wherein said mass spectrometry analysis comprises mass spectrometry imaging of individual beads in said array.

2. The method of claim 1, wherein said prey molecules are from blood, serum or plasma.

3. The method of claim 1, wherein said prey molecules are from cell lysates, tissue lysates or cell culture supernatants.

4. The method of claim 1, wherein said prey molecules are proteins or protease digested proteins.

5. The method of claim 1, wherein said prey molecules are peptides or protein fragments.

6. The method of claim 1, wherein said prey molecules are antibodies.

7. The method of claim 1, wherein said prey molecules are nucleic acids.

8. The method of claim 1, wherein said prey molecules are drugs or candidate drugs.

9. The method of claim 1, wherein said bait molecules are proteins, protein fragments or peptides.

10. The method of claim 1, wherein said bait molecules are antibodies.

11. The method of claim 1, wherein said bait molecules are drugs or candidate drugs.

12. The method of claim 1, wherein said bait molecules are nucleic acids.

13. The method of claim 1, wherein said array of step c) is a random array.

14. A method of detecting the interaction of prey molecules with bait molecules on an array of beads, comprising:
    a. providing a mixture comprising first and second beads, said first beads comprising first bait molecules and said second beads comprising second bait molecules, wherein said first and second bait molecules are different;
    b. making an array with said beads;
    c. contacting said array with a solution comprising a population of prey molecules, wherein at least a portion of said prey molecules binds to at least one of said first and second beads in said array to create reacted beads;
    d. subjecting said array directly to mass spectrometry analysis under conditions wherein said prey from said reacted bead is detected by said mass spectrometry, wherein said mass spectrometry analysis comprises mass spectrometry imaging of individual beads in said array.

15. The method of claim 14, wherein said prey molecules are from blood, serum or plasma.

16. The method of claim 14, wherein said prey molecules are from cell lysates, tissue lysates or cell culture supernatants.

17. The method of claim 14, wherein said prey molecules are proteins or protease digested proteins.

18. The method of claim 14, wherein said prey molecules are peptides or protein fragments.

19. The method of claim 14, wherein said prey molecules are antibodies.

20. The method of claim 14, wherein said prey molecules are nucleic acids.

21. The method of claim 14, wherein said prey molecules are drugs or candidate drugs.

22. The method of claim 14, wherein said bait molecules are proteins, protein fragments or peptides.

23. The method of claim 14, wherein said bait molecules are antibodies.

24. The method of claim 14, wherein said bait molecules are drugs or candidate drugs.

25. The method of claim 14, wherein said bait molecules are nucleic acids.

26. The method of claim 14, wherein said array of step c) is a random array.

* * * * *